United States Patent [19]

Bodor

[11] Patent Number: 5,024,998
[45] Date of Patent: * Jun. 18, 1991

[54] PHARMACEUTICAL FORMULATIONS FOR PARENTERAL USE

[75] Inventor: Nicholas S. Bodor, Gainesville, Fla.

[73] Assignee: University of Florida, Gainesville, Fla.

[*] Notice: The portion of the term of this patent subsequent to Jan. 8, 2008 has been disclaimed.

[21] Appl. No.: 448,655

[22] Filed: Dec. 11, 1989

Related U.S. Application Data

[63] Continuation-in-part of Ser. No. 139,755, Dec. 30, 1987, and a continuation-in-part of Ser. No. 174,945, Mar. 29, 1988, and a continuation-in-part of Ser. No. 431,222, Nov. 3, 1989, which is a continuation-in-part of Ser. No. 139,755, , and a continuation-in-part of Ser. No. 174,945, , which is a continuation-in-part of Ser. No. 139,755.

[30] Foreign Application Priority Data

Dec. 13, 1988 [CA] Canada ................................. 585791
Dec. 13, 1988 [IE] Ireland ................................. 3717/88
Mar. 14, 1989 [IE] Ireland ................................. 810/89

[51] Int. Cl.$^5$ ..................... C08B 37/16; A61K 31/735
[52] U.S. Cl. ........................................ 514/58; 536/103; 424/1.1; 424/85.8; 424/94.1; 514/777; 514/937
[58] Field of Search ................. 536/103; 514/58, 937, 514/777; 424/1.1, 85.8, 94.1

[56] References Cited

U.S. PATENT DOCUMENTS

| | | | |
|---|---|---|---|
| 3,459,731 | 8/1969 | Gramera et al. | 260/209 |
| 4,024,223 | 5/1977 | Noda et al. | 514/58 |
| 4,228,160 | 10/1980 | Szejtli et al. | 558/344 |
| 4,232,009 | 11/1980 | Hayashi et al. | 514/58 |
| 4,351,846 | 9/1982 | Matsumoto et al. | 514/530 |
| 4,352,793 | 10/1982 | Yamahira et al. | 514/58 |
| 4,383,992 | 5/1983 | Lipari . | |
| 4,407,795 | 10/1983 | Nicolau . | |
| 4,424,209 | 1/1984 | Tuttle . | |
| 4,425,336 | 1/1984 | Tuttle . | |
| 4,438,106 | 3/1984 | Wagu et al. | 514/58 |
| 4,474,811 | 10/1984 | Matsuda et al. | 514/570 |
| 4,478,995 | 10/1984 | Shinoda et al. | 536/46 |
| 4,479,932 | 10/1984 | Bodor | 424/9 |
| 4,479,944 | 10/1984 | Hayashi et al. | 514/58 |
| 4,479,966 | 10/1984 | Hayashi et al. | 514/58 |
| 4,497,803 | 2/1985 | Harada et al. | 514/450 |
| 4,499,085 | 2/1985 | Masuda | 514/58 |

(List continued on next page.)

FOREIGN PATENT DOCUMENTS

| | | |
|---|---|---|
| 0197571 | 10/1986 | European Pat. Off. . |
| 58-213712 | 12/1983 | Japan . |
| 59-104556 | 6/1984 | Japan . |
| 60-054384 | 3/1985 | Japan . |
| 61-070996 | 4/1986 | Japan . |
| 61-197602 | 9/1986 | Japan . |
| 62-003795 | 1/1987 | Japan . |
| 62-106901 | 5/1987 | Japan . |
| 62-164701 | 7/1987 | Japan . |
| 61-236802 | 10/1987 | Japan . |
| 62-281855 | 12/1987 | Japan . |
| 63-027440 | 2/1988 | Japan . |
| 63-036793 | 2/1988 | Japan . |
| 63-135402 | 6/1988 | Japan . |
| 63-146861 | 6/1988 | Japan . |
| 63-218663 | 9/1988 | Japan . |

(List continued on next page.)

OTHER PUBLICATIONS

Chemical Abstracts, 110, 101775b (Abstract of Japanese Kokai 88/218,663, published Sep. 12, 1988).
Irie et al., Pharmaceutical Research, vol. 5, No. 11, 1988, 713–717.
Yoshida et al., International Journal of Pharmaceutics, 46, 1988, 217–222.

(List continued on next page.)

Primary Examiner—Ronald W. Griffin
Attorney, Agent, or Firm—Mary Katherine Baumeister

[57] ABSTRACT

Aqueous parenteral solutions of drugs which are insoluble or only sparingly soluble in water and/or which are unstable in water, combined with cyclodextrin selected from the group consisting of hydroxypropyl, hydroxyethyl, glucosyl, maltosyl and maltotriosyl derivatives of $\beta$- and $\gamma$-cyclodextrin, provide a means for alleviating problems associated with drug precipitation at the injection site and/or in the lungs or other organs following parenteral administration.

86 Claims, 2 Drawing Sheets

U.S. PATENT DOCUMENTS

| | | | |
|---|---|---|---|
| 4,518,588 | 5/1985 | Szejtli et al. | 514/58 |
| 4,524,068 | 6/1985 | Szejtli et al. | 514/58 |
| 4,540,564 | 9/1985 | Bodor | 424/9 |
| 4,555,504 | 11/1985 | Jones | 514/26 |
| 4,565,807 | 1/1986 | Uekama et al. | 514/58 |
| 4,575,548 | 3/1986 | Ueda et al. | 514/46 |
| 4,596,795 | 6/1986 | Pitha | 514/58 |
| 4,598,070 | 7/1986 | Ohwaki et al. | 514/58 |
| 4,599,327 | 7/1986 | Nogradi et al. | 514/58 |
| 4,603,123 | 7/1986 | Chiesi et al. | 514/58 |
| 4,608,366 | 8/1986 | Hasegawa et al. | 514/58 |
| 4,617,298 | 10/1986 | Bodor et al. | 514/176 |
| 4,623,641 | 11/1986 | Szejtli et al. | 514/58 |
| 4,659,696 | 4/1987 | Hirai et al. | 514/15 |
| 4,663,316 | 5/1987 | Ninger et al. | 514/99 |
| 4,675,395 | 6/1987 | Fukazawa et al. | 536/103 |
| 4,727,064 | 2/1988 | Pitha | 514/58 |
| 4,727,079 | 2/1988 | Bodor | 514/307 |
| 4,728,509 | 3/1988 | Shimizu et al. | 424/81 |
| 4,728,510 | 3/1988 | Shibanai et al. | 424/94.5 |
| 4,751,095 | 6/1988 | Karl et al. | 426/548 |
| 4,764,604 | 8/1988 | Müller | 536/103 |
| 4,824,850 | 4/1989 | Bodor | 514/270 |
| 4,829,070 | 5/1989 | Bodor | 514/307 |
| 4,834,985 | 5/1989 | Elger et al. | 424/488 |
| 4,888,427 | 12/1989 | Bodor | 546/316 |

FOREIGN PATENT DOCUMENTS

| | | |
|---|---|---|
| 8303968 | 11/1983 | PCT Int'l Appl. |
| 8502767 | 7/1985 | PCT Int'l Appl. |
| 8503937 | 9/1985 | PCT Int'l Appl. |

OTHER PUBLICATIONS

Koizumi et al., *Chem. Pharm. Bull.,* 35(8), 3413–3418 (1987).

Okada et al., *Chem. Pharm. Bull.,* 36(6), 2176–2185 (1988).

Yamamoto et al., in *International Journal of Pharmaceutics,* 49, 163–171 (1981).

Brewster et al., *J. Pharm. Sci.,* vol. 77, No. 11, Nov. 1988, 981–985.

Brewster et al., in *Proceedings of the Fourth International Symposium on Cyclodextrins,* Munich, 20th–22nd Apr., 1988, pp. 399–404, Kluwer Academic Publishers, Dordrecht, NL.

Pitha et al., in *Controlled Drug Delivery,* ed. S. D. Bruck, vol. I, CRC Press, Boca Raton, Fla., 125–148 (1983).

Uekama, *Pharm. Int.,* Mar. 1985, 61–65.

Pitha, *Journal of Inclusion Phenomena* 2, 477–485 (1984).

Fenyvesi et al., *Chem. Pharm. Bull.* 32 (2), 665–669 (1984).

Uekama et al., *International Journal of Pharmaceutics,* 23, 35–42 (1985).

Pitha, J. Pharm. Sci., vol. 74, No. 9, Sep. 1985, 987–990.

Matsuyama et al., *Drug Development and Industrial Pharmacy,* 13(15), 2687–2691 (1987).

Pitha et al., *International Journal of Pharmaceutics,* 29, 73–82 (1986).

Uekama et al., in *CRC Critical Reviews in Therapeutic Drug Carrier Systems,* vol. 3(1), 1–40 (1987).

Uekama, in *Topics in Pharmaceutical Sciences,* 1987, eds. D. D. Breimer & P. Speiser Publishers, B.V. (Biomedical Division), 181–194 (1987).

Pagington, *Chemistry in Britain,* 455–458 (May 1987).

Carpenter et al., *The Journal of Pediatrics,* III, 507–512 (Oct. 1987).

Estes et al. in *Biological Approaches to the Controlled Delivery of Drugs,* ed. R. L. Juliano, Annals of the New York Academy of Sciences, vol. 907, 1987, 334–336.

PHARMACEUTICAL FORMULATIONS FOR PARENTERAL USE

CROSS-REFERENCE TO RELATED APPLICATIONS

This application is a continuation-in-part of applicant's copending application Ser. No. 07/139,755, filed Dec. 30, 1987, of applicant's copending application Ser. No. 07/174,945, filed Mar. 29, 1988, and of applicant's copending application Ser. No. 07/431,222, filed Nov. 3, 1989. Ser. No. 07/174,945 is itself a continuation-in-part of Ser. No. 07/139,755, and Ser. No. 07/431,222 is itself a continuation-in-part of Ser. No. 07/139,755 and Ser. No. 07/174,945. All three copending earlier applications are incorporated by reference herein in their entirety and relied upon.

FIELD OF THE INVENTION

The present invention relates to aqueous parenteral solutions of drugs which are insoluble or only sparingly soluble in water and/or which are unstable in water, combined with selected cyclodextrins. The solutions provide a means for alleviating problems associated with drug precipitation at the injection site and/or in the lungs or other organs following parenteral administration.

BACKGROUND OF THE INVENTION

Cyclodextrins are cyclic oligosaccharides. The most common cyclodextrins are $\alpha$-cyclodextrin, which is composed of a ring of six glucose residues; $\beta$-cyclodextrin, which is composed of a ring of seven glucose residues; and $\gamma$-cyclodextrin, which is composed of a ring of eight glucose units. The inside cavity of a cyclodextrin is lipophilic, while the outside of the cyclodextrin is hydrophilic; this combination of properties has led to widespread study of the natural cyclodextrins, particularly in connection with pharmaceuticals, and many inclusion complexes have been reported. $\beta$-Cyclodextrin has been of special interest because of its cavity size, but its relatively low aqueous solubility (about 1.8% w/v at 25° C.) and attendant nephrotoxicity have limited its use in the pharmaceutical field.

Attempts to modify the properties of the natural cyclodextrins have resulted in the development of heptakis (2,6-di-0-methyl)-$\beta$-cyclodextrin, heptakis (2,3,6-tri-0-methyl)-$\beta$-cyclodextrin, hydroxypropyl-$\beta$-cyclodextrin, $\beta$-cyclodextrin-epichlorohydrin polymer and others. For a comprehensive review of cyclodextrins and their use in pharmaceutical research, see Pitha et al, in *Controlled Drug Delivery*, ed. S. D. Bruck, Vol. I, CRC Press, Boca Raton, Fla., pp. 125–148 (1983). For an even more recent overview, see Uekama et al, in *CRC Critical Reviews in Therapeutic Drug Carrier Systems*, Vol. 3 (1), 1–40 (1987); Uekama, in *Topics in Pharmaceutical Sciences* 1987, eds. D. D. Breimer and P. Speiser, Elsevier Science Publishers B. V. (Biomedical Division), 1987, 181–194; and Pagington, *Chemistry in Britain*, May 1987, pp. 455–458.

Inclusion complexes of $\alpha$-, $\beta$- or $\gamma$-cyclodextrin or their mixtures with a variety of drugs have been described by numerous parties and various advantages have been attributed to the complexes. These descriptions include the following:

| INVENTOR | U.S. PAT. NO. | ACTIVE INGREDIENT | USE | ADVANTAGE |
|---|---|---|---|---|
| Noda et al | 4,024,223 | menthol &/or methyl salicylate | antiphlogistic, analgesic | reduced unpleasant odor, increased wet packing effect |
| Szejtli et al | 4,228,160 | indomethacin | anti-inflammatory, protective during pregnancy | reduced ulcerative effect |
| Hayashi et al | 4,232,009 | $\omega$-halo-PGI$_2$ analogs | hypotensive, uterine contraction stimulating, blood platelet aggregation inhibiting | increased stability |
| Matsumoto et al | 4,351,846 | 3-hydroxy- and 3-oxo-prostaglandin analogs | uterine contraction stimulating | increased stability |
| Yamahira et al | 4,352,793 | bencyclane fumarate | anticonvulsant, vasodilative | increased stability at strong acid pH, faster gastric emptying, higher blood concentrations, less irritation, improved hemolytic activity |
| Lipari | 4,383,992 | steroids—corticosteroids, androgens, anabolic steroids, estrogens, progestagens | hormonal | improved water solubility, increased therapeutic response in eye |
| Nicolau | 4,407,795 | p-hexadecyl-aminobenzoic acid sodium salt | antiatherosclerotic | enhanced bioavailability |
| Tuttle[1] | 4,424,209 | 3,4-diisobutyryloxy-N-[3-(4- | cardiac contractility | |

| INVENTOR | U.S. PAT. NO. | ACTIVE INGREDIENT | USE | ADVANTAGE |
| --- | --- | --- | --- | --- |
| | | isobutyryloxy-phenyl)-1-methyl-n-propyl]-β-phenethylamine | agent | |
| Tuttle | 4,425,336 | 3,4-dihydroxy-N-[3-(4-hydroxy-phenyl)-1-methyl-n-propyl]-β-phenethylamine | cardiac contractility agent | capable of oral administration |
| Wagu et al | 4,438,106 | EPA and DHA (fatty acids) | | deodorized, storage stable |
| Masuda et al[2] | 4,474,811 | 2-(2-fluoro-4-biphenylyl)propionic acid or salt | anti-inflammatory ophthalmic | reduced eye irritation, higher concentrations, no side effects, highly soluble, long stability, excellent pharmacological effects |
| Shinoda et al | 4,478,995 | acid addition salt of (2'-benzyloxycarbonyl)phenyl trans-4-guanidinomethylcyclohexanecarboxylate | anti-ulcer | excellent water solubility, good absorption in digestive tract, good anti-ulcer activity |
| Hayashi et al | 4,479,944 | $PGI_2$ analog | for treatment of artereosclerosis, cardiac failure or thrombosis | stabilization against decomposition |
| Hayashi et al | 4,479,966 | 6,9-methano-$PGI_2$ analogs | for hypertension, cerebral thrombosis and the like | increased stability |
| Harada et al | 4,497,803 | lankacidin-group antibiotic | antibiotic for swine dysentery | enhanced water solubility and stability, increased rate and amount of absorption |
| Masuda | 4,499,085 | prostaglandin analog | treating anoxia of brain cells | |
| Szejtli et al | 4,518,588 | phendiline, i.e. N-(1-phenyl-ethyl)-3,3-diphenylpropylamine or its hydrochloride | coronary dilator calcium antagonist | improved water solubility, accelerated and increased in vivo resorption & dissolution at pH/temperature of gastric acid |
| Szejtli et al | 4,524,068 | piperonyl butoxide | synergizes pesticidal effect of known insecticides and fungicides | easily handled crystalline solid; improved water solubility, increased absorption & velocity of penetration through biological membranes |
| Jones | 4,555,504 | a cardiac glycoside | cardiac effect | high aqueous solubility, apparently better bioavailability |
| Uekama et al[3] | 4,565,807 | pirprofen | anti-inflammatory, analgesic, antipyretic | improved stability to oxidation, freedom from bitter taste, less irritating |
| Ueda et al | 4,575,548 | 2-nitroxymethyl-6-chloropyridine | for vascular disorders | non-volatile powder vs. volative oil |
| Ohwaki et al[4] | 4,598,070 | tripamide | anti-hypertensive | improved solubility |
| Chiesi et al | 4,603,123 | piroxicam, i.e. 4-hydroxy-2-methyl-N-2-pyridyl-2H-1,2-benzothiazine-3-carboxamide-1,1-dioxide | anti-inflammatory, analgesic | |
| Hasegawa et al | 4,608,366 | mobenzoxamine, | antiemetic, | storage stability, |

-continued

| INVENTOR | U.S. PAT. NO. | ACTIVE INGREDIENT | USE | ADVANTAGE |
|---|---|---|---|---|
| | | i.e. 1-[2-(4-methoxybenzhydryloxy)ethyl]-4-[3-(4-fluorobenzoyl)propyl]-piperazine | antispasmodic | better absorption through digestive tract |
| Hirai et al[2] | 4,659,696 | polypeptide | | improving drug absorption by non-oral and non-injection routes |
| Szejtli et al | 4,623,641 | $PGI_2$ methyl ester | anti-ulcer | improved storage stability |
| Ninger et al | 4,663,316 | unsaturated phosphorus-containing antibiotics, including phosphotrienin | antibiotic, antifungal, antitumor | enhanced stability against oxidation |
| Fukazawa et al | 4,675,395 | hinokitiol | bactericidal, bacteriostatic | improved water solubility, less odor |
| Shimizu et al | 4,728,509 | 2-amino-7-isopropyl-5-oxo-5H-[1]-benzopyrano-[2,3-b]pyridine-3-carboxylic acid | anti-allergic, anti-inflammatory | improved water solubility to increase concentration to therapeutic levels in nasal drops and eye drops |
| Shibanai et al[6] | 4,728,510 | a milk component | bath preparation | improved stability |
| Karl et al | 4,751,095 | aspartame | dipeptide sweetener | stabilization from hydrolysis |

[1] Tuttle also describes use of 2,6-di-0-methyl-β-cyclodextrin and 2,3,6-tri-0-methyl-β-cyclodextrin to form the inclusion complex.
[2] This may not be an inclusion complex, but simply a physical mixture. Indeed, it appears from the claims that an inclusion product is not formed and that what the invention provides is a pharmaceutical composition consisting of a physical mixture of a hydrophilic, physiologically active polypeptide and cyclodextrin, said composition being a uniform mixture in dosage form. The cyclodextrin may be α-, β- or γ-cyclodextrin, or a cyclodextrin derivative, exemplified by tri-0-methylcyclodextrin and triaminocyclodextrin, α-cyclodextrin being particularly preferred. The composition is designed for nasal, vaginal or rectal administration, i.e. a non-oral or non-injectable route of administration is used.
[3] This is a mixture and/or an inclusion compound.
[4] The inventors also mention prior known solubility improvements of cyclodextrin inclusions of barbituric acid derivatives, mefenamic acid, indomethacin and chloramphenicol.
[5] The inventors refer to this as an "occlusion" compound.
[6] The inventors also mention a derivative of cyclodextrin and a cyclodextrin-containing starch decomposition product for use in forming the clathrate.

Matsuyama et al, *Drug Development and Industrial Pharmacy*, 13(15), 2687–2691 (1987), have reported on the thermodynamics of binding aromatic amino acids to α-, β- and γ-cyclodextrin. Human serum albumin, which contains aromatic amino acids, was also tested as a protein model. The authors suggest that cyclodextrins may protect peptides from enzymatic hydrolysis. Also, according to Sekisui Chemical Co., Ltd.'s Japanese Kokai Tokkyo Koho JP No. 59/104556 (84/104556), published June 16, 1984, cyclized oligosaccharides such as β-cyclodextrin have been recently used in protein stabilizers which prevent denaturation of proteins and enzymes in blood. Human blood mixed with octylphenoxypoly(ethoxyethanol) and β-cyclodextrin was maintained for 24 hours with little change.

Inclusion complexes of 2,6-di-0-methyl-β-cyclodextrin with dibenzo[bd]pyran derivatives and salts having analgesic, antemetic and narcosispotentiating activities have been described in Nógrádi et al U.S. Pat. No. 4,599,327; increased water solubility and thus improved biological activity have been claimed for the complexes. A review of the pharmaceutical applications of such methylated cyclodextrins has been published by Uekama, *Pharm. Int.*, Mar. 1985, 61–65; see also Pitha, *Journal of Inclusion Phenomena* 2, 477–485 (1984).

Cyclodextrin polymer has been reported by Fenyvesi et al, *Chem. Pharm. Bull.* 32 (2), 665–669 (1984) to improve the dissolution of furosemide. Improvements in the dissolution and absorption of phenytoin using a water-soluble β-cyclodextrin epichlorohydrin polymer have been described by Uekama et al, *International Journal of Pharmaceutics*, 23, 35–42 (1985).

Hydroxypropyl-β-cyclodextrin (HPCD) and its preparation by propylene oxide addition to β-cyclodextrin were described in Gramera et al U.S. Pat. No. 3,459,731 nearly 20 years ago. Gramera et al also described the analogous preparation of hydroxyethyl-β-cyclodextrin by ethylene oxide reaction with β-cyclodextrin. Much more recently, Pitha and co-workers have described the improved preparation of this cyclodextrin derivative and its effects on the dissolution of various drug molecules. Pitha U.S. Pat. No. 4,596,795, dated June 24, 1986, describes inclusion complexes of sex hormones, particularly testosterone, progesterone, and estradiol, with specific cyclodextrins, preferably hydroxypropyl-β-cyclodextrin and poly-β-cyclodextrin. The complexes enable the sex hormones to be successfully delivered to the systemic circulation via the sublingual or buccal route; the effectiveness of this delivery is believed to be due to "the high dissolution power of hydrophilic derivatives of cyclodextrins, the non-aggregated structure of their complexes with steroids, and their low toxicity and irritancy of mouth tissue". Success with other cyclodextrins, including poly-γ-cyclodextrin and hydroxypropyl-γ-cyclodextrin, have also been noted in the Pitha patent. See also Pitha et al, *J. Pharm. Sci.*, Vol. 74, No. 9, September 1985, 987-990, concerning the same and related studies. Pitha et al also describe in the *J. Pharm. Sci.* article the storage stability of tablets containing a testosteronehydroxypropyl-β-cyclodextrin complex and the lack of toxicity of the cyclodextrin itself, as well as the importance of the amorphous nature of the cyclodextrin derivatives and their complexes with drugs in improving dissolution properties.

The improved, optimized preparation and purification of hydroxypropyl-β-cyclodextrin has been recently described by Pitha et al, *International Journal of Pharmaceutics*, 29, 73-82 (1986). In the same publication, the authors have described increased water solubility for 32 drugs in concentrated (40 to 50%) aqueous solutions of hydroxypropyl-β-cyclodextrin; improved solubilization of acetamidophen, apomorphine, butylated hydroxytoluene, chlorthalidone, cholecalciferol, dexamethasone, dicumarol, digoxin, diphenylhydantoin, estradiol, estriol, ethinylestradiol-3-methyl ether, ethisterone, furosemide, hydroflumethiazide, indomethacin, iproniazid phosphate, 17-methyltestosterone, nitroglycerin, norethindrone, ouabain, oxprenolol, progesterone, retinal, retinoic acid (all trans and salt forms), retinol, spironolactone, sulpiride, testosterone and theophylline was noted. The authors indicated this to be an extension of their earlier work with hydroxypropyl-β-cyclodextrin, which was previously found effective for oral administration of the sex hormones to humans. Their later work reported in Pitha et al, *International Journal of Pharmaceutics*, 29, 73-82 (1986), has also been very recently described in Pitha U.S. Pat. No. 4,727,064, dated Feb. 23, 1988. That patent claims a composition containing an amorphous complex of cyclodextrin and a drug, and a method of producing a stabilizing amorphous complex of a drug and a mixture of cyclodextrins comprising (1) dissolving an intrinsically amorphous mixture of cyclodextrin derivatives which are water soluble and capable of forming inclusion complexes with drugs in water; and (2) solubilizing lipophilic drugs into aqueous media to form a solution and form a solubilized drug/cyclodextrin complex. The patent describes the preparation of various substituted amorphous cyclodextrins, including hydroxypropyl-β-cyclodextrin and hydroxypropyl-γ-cyclodextrin, the latter by analogous condensation of propylene oxide and γ-cyclodextrin.

Uekama et al, *CRC Critical Reviews in Therapeutic Drug Carrier Systems*, Vol. 3 (1), pp. 1-40 (1987), have described the characteristics of various cyclodextrins, including hydroxypropyl-β-cyclodextrin. The authors have presented data showing improved solubilization in water in the presence of 15 mg/mL of HPCD for the drugs carmofur, diazepam, digitoxin, digoxin, flurbiprofen, indomethacin, isosorbide dinitrate, phenytoin, prednisolone, progesterone and testosterone. In a discussion of the metabolism and toxicity of cyclodextrins, Uekama et al have indicated that cyclodextrins at sufficiently high concentrations cause hemolysis, and that the methylated cyclodextrins have higher hemolytic activity than the natural cyclodextrins. Hydroxypropyl-β-cyclodextrin is said to cause hemolysis beginning at 4.5 mM. The authors have further indicated that parenteral administration of large doses of cyclodextrins should be avoided, but that "γ-cyclodextrin and hydroxypropyl-β-cyclodextrin seem to be useful in drug solubilization for injections and liquid preparations used for mucous membranes."

JANSSEN PHARMACEUTICA N.V.'s International Patent Application No. PCT/EP84/00417, published under International Publication No. W085/02767 on July 4, 1985, has described pharmaceutical compositions comprising inclusion compounds of drugs, which are unstable or only sparingly soluble in water, with partially etherified β-cyclodextrin derivatives having hydroxyalkyl and optionally additional alkyl groups. Among the cyclodextrin derivatives contemplated is hydroxypropyl-β-cyclodextrin, while the drugs include nonsteroidal anti-rheumatic agents, steroids, cardiac glycosides and derivatives of benzodiazepine, benzimidazole, piperidine, piperazine, imidazole and triazole. Preferred drugs include etomidate, ketoconazole, tubulazole, itraconazole, levocabastine and flunarizine. The pharmaceutical compositions of the invention include oral, parenteral and topical formulations, with 4 to 10% solutions of cyclodextrin derivatives being utilized to solubilize various drugs. Improved solubilities of indomethacin, digitoxin, progesterone, dexamethasone, hydrocortisone and diazepam using 10% HPCD are shown, and an injectable formulation of diazepam in 7% HPCD is specifically described. The relatively low cyclodextrin concentrations used reflect a desire to avoid or minimize the hemolytic effects observed at higher cyclodextrin concentrations.

Japanese Kokai No. 88-218,663 (Kamikama et al) describes a pharmaceutical preparation containing nimodipine solubilized with hydroxypropyl-β-cyclodextrin.

Carpenter et al, *The Journal of Pediatrics*, 111, 507-512 (October 1987) describe intravenous infusion of 2-hydroxypropyl-β-cyclodextrin, prepared as a 5% solution in water, to treat severe hypervitaminosis A. It was found that, during infusion, circulating retinyl esters increased transiently, while total vitamin A excreted in the urine was enhanced after infusion. Thus, intravenous infusion of 5% HPCD was found to decrease in vivo levels of the vitamin, presumably by complexing with the vitamin and removing some of the excess from the body.

The preparation of amorphous water-soluble cyclodextrin derivatives, including 2-hydroxyethyl-β-cyclodextrin, 3-hydroxypropyl-β-cyclodextrin and 2-hydroxypropyl-γ-cyclodextrin, is described by Irie et al, *Pharmaceutical Research*, Vol. 5, No. 11, 1988, 713-717. That report also addresses the distribution of the substituents among the glucose residues of the cyclodextrin ring.

A pharmaceutical evaluation of hydroxyalkyl ethers of β-cyclodextrin has been recently reported by Yoshida et al, *International Journal of Pharmaceutics* 46, 1988, 217-222. Aqueous solubilities, surface activities, hemolytic activity and local irritancy are reported. The data suggest that hydroxyalkyl-β-cyclodextrins overcome many of the undesirable characteristics of β-cyclodextrin usage in pharmaceuticals.

JANSSEN PHARMACEUTICA N.V.'s European Patent Application No. 86200334.0, published under EPO Publication No. 0197571 on Oct. 15, 1986, describes γ-cyclodextrin derivatives which are γ-cyclodextrin substituted with $C_1$-$C_6$ alkyl, hydroxy $C_1$-$C_6$ alkyl, carboxy $C_1$-$C_6$ alkyl or $C_1$-$C_6$ alkyloxycarbonyl $C_1$-$C_6$ alkyl or mixed ethers thereof. Among the specific derivatives named are hydroxypropyl-γ-cyclodextrin and hydroxyethyl-γ-cyclodextrin. Compositions comprising the cyclodextrin derivatives and a drug are also described. See also corresponding Müller U.S. Pat. No. 4,764,604, dated Aug. 16, 1988.

The inclusion characteristics of yet other derivatized cyclodextrins have also been described in the literature. Studies of branched cyclodextrins which are glucosyl and maltosyl derivatives of $\alpha$-, $\beta$-and $\gamma$-cyclodextrin and their inclusion complexes with drugs have recently been reported. Uekama, in *Topics in Pharmaceutical Sciences* 1987, eds. D. D. Breimer and P. Speiser, Elsevier Science Publishers B. V. (Biomedical Division), 1987, 181–194, has described the effects on bio-pharmaceutical properties of maltosyl and glucosyl cyclodextrin derivatives, as well as hydroxypropyl and other hydrophilic cyclodextrin derivatives, including enhanced drug absorption. The mechanism of enhancing drug absorption is described and the apparent stability constants for inclusion complexes of various drugs with $\beta$-cyclodextrin, dimethyl-$\beta$-cyclodextrin, hydroxypropyl-$\beta$-cyclodextrin and maltosyl-$\beta$-cyclodextrin are given. Drugs studied with these cyclodextrins include benoxaprofen, biphenyl acetic acid, carmofur, clofibrate, chloropromazine, diazepam, diclofenac, digitoxin, digoxin, ethyl 4-biphenyl acetate, flurbiprofen, isosorbide dinitrate, indomethacin, menadione, nimodipine, nisoldipine, phenytoin, prednisolone, progesterone, prostacyclin, various prostaglandins ($E_1$, $E_2$, $A_1$, $A_2$), protriptyline, spironolactone and testosterone. Uekama also discussed the hemolytic effects of cyclodextrins. Summarizing the various studies using human erythrocytes, Uekama indicated that the natural cyclodextrins at relatively *high* concentrations caused hemolysis in the order $\gamma < \alpha < \beta$. In the case of chemically modified cyclodextrins, the order changed to hydroxyethyl-$\beta$ < maltosyl-$\beta$ < hydroxypropyl-$\beta$ < $\beta$. At relatively *low* concentrations, the cyclodextrins provided protection from hemolysis induced with various membrane-perturbing drugs, suggesting complexation as a means of reducing local toxicity of drugs: The natural cyclodextrins were found to reduce muscular tissue damage following intramuscular injection of drugs. Uekama concluded that the protective effects of cyclodextrins "are atrributable to the poor affinity of the hydrophilic complex to muscular tissue membrane. The hydroxyethyl, hydroxypropyl, and glucosyl CyDs are more effective to reduce the local toxicity induced by drugs compared with natural CyDs, owing to the highly hydrophilic nature".

Koizumi et al, *Chem. Phar. Bull.* 35 (8), 3413–3418 (1987), have reported on inclusion complexes of poorly water-soluble drugs with glucosyl cyclodextrins, namely 6-0-$\alpha$-D-glucosyl-$\alpha$-CD ($G_1$-$\alpha$-CD), 6-0-$\alpha$-D-glucosyl-$\beta$-CD ($G_1$-$\beta$-CD) and $6^A$,$6^D$-di-0-$\alpha$-D-glucosyl-$\beta$-CD ($2G_1$-$\beta$-CD).

Okada et al, *Chem. Pharm. Bull.*, 36 (6), 2176–2185 (1988), have reported on the inclusion complexes of poorly water-soluble drugs with maltosyl cyclodextrins, namely 6-0-$\alpha$-maltosyl-$\alpha$-CD ($G_2$-$\alpha$-CD), 6-0-$\alpha$-maltosyl-$\beta$-CD ($G_2$-$\beta$-CD), 6-0-$\alpha$-maltosyl-$\gamma$-CD ($G_2$-$\gamma$-CD), 6-0-$\alpha$-maltotriosyl-$\alpha$-CD ($G_3$-$\alpha$-CD), 6-0-$\alpha$-maltotriosyl-$\beta$-CD ($G_3$-$\beta$-CD) and 6-0-$\alpha$-maltotriosyl-$\gamma$-CD ($G_3$-$\gamma$-CD).

Yamamoto et al, in *International Journal of Pharmaceutics* 49, 163–171 (1989), have described physicochemical properties of branched $\beta$-cyclodextrins such as glucosyl-$\beta$-cyclodextrin, maltosyl-$\beta$-cyclodextrin and di-maltosyl-$\beta$-cyclodextrin, and their inclusion characteristics. Those authors report that the branched $\beta$-cyclodextrins are better solubilizers for poorly water-soluble drugs and have less hemolytic activity than $\beta$-cyclodextrin itself, and they suggest that glucosyl-$\beta$-cyclodextrin and maltosyl-$\beta$-cyclodextrin may be especially useful in parenteral preparations.

The patent literature reflects much recent work on the branched cyclodextrins carried out by Japanese workers, as discussed below.

Japanese Kokai 63-135402 (TOKUYAMA SODA KK), published June 7, 1988, describes compositions consisting of maltosyl-$\beta$-cyclodextrin and at least one of digitoxin, nifedipine, flulubiprophene, isosorbide nitrate, phenytoin, progesterone or testosterone. The compositions have improved water solubility and reduced erythrocyte destruction, are safe for humans and can be used as injections, eye drops, syrups, and for topical and mucous membrane application.

Japanese Kokai 62-281855 (DAIKIN KOGYO KK), published Dec. 7, 1987, describes stable, water-soluble inclusion compounds of maltosyl-$\beta$-cyclodextrin with a variety of vitamins and hormones, e.g. steroid hormones such as prednisolone, hydrocortisone and estriol. These lipophilic vitamins and hormones can thus be used as aqueous solutions.

Japanese Kokai 63-036793 (NIKKEN CHEM KK), published Feb. 17, 1988, describes the preparation of dimaltosyl-$\gamma$-cyclodextrin and its general use in medicines.

Japanese May 18, 1987, describes the preparation of diglucosyl-$\beta$-cyclodextrin and its general use for pharmaceuticals.

Japanese Kokai 61-236802 (NIKKEN CHEM KK), published Oct. 22, 1986, describes the preparation of maltosyl-$\gamma$-cyclodextrin and its general use with drugs.

Japanese Kokai 61-197602 (NIKKEN CHEM KK), published Sept. 1, 1986, describes the preparation of maltosyl-$\beta$-cyclodextrin and its expected use in medicines.

Japanese Kokai 61-070996 (NIKKEN CHEM KK), published Apr. 11, 1986, describes the preparation of maltosyl-$\alpha$-cyclodextrin and its general use in pharmaceuticals.

Japanese Kokai 63-027440 (SANRAKU OCEAN), published Feb. 5, 1988, describes compositions containing a water-insoluble or slightly soluble drug together with glucosylated branched cyclodextrin. Among the drugs mentioned are steroid hormones.

Japanese Kokai 62-164701 (SHOKUHIN SANGYO BIO), published July 21, 1987, describes the preparation of diglucosyl-$\alpha$-cyclodextrin and its general use in medicine.

Japanese Kokai 62-003795 (TOKUYAMA SODA KK), published Jan. 9, 1987, describes production of glucose and maltoligosaccharide (2–4 glucose units) derivatives of $\alpha$-, $\beta$- and $\gamma$-cyclodextrin and their use as stabilizers for pharmaceuticals.

The delivery of drugs to the brain is often seriously limited by transport and metabolism factors and, more specifically, by the functional barrier of the endothelial brain capillary wall, i.e. the blood-brain barrier or BBB. Site-specific delivery and sustained delivery of drugs to the brain are even more difficult.

A dihydropyridine⇌pyridinium salt redox system has recently been successfully applied to delivery to the brain of a number of drugs. Generally speaking, according to this system, a dihydropyridine derivative of a biologically active compound is synthesized, which derivative can enter the CNS through the blood-brain barrier following its systematic administration. Subsequent oxidation of the dihydropyridine species to the corresponding pyridinium salt leads to delivery of the drug to the brain.

Three main approaches have been published thus far for delivering drugs to the brain using this redox system. The first approach involves derivation of selected drugs which contain a pyridinium nucleus as an integral structural component. This approach was first applied to delivering to the brain N-methylpyridinium-2-carbaldoxime chloride (2-PAM), the active nucleus of which constitutes a quaternary pyridinium salt, by way of the dihydropyridine latentiated prodrug form thereof. Thus, a hydrophilic compound (2-PAM) was made lipoidal (i.e. lipophilic) by making its dihydropyridine form (Pro-2-PAM) to enable its penetration through lipoidal barriers. This simple prodrug approach allowed the compound to get into the brain as well as other organs, but this manipulation did not and could not result in any brain specificity. On the contrary, such approach was delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. No "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, *J. Pharm. Sci*, 67, No. 5, 685 (1978). See also Bodor, "Novel Approaches for the Design of Membrane Transport Properties of Drugs", in *Design of Biopharmaceutical Properties Through Prodrugs and Analogs*, Roche, E. B. (ed.), APhA Academy of Pharmaceutical Sciences, Washington, D.C., 98–135 (1976). Subsequent extension of this first approach to delivering a much larger quaternary salt, berberine, to the brain via its dihydropyridine prodrug form was, however, found to provide site-specific sustained delivery to the brain of that anticancer agent. See Bodor et al, *Science*, Vol. 214, Dec. 18, 1981, pp. 1370–1372.

The second approach for delivering drugs to the brain using the redox system involves the use of a pyridinium carrier chemically linked to a biologically active compound. Bodor et al, *Science*, Vol. 214, Dec. 18, 1981, pp. 1370–1372, outline a scheme for this specific and sustained delivery of drug species to the brain, as depicted in the following Scheme I:

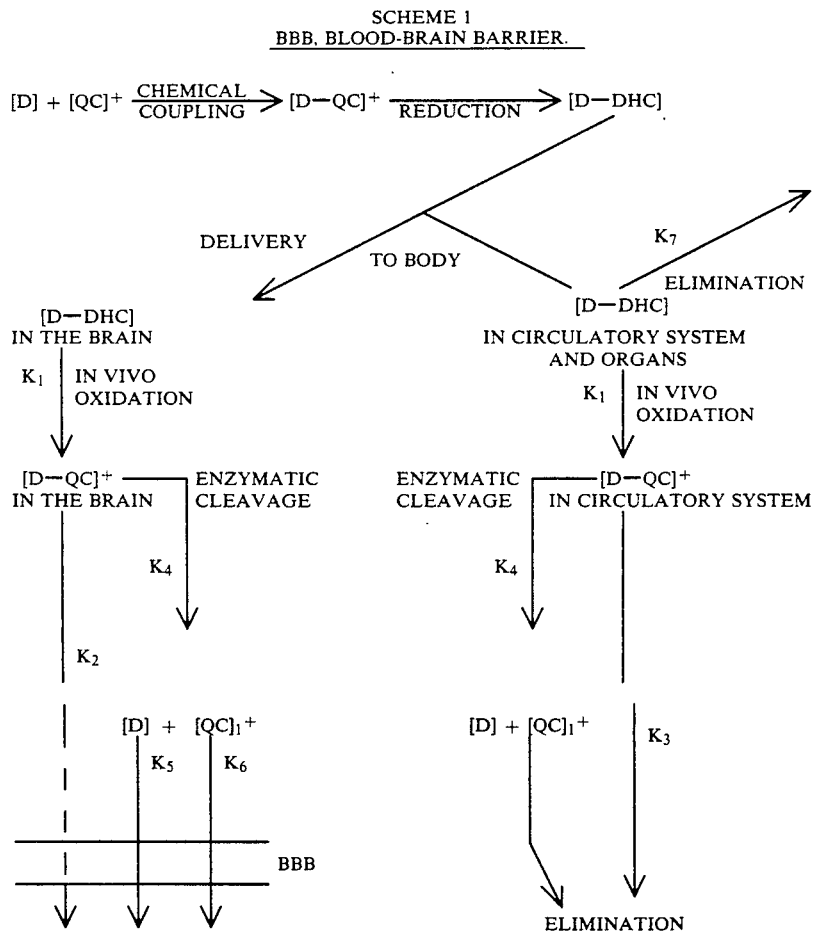

According to the scheme in *Science*, a drug [D] is coupled to a quaternary carrier [QC]+ and the [D-QC]+ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD⇌NADH system) to the ideally inactive original [D-QC]+ quaternary salt which, because of its ionic, hydrophilic character, should be rapidly eliminated from the general circulation of the body, while the blood-brain barrier should prevent its elimination from the brain ($k_3 >> k_2$; $k_3 >> k_7$). Enzymatic cleavage of the [D-QC]$^+$ that is "locked" in the brain effects a sustained delivery of the drug species [D], followed by its normal elimination ($k_5$), metabolism. A properly selected carrier [QC]$^+$ will also be rapidly eliminated from the brain ($k_6 >> k_2$). Because of the facile elimination of [D-QC]$^+$ from the general circulation, only minor amounts of drug are released in the body [$k_3 >> k_4$]; [D] will be released primarily in the brain ($k_4 > k_2$). The overall result ideally will be a brain-specific sustained release of the target drug species. Specifically, Bodor et al worked with phenylethylamine as the drug model. That compound was coupled to nicotinic acid, the quaternized to give compounds of the formula

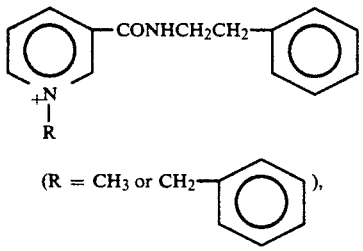

which were subsequently reduced by sodium dithionite to the corresponding compounds of the formula

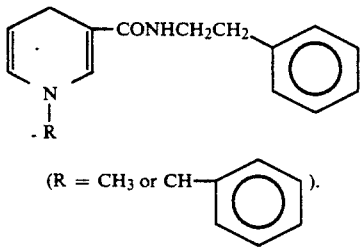

Testing of the N-methyl derivative in vivo supported the criteria set forth in Scheme I. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed. Other reports of this work with the redox carrier system have appeared in *The Friday Evening Post*, Aug. 14, 1981, Health Center Communications, University of Florida, Gainesville, Fla.; *Chemical & Engineering News*, Dec. 21, 1981, pp. 24–25; and *Science News*, Jan. 2, 1982, Vol. 121, No. 1, page 7. More recently, the redox carrier system has been substantially extended in terms of possible carriers and drugs to be delivered. See International Patent Application No. PCT/US83/00725, filed May 12, 1983 and published Nov. 24, 1983 under International Publication No. WO83/03968. Also see Bodor et al, *Pharmacology and Therapeutics*, Vol. 19, No. 3, pp. 337–386 (1983); and Bodor U.S. Pat. No. 4,540,564, issued Sept. 10, 1985.

The third approach for delivering drugs to the brain using the redox system provides derivatives of centrally acting amines in which a primary, secondary or tertiary amine function has been replaced with a dihydropyridine/pyridinium salt redox system. These brain-specific analogs of centrally acting amines have been recently described in International Patent Application No. PCT/US85/00236, filed Feb. 15, 1985 and published Sept. 12, 1985 under International Publication No. WO85/03937. The dihydropyridine analogs are characterized by the structural formula

wherein D is the residue of a centrally acting primary, secondary or tertiary amine, and

is a radical of the formula

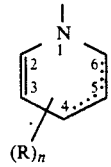 (a)

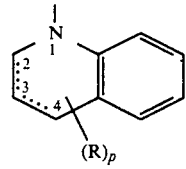 (b)

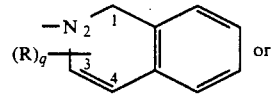 (c)

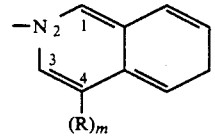 (d)

wherein the dotted line in formula (a) indicates the presence of a double bond in either the 4 or 5 position of the dihydropyridine ring; the dotted line in formula (b) indicates the presence of a double bond in either the 2 or 3 position of the dihydroquinoline ring system; m is zero or one; n is zero, one or two; p is zero, one or two, provided that when p is one or two, each R in formula (b) can be located on either of the two fused rings; q is zero, one, or two, provided that when q is one or two, each R in formula (c) can be located on either of the two fused rings; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl. These dihydropyridine analogs act as a delivery system for the corresponding biologically active quaternary compounds in vivo. Due to its lipophilic nature, the dihydropyridine analog will distribute throughout the body and has easy access to the brain through the blood-brain barrier. Oxidation in vivo will then provide the quaternary form, which will be "locked" preferentially in the brain. In contradistinction to the drug-carrier entities described in Bodor U.S. Pat. No. 4,540,564 and related publications, however, there is no readily metabolically cleavable bond between drug and quaternary portions, and the active species delivered is not the original drug from which the dihydro analog was derived, but rather is the quaternary analog itself.

Each of the major dihydropyridine⇌pyridinium redox systems for brain-targeted drug delivery thus has its own unique characteristics but also has properties in common with the other approaches. Common to the various approaches is introduction of a dihydropyridine-type nucleus into the drug molecule, which renders the dihydropyridine-containing drug derivative substantially more lipophilic than the parent drug from which it is derived. The increased lipophilicity enables the derivative to readily penetrate biological membranes, including the blood-brain barrier. Also common to the various approaches is the fact that the "redox" nature of the dihydropyridine-type moiety means that the lipophilic dihydropyridine form is oxidizable in vivo to the hydrophilic, ionic pyridinium salt form, thus locking in the brain either the active drug or the quaternary precursor, depending on which approach is employed.

The dihydropyridine⇌pyridinium salt redox carrier and analog systems have achieved remarkable success in targeting drugs to the brain in laboratory tests. This success is, of course, due in part to the highly lipophilic nature of the dihydropyridine-containing derivatives, which allows brain penetration. At the same time, the increased lipophilicity makes it practically impossible to formulate aqueous solutions of these derivatives for injection; moreover, even when the dihydropyridines are dissolved in organic solvents such as dimethylsulfoxide, they have a propensity for precipitating out of solution upon injection, particularly at higher concentrations, and especially at the injection site or in the lungs. Indeed, even in the absence of noticeable crystallization, it has been found that the redox derivatives frequently display not only the desired concentration in the brain but undesired lung concentrations as well, so that while the brain to blood ratios are at appropriate high levels, the initial lung to brain levels are high as well. Still further, the dihydropyridine-containing derivatives suffer from stability problems, since even in the dry state they are very sensitive to oxidation as well as to water addition. These problems, which must be overcome so that the dihydropyridine⇌pyridinium salt redox systems can be fully commercialized, have been addressed by applicant's copending application Ser. Nos. 07/139,755, 07/174,945 and 07/431,222 and are also addressed by the present application. In particular, the present application addresses the problems related to unfavorable concentration/precipitation of the dihydropyridine⇌pyridinium salt redox systems at or near the injection site and/or in the lungs, following parenteral administration, as well as similar problems encountered with other drugs which are insoluble, sparingly soluble and/or unstable in water.

Applicant's parent U.S. Pat. application Ser. No. 07/139,755, filed Dec. 30, 1987, incorporated by reference herein, relates to a method for stabilizing the reduced, dihydropyridine forms of dihydropyridine⇌pyridinium salt redox systems for brain-targeted drug delivery by forming inclusion complexes of the dihydropyridine forms with HPCD. The redox inclusion complexes also provide a means for increasing the ratio of initial brain to lung concentrations, thus leading to decreased toxicity, and in selected instances provide improved water solubility as well. Formulation of a particular redox system for estradiol "in a water-soluble β-hydroxycyclodextrin" is reported by Bodor and coworkers in Estes et al, "Use of a Chemical Redox System for Brain Enhanced Delivery of Estradiol Decreases Prostate Weight", in *Biological Approaches to the Controlled Delivery of Drugs*, ed. R. L. Juliano, Annals of the New York Academy of Sciences, Volume 507, 1987, 334–336.

Applicant's parent U.S. patent application Ser. No. 07/174,945, filed Mar. 29, 1988, incorporated by reference herein, relates to a method for decreasing the incidence of precipitation of a lipophilic and/or water-labile drug (i.e. a drug which is insoluble or only sparingly soluble in water and/or which is unstable in water) occurring at or near the injection site and/or in the lungs or other organs following parenteral administration, said method comprising parenterally administering said drug in an aqueous solution containing from about 20% to about 50% hydroxypropyl-β-cyclodextrin.

Applicant's parent U.S. patent application Ser. No. 07/431,222, filed Nov. 3, 1989, incorporated by reference herein, relates to a method for stabilizing the reduced, dihydropyridine forms of dihydropyridine⇌pyridinium salt redox systems for brain-targeted drug delivery by forming inclusion complexes of the dihydropyridine forms with cyclodextrin selected from the group consisting of hydroxypropyl, hydroxyethyl, glucosyl, maltosyl and maltotriosyl derivatives of β- and γ-cyclodextrin. The redox inclusion complexes also provides a means for increasing the ratio of brain to lung concentrations of drug at early time points, resulting in decreased toxicity. The redox inclusion complexes generally provide improved water solubility as well.

SUMMARY AND OBJECTS OF THE INVENTION

One object of the present invention is to provide improved aqueous parenteral solutions of drugs which are insoluble, sparingly soluble and/or unstable in water.

Another object of the present invention is to provide a method for decreasing the tendency of lipophilic and/or water-instable drugs to precipitate at or near the injection site and/or in the lungs following parenteral drug administration.

Yet another object of the present invention is to provide improved aqueous parenteral solutions containing the reduced, dihydropyridine form of a dihydropyridine⇌pyridinium salt redox system for brain-targeted drug delivery.

Still another object of the present invention is to provide a method for decreasing the tendency of the reduced, dihydropyridine form of a dihydropyridine⇌pyridinium salt redox system for brain-targeted drug delivery to precipitate at or near the injection site and/or in the lungs following parenteral administration.

Another object of the present invention is to provide a method for decreasing the incidence of precipitation of lipophilic and/or water-instable drugs occurring at or near the injection site and/or in the lungs following parenteral drug administration.

The foregoing objects are achieved by means of aqueous parenteral solutions of drugs which are insoluble, sparingly soluble and/or unstable in water, said solutions comprising from about 20 to about 50% cyclodextrin selected from the group consisting of hydroxypropyl, hydroxyethyl, glucosyl, maltosyl and maltotriosyl derivatives of $\beta$- and $\gamma$-cyclodextrin.

The invention thus provides a novel method for decreasing the tendency of lipophilic and/or water-unstable drugs to precipitate at or near the injection site and/or in the lungs or other organs following parenteral drug administration, said method comprising formulating said drug in an aqueous solution adapted for parenteral administration containing from about 20% to about 50% cyclodextrin selected from the group consisting of hydroxypropyl, hydroxyethyl, glucosyl, maltosyl and maltotriosyl derivatives of $\beta$- and $\gamma$-cyclodextrin. In one aspect of the invention, the drug is the reduced, biooxidizable, blood-brain barrier penetrating lipoidal form of a dihydropyridine$\rightleftarrows$pyridinium salt redox system for brain-targeted drug delivery.

The invention further provides a novel method for decreasing the incidence of precipitation of lipophilic and/or water-unstable drugs occurring at or near the injection site and/or in the lungs or other organs following parenteral administration, said method comprising parenterally administering said drug in an aqueous solution containing from about 20% to about 50% cyclodextrin selected from the group consisting of hydroxypropyl, hydroxyethyl, glucosyl, maltosyl and maltotriosyl derivatives of $\beta$- and $\gamma$-cyclodextrin. In a preferred aspect of the invention, the drug is the reduced, biooxidizable, blood-brain barrier penetrating lipoidal form of a dihydropyridine$\rightleftarrows$pyridinium salt redox system for brain-targeted drug delivery.

BRIEF DESCRIPTION OF THE DRAWINGS

Other objects and advantages of the present invention will be apparent from the following detailed description and accompanying drawings, in which.

DETAILED DESCRIPTION OF THE INVENTION

Figure 1B:
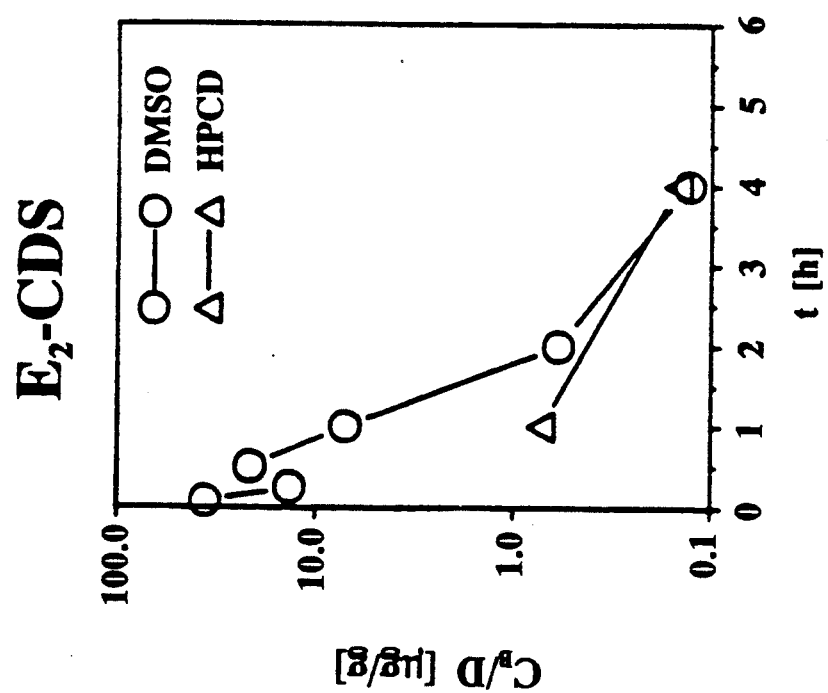
FIGS. 1a and 1b are a pair of semi-logarithmic plots, FIG. 1a comparing the concentrations of an estradiol-CDS, 17$\beta$-[(1-methyl-1,4-dihydro-3-pyridinyl)carbonyloxy]estra-1,3,5(10)-trien-3-ol, hereafter referred to as E$_2$-CDS, in lung tissue in $\mu$g per gram dose following systemic administration to rats of either 15 mg/kg E$_2$-CDS in dimethylsulfoxide (O) or 5 mg/kg E$_2$-CDS inclusion complex with hydroxypropyl-$\beta$-cyclodextrin ($\Delta$) in water, corrected for dose, and FIG. 1b comparing the lung concentrations of the quaternary cation, 17$\beta$-[(1-methyl-3-pyridinium)carbonyloxy]estra-1,3,5(10)-trien-3-ol, hereafter referred to as E$_2$Q$^+$ or Quat, following the same E$_2$-CDS administration.

The term "lipophilic" is used herein to describe drugs which are lipid-soluble and hydrophobic, i.e. which are insoluble or sparingly soluble in water.

The expression "parenteral" as used herein refers to routes of administration other than through the gastrointestinal tract or lungs, and to formulations for use in administering drugs by such routes. Thus, "parenteral" as used herein includes, for example, intramuscular, subcutaneous, intra-articular (i.e. into the joint, which in turn includes intra-synovial, i.e. into the synovial fluid) and, especially, intravenous routes and formulations. The words "parenteral" and "injectable" are used interchangeably herein.

Numerous drugs suffer from problems associated with their lack of water solubility and/or lack of stability in water. These lipophilic and/or water-labile drugs cannot be practically formulated as aqueous parenteral solutions. Consequently, the drugs are either unavailable for injection at the present time, or they are available for injectable use only in combination with undesirable organic vehicles. Injection of such vehicles is undesirable because of the systemic and local toxicity which can result. Some of the organic solvents commonly used as vehicles include dimethylacetamide (DMA), dimethylsulfoxide (DMSO), propylene glycol (PG), benzyl alcohol and ethanol. Examples of the toxicity associated with these solvents include central nervous system depression, nystagmus, lymphocytosis, liver and kidney damage, blood disorders, jaundice, weight loss, anemia, convulsions, hallucinations, mutagenic effects, cyanosis, hypotension, bronchial spasms, cardiac standstill and death.

Moreover, parenteral administration of lipophilic or water-labile drugs in organic vehicles can result in precipitation of the drug at and/or near the injection site and/or in the lungs or other organs, which in turn leads to increased toxicity. Precipitation of drugs in the lungs, for example, has led to severe respiratory distress and even death in laboratory animals. On the other hand, when lack of a suitable solvent results in the fact that the drug is only available as an oral formulation, then bioavailability becomes a concern since drugs are frequently less bioavailable from oral delivery forms than they are from parenteral, especially intravenous, forms.

Among the lipophilic and/or water-labile drugs which are contemplated for use in aqueous parenteral formulations in accord with the present invention, there can be mentioned antineoplastics (anticancer/antitumor agents), sedatives, anti-inflammatory steroids, tranquilizers, anticonvulsants, antivirals, vitamins/nutritional factors, emetics, anticoagulants, cardiotonics (including cardiac glycosides), diuretics, non-steroidal anti-inflammatory agents (NSAID's), androgens, estrogens, vasodilators, antidepressants, hypnotics, antifungals, progestins, antiprotozoals, anesthetics, vasoconstrictors, hypoglycemics, antibacterials/antibiotics, platelet inhibitors, muscle relaxants, antiemetics, radiodiagnostics, antispasmodics, antiarrhythmics, carbonic anhydrase inhibitors, narcotic antagonists, narcotic agonists, mixed narcotic agonists-antagonists, pharmacologically active proteins such as peptide hormones, enzymes, antibodies and other biologically produced substances, anti-Parkinsonism/dopamineric agents and drugs for treating Alzheimer's disease.

Specific drugs contemplated for parenteral formulation with hydroxypropyl-β-cyclodextrin in accord with the present invention include antineoplastics such as chlorambucil, lomustine, melphalan, methotrexate, hexamethylmelamine, teniposide, etoposide, semustine (methyl CCNU), fazarabine (Ara-AC), mercaptopurine, tubulazole, carmofur, carmustine, amsacrine, bruceantin, diaziquone, didemnin B, echinomycin and PCNU; anti-inflammatory steroids such as dexamethasone, hydrocortisone and prednisolone; estrogens such as 17β-estradiol, 17β-ethynylestradiol, ethynylestradiol 3-methyl ether and estriol; progestins such as norethindrone, norethindrone acetate, norgestrel, ethisterone, medroxyprogesterone acetate and progesterone; anticonvulsants such as phenytoin (diphenylhydantoin); barbiturates such as pentobarbital, phenobarbital and secobarbital, variously useful as hypnotics, anticonvulsants and sedatives; antivirals such as vidarabine; vitamins/nutritional factors such as retinol (vitamin A), vitamin A-acetate, cholecalciferol and retinal, as well as other fat-soluble vitamins such as the E, D and K vitamins; emetics such as apomorphine; diuretics such as chlorthalidone, furosemide and spironolactone; anticoagulants such as dicumarol; cardiotonics such as digoxin and digitoxin; non-steroidal anti-inflammatory agents such as indomethacin, piroxicam and flurbiprofen; androgens such as 17-methyltestosterone and testosterone; steroidal hypnotics/anesthetics such as alfaxalone; antidepressants such as sulpiride; antibiotics such as ampicillin and penicillin G; coronary vasodilators such as nitroglycerin and flunarizine; hypnotics such as etomidate; carbonic anhydrase inhibitors such as acetazolamide; antifungals such as ketoconazole, itraconazole, metronidazole benzoate and miconazole; antiprotozoals such as flubendazole; anesthetics such as lidocaine; hypoglycemics such as acetohexamide; anti-emetics such as dimenhydrinate; antibacterials such as co-trimoxazole; dopaminergic agents such as L-DOPA; anti-Alzheimer's agents such as THA; benzodiazepines, for example chlordiazepoxide, diazepam, medazepam, oxazepam and lorazepam, variously useful as sedatives, hypnotics, anticonvulsants, tranquilizers and muscle relaxants; and prostaglandins, for example PGE's such as $PGE_1$ (alprostadil), a vasodilator, and $PGI_2$ (prostacyclin or epoprostenol), a platelet inhibitor.

In one particularly preferred embodiment of the present invention, the drug contemplated for use in the instant parenteral formulations is an antineoplastic. Antineoplastics such as chlorambucil, lomustine, melphalan, hexamethylmelamine, methotrexate, semustine, teniposide, etoposide and fazarabine are particularly preferred.

In another preferred embodiment of the invention, the drug contemplated for use in the instant parenteral formulations is the steroidal anesthetic/hypnotic, alfaxalone.

In yet another preferred embodiment of the invention, the drug contemplated for use in the instant parenteral formulations is the reduced, dihydropyridine form of a dihydropyridine⇌pyridinium salt redox system for brain-targeted drug delivery.

With respect to the redox system for brain-targeted drug delivery, the following definitions are applicable:

The term "lipoidal" is intended to designate a redox moiety which is lipid-soluble or lipophilic.

The terms "redox carrier system" and "redox analog system" are intended to designate two different approaches to targeting drugs to the brain using a dihydropyridine⇌pyridinium salt system; compounds representing either of these approaches are contemplated for use with cyclodextrin selected from the group consisting of hydroxypropyl, hydroxyethyl, glucosyl, maltosyl and maltotriosyl derivatives of β- and γ-cyclodextrin (especially hydroxypropyl-β-cyclodextrin).

The redox carrier system provides for brain-targeted drug delivery by means of carrier-drugs, which in their reduced form, which is the form intended for administration, can be represented by the formula

[D-DHC]

wherein [D] is a centrally acting drug species and [DHC] is the reduced, biooxidizable, blood-brain barrier penetrating, lipoidal form of a dihydropyridine⇌pyridinium salt redox carrier. In their oxidized form, which is the form "locked" in the brain from which the active drug is ultimately released, the carrier-drugs can be represented by the formula $[D-QC]^+ X^-$ wherein $X^-$ is the anion of a non-toxic pharmaceutically acceptable acid, [D] is a centrally acting drug species and $[QC]^+$ is the hydrophilic, ionic pyridinium salt form of a dihydropyridine⇌pyridinium salt redox carrier. The redox carrier approach is discussed hereinabove in the section entitled "BACKGROUND OF THE INVENTION"; historically, the carrier system is the second type of redox system developed for delivering drugs to the brain.

Various aspects of the redox carrier system have been described in detail in Bodor U.S. Pat. Nos. 4,479,932, issued Oct. 30, 1984; Bodor 4,540,564, issued Sept. 10, 1985; Bodor et al 4,617,298, issued Oct. 14, 1986; UNIVERSITY OF FLORIDA's International Application No. PCT/US83/00725, published under International Publication No. WO83/03968 on Nov. 24, 1983; Bodor 4,727,079, issued Feb. 23, 1988; Bodor 4,824,850, issued Apr. 25, 1989; Bodor 4,829,070, issued May 9, 1989; and related publications. All of said patents and the international publication are incorporated by reference herein in their entirety and relied upon.

The redox analog system provides for brain-targeted drug delivery by means of new compounds containing a dihydropyridine⇌pyridinium salt portion which, unlike the redox carrier, is not readily metabolically cleavable from the original drug molecule.

One redox analog approach, which provides derivatives of centrally acting amines in which a primary, secondary or tertiary amine function has been replaced with a dihydropyridine⇌pyridinium salt redox system, is discussed hereinabove in the section entitled "BACKGROUND OF THE INVENTION"; historically, this analog system is the third type of redox system developed for delivering drugs to the brain. Various aspects of this analog system are described in detail in UNIVERSITY OF FLORIDA's International Application No. PCT/US85/00236, published under International Publication No. WO85/03937 on Sept. 12, 1985, incorporated by reference herein in its entirety and relied upon.

Another redox analog approach provides novel amino acids and peptides containing them which comprise a dihydropyridine⇌pyridinium salt portion, the redox system being appended directly or via an alkylene bridge to the carbon atom adjacent to the carboxyl carbon. These amino acids and peptides are described in detail in copending Bodor patent application Ser. No. 07/035,648, filed Apr. 7, 1987, now U.S. Pat. No. 4,888,427, incorporated by reference herein in its entirety and relied upon. Briefly, the novel redox amino acids in the reduced form have the structural formula

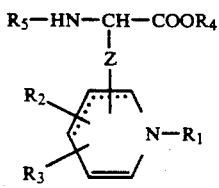

wherein Z is either a direct bond or $C_1$-$C_6$ alkylene and can be attached to the heterocyclic ring via a ring carbon atom or via the ring nitrogen atom; $R_1$ is $C_1$-$C_7$ alkyl, $C_1$-$C_7$ haloalkyl or $C_7$-$C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which can be the same or different, are each hydrogen or $C_1$-$C_7$ alkyl; or one of $R_2$ and $R_3$ together with the adjacent ring carbon atom forms a benzene ring fused to the heterocyclic ring, which benzene ring may optionally bear one or two substituents, which can be the same or different, selected from the group consisting of hydroxy, protected hydroxy, halo, cyano, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is hydrogen or $C_1$-$C_7$ alkyl, and —CONR'R'' wherein R' and R'', which can be the same or different, are each hydrogen or $C_1$-$C_7$ alkyl; $R_4$ is hydrogen or a carboxyl protective group; $R_5$ is hydrogen or an amino protective group; and the dotted lines indicate that the compound contains a 1,4- or 1,6-dihydropyridine, a 1,4- or 1,2-dihydroquinoline, or a 1,2-dihydroisoquinoline ring system.

The new dihydropyridine amino acid analogs depicted above and the corresponding oxidized forms are useful in the preparation of novel redox peptides of the partial formulas:

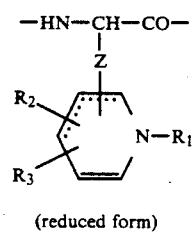

(reduced form)

and

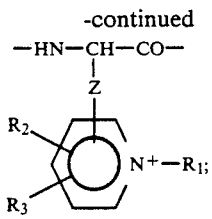

(oxidized form)

the new peptide analogs of partial structure (A) act as a delivery system for the corresponding quaternary salts of partial structure (B) in vivo; the quaternary derivatives, which also are chemical intermediates to the dihydro compounds, are pharmacologically active or convertible in vivo to pharmacologically active peptides, and are characterized by site-specific and sustained delivery to the brain when administered via the corresponding dihydropyridine form. Methods for the preparation of these analog amino acids and peptides utilize methods known in the art for introduction of the dihydropyridine⇌pyridinium salt moiety or a precursor thereof, e.g. from the aforementioned International Publications Nos. WO83/03968 and WO85/03937, appropriately combined with well-known methods for peptide synthesis. Ultimately, the quaternary forms of the amino acids and peptides are subjected to reduction to afford the corresponding dihydropyridines, according to the methods of the Bodor U.S. patents and above-mentioned published PCT applications.

In a preferred aspect of the present invention, the redox system selected for use with a hydroxypropyl, hydroxyethyl, glucosyl, maltosyl or maltotriosyl derivative of β- or γ-cyclodextrin in accord with the present invention is a redox carrier system. The drug and carrier portions of the redox carrier system are described in more detail below and of course in the various carrier patents and patent applications identified above and incorporated by reference herein. Selection of appropriate drugs and carrier moieties need not be limited to specific drugs and specific carriers disclosed in the aforementioned patents and applications or in the present application, just so long as the selected drug and carrier meet the general requirements of the drug/carrier system as described in the aforenoted documents.

The term "drug" as used herein means any substance intended for use in the diagnosis, cure, mitigation, treatment or prevention of disease or in the enhancement of desirable physical or mental development and conditions in man or animal.

By "centrally acting" drug species, active agent or compound as utilized herein, there is of course intended any drug species or the like, a significant (usually, principal) pharmacological activity of which is CNS and a result of direct action in the brain.

Exemplary such centrally acting drug species are the CNS-amines and other nervous system agents, whether sympathetic or parasympathetic, e.g., phenylethylamine (a stimulant), dopamine (a neurotransmitter and dopaminergic agent used, e.g., in the treatment of Parkinsonism or hyperprolactinemia), tyramine (a stimulant), L-DOPA (a dopamine precursor used, for example, in the treatment of Parkinsonism); muscle relaxants, tranquilizers and antidepressants, e.g., benzodiazepine tranquilizers such as diazepam and oxazepam and phenothiazine tranquilizers such as carphenazine, fluphenazine and the like; mild and strong analgesics and narcotics;

sedatives and hypnotics; narcotic antagonists; vascular agents; stimulants; anesthetics; small peptides, such as the di-, tri-, tetra and pentapeptides, and other small 2-20 amino acid unit containing peptides, e.g. the enkephalins (for example, Tyr-Gly-Gly-Phe-Leu), which, besides being analgesics, initiate epileptic activity in the brain at doses that are about tenfold lower than for effecting analgesic activity; growth-promoting substances; antiepileptic and anticonvulsant drugs generally, including hydantoins such as phenytoin and ethotoin, barbiturates such as phenobarbital; hormones, such as the steroid hormones, e.g., estradiol, testosterone, 17 α-ethynyl testosterone (ethisterone), and the like (recent studies on histological mapping of hormone-sensitive and specific steroid binding cells in the brain have underscored the importance of the steroid action in the brain on sexual behavior); amphetamine-like drugs; anticancer and anti-Parkinsonism agents; anti-hypertensives, agents to enhance learning capacity and the memory processes, including treatment of dementias, such as Alzheimer's disease, such as 9-amino-1,2,3,4-tetrahydroacridine; antibacterials; centrally acting hypotensive agents; centrally acting prostaglandins, such as $PGD_2$; diagnostic agents, such as radiopharmaceuticals; monoamine oxidase (MAO) inhibitor drugs; CNS or brain important/essential amino acids, such as tryptophan (which is an antidepressant as well as a nutrient); and any like centrally acting compounds. For the purposes of this invention, dopa or L-DOPA is not classified as an amino acid but rather as a CNS amine and dopaminergic agent used, e.g. in the treatment of Parkinsonism.

Other illustrative ultimate species of centrally acting drug entities are: amphetamine, dextroamphetamine, levamphetamine, aletamine, cypenamine, fencamfamin, fenozolone, zylofuramine, methamphetamine, phenmetrazine and phentermine, which are sympathomimetic amines/cerebral stimulants and appetite suppressants; etryptamine, a cerebral stimulant; codeine, oxycodone, pentazocine, anileridine, hydromorphone, morphine and oxymorphone, which are narcotic analgesics; desipramine, nortriptyline, octriptyline, maprotiline, opipramol and protriptyline, which are cerebral stimulants/tricylic antidepressants of the dibenzazepine type used, e.g., in endogenous depressions; clonidine and methyldopa, which are sympatholytic agents used, e.g., in hypertension; biperiden, cycrimine and procyclidine, which are centrally acting anticholinergics; tranylcypromine, a sympathomimetic cerebral stimulant/MAO inhibitor and antidepressant; acetophenazine, carphenazine, fluphenazine, perphenazine and piperacetazine, which are phenothiazine-type tranquilizers; benzoctamine, a sedative/muscle relaxant which structurally is an analogue of the phenothiazine tranquilizers; chlordiazepoxide, clorazepate, nitrazepam and temazepam, which are benzodiazepine-type tranquilizers; noracymethadol, a narcotic analgesic of the methadone type; piminodine, a narcotic analgesic of the meperidine type; tracazolate, a sedative/hypotensive; prizidilol, a centrally acting hypotensive; sulpiride, an antidepressant/psychotropic; haloperidol and clopenthixol, which are tranquilizers; norepinephrine, a sympathetic stimulant/adrenergic agent; nalorphine and naloxone, narcotic antagonists; hydralazine, a hypotensive; ethotoin, phenobarbital and aminoglutethimide, anticonvulsants; epinephrine, an adrenergic agent; ethamivan, a medullary stimulant; bemegride, a barbiturate antagonist; amiphenazole, a stimulant; iopydol, iodopyracet, iodouppurate (o-iodohippuric acid), iodamide and iopanoic acid, which are radiodiagnostics; ephedrine, pseudoephedrine, oxymetazoline and phenylephrine, which are sympathomimetic amines and decongestants; estradiol, estrone and estriol, the natural estrogens; amoxicillin, oxacillin, carbenicillin, benzylpenicillin, phenoxymethylpenicillin, methicillin, nafcillin, ticarcillin, bacampicillin, epicillin, hetacillin, pivampacillin, the methoxymethyl ester of hetacillin, and ampicillin, which are penicillin-type antibiotics; amobarbital, a sedative; trihexyphenidyl, a centrally acting anticholinergic; hydroxyzine, a tranquilizer; chlortetracycline, demeclocycline, minocycline, doxycycline, oxytetracycline, tetracycline and methacycline, which are tetracycline-type antibiotics; flurazepam, bromazepam, demoxepam and lorazepam, benzodiazepine tranquilizers; phenytoin, an anticonvulsant; glutethimide, a mild hypnotic/sedative; clindamycin, lincomycin, nalidixic acid, oxolinic acid and phenazopyridine, antibacterials/antibiotics; bethanidine and guanethidine, hypotensives/sympatholytics; captopril, a hypotensive; methyprylon, a mild hypnotic; amedalin, bupropion, cartazolate, daledalin, difluanine, fluoxetine and nisoxetine, which are cerebral stimulants; propranolol, a β-blocker antihypertensive; cloxacillin and dicloxacillin, penicillin-type antibacterials; butalbital, a barbiturate sedative; GABA, γ-vinyl GABA, γ-acetylenic GABA, neurotransmitters for possible use in epilepsy; valproic acid and its metabolites such as 5-hydroxy-2-n-propylpentanoic acid, 4-hydroxy-2-n-propylpentanoic acid, 3-hydroxy-2-n-propylpentanoic acid, for use as anticonvulsants; valpromide, a valproic acid derivative for use as an anticonvulsant; apomorphine, a narcotic depressant/emetic which has been used in the treatment of photosensitive epilepsy; pholcodine, a narcotic antitussive; methotrexate, mitoxantrone, podophyllotoxin derivatives (etopside, teniposide), doxorubicin, daunamycin and cyclophosphamide, anti-cancer/antitumor agents; methylphenidate, a stimulant; thiopental, an anesthetic; ethinyl estradiol and mestranol, estrogens; meptazinol, cyclazocine, phenazocine, profadol, metopon, drocode and myfadol, which are narcotic analgesics; buprenorphine, nalbuphine, butorphanol, levallorphan, naltrexone, nalmefene, alazocine, oxilorphan and nalmexone, which are narcotic antagonists or agonist-antagonists; norgestrel and norethindrone, progestins; cephalothin, cephalexin, cefazolin, cefoxitin, moxalactam, ceforanide, cefroxadine and cephapirin, cephalosporin antibiotics; atenolol, nadolol, timolol and metoprolol, β-blockers/hypotensives; ACTH (corticotropin), a hormone which stimulates glucocorticoid production; LHRH, a neurotransmitter which stimulates secretion of the pituitary hormones, LH and FSH, and has been used to induce ovulation as well as for fertility control/contraception; sulfadiazine and other sulfonamide antibiotics; ribavirin and acyclovir, antiviral agents; chlorambucil and melphalan, nitrogen mustard-type anticancer/antitumor agents; methotrexate and aminopterin, which are folic acid antagonist-type anticancer/antitumor agents; platinum coordination complexes, i.e. cisplatin analogue-type anticancer/antitumor agents; dactinomycin and mitomycin C, used in cancer chemotherapy; thioguanine, a purine/pyrimidine antagonist used in cancer treatment; vincristine and vinblastine, anticancer alkaloids; hydroxyurea and DON, anticancer urea derivatives; FSH, HCG and HCS, pituitary and nonpituitary gonadotropins, used, for example, in certain reproductive disorders; N,N'-bis(dichloracetyl)-1,8-octamethylenediamine (fertilysin), an agent for male fertility inhibition; levorphanol, a narcotic analgesic; benzestrol and diethylstilbestrol, synthetic estrogens; ethyl β-carboline-3-carboxylate, a benzodiazepine antagonist; furosemide, a diuretic/antihypertensive; dipyridamole and nifedipine, coronary vasodilators; and progabide, a GABA-agonist and prodrug of GABA. Yet other ultimate species include non-steroidal antiinflammatory agents/non-narcotic analgesics, e.g. propionic acid derivatives, acetic acid derivatives, fenamic acid derivatives and biphenylcarboxylic acid derivatives. Specific NSAID's/non-narcotic analgesics contemplated for combination with the redox carrier include ibuprofen, naproxen, flurbiprofen, zomepirac, sulindac, indomethacin, fenbufen, fenoprofen, indoproxen, ketoprofen, fluprofen, bucloxic acid, tolmetin, alclofenac, fenclozic acid, ibufenac, flufenisal, pirprofen, flufenamic acid, mefenamic acid, clonixeril, clonixin, meclofenamic acid, flunixin, diclofenac, carprofen, etodolac, fendosal, prodolic acid, sermetacin, indoxole, tetrydamine, diflunisal, naproxol, piroxicam, metazamide, flutiazin and tesicam.

Preferred classes of centrally acting drugs for combination with the redox carrier are the central neurotransmitters, steroids, anticancer and antitumor agents, antiviral agents, tranquilizers, memory enhancers, hypotensives, sedatives, antipsychotics and cerebral stimulants (especially tricyclic antidepressants). Among the neurotransmitters, there can be mentioned amino acids, such as GABA, GABA derivatives and other omega-amino acids, as well as glycine, glutamic acid, tyrosine, aspartic acid and other natural amino acids; catecholamines, such as dopamine, norepinephrine and epinephrine; serotonin, histamine and tryptamine; and peptides such as neurotensin, luteinizing hormone-releasing hormone (LHRH), somatostatin, enkephalins such as met$^5$-enkephalin and leu$^5$-enkephalin, endorphins such as γ, α- and β-endorphins, oxytocin M and vasopressin. Synthetic and semi-synthetic analogues, e.g. analogues of LHRH in which one or more amino acid(s) has/have been eliminated and/or replaced with one or more different amino acid(s), and which may be agonists or antagonists, are also contemplated, e.g. the primary and secondary amine LHRH analogues disclosed in U.S. Pat. Nos. 4,377,574, 3,917,825, 4,034,082 and 4,338,305. Among the steroids, there can be mentioned anti-inflammatory adrenal cortical steroids such as hydrocortisone, betamethasone, cortisone, dexamethasone, flumethasone, fluprednisolone, meprednisone, methyl prednisolone, prednisolone, prednisone, triamcinolone, cortodoxone, fludrocortisone, flurandrenolone acetonide (flurandrenolide), paramethasone and the like; male sex hormones (androgens), such as testosterone and its close analogues, e.g. methyl testosterone (17-methyltestosterone); and female sex hormones, both estrogens and progestins, e.g. progestins such as norgestrel, norethindrone, norethynodrel, ethisterone, dimethisterone, allylestrenol, cingestol, ethynerone, lynestrenol, norgesterone, norvinisterone, ethynodiol, oxogestone and tigestol, and estrogens such as ethinyl estradiol, mestranol, estradiol, estriol, estrone and quinestrol and the like. Among the anticancer and antitumor agents, there can be mentioned Ara-AC, pentostatin (2'-deoxycoformycin), Ara-C (cytarabine), 3-deazaguanine, dihydro-5-azacytidine, tiazofurin, sangivamycin, Ara-A (vitarabine), 6-MMPR, PCNU, FENU, HENU and other nitrosoureas, spiromustine, bisbenzimidazole, L-alanosine (6-diazo-5-oxo-L-norleucine), DON, L-ICRF, trimethyl TMM, 5-methyltetrahydrohomofolic acid, glyoxylic acid sulfonylhydrazone, DACH, SR-2555, SR-2508, desmethylmisonidazole, mitoxantrone, menogarol, aclacinomycin A, phyllanthoside, bactobolin, aphidocolin, homoharringtonine, levonantradol, acivicin, streptozotocin, hydroxyurea, chlorambucil, cyclophosphamide, uracil mustard, melphalan, 5-FU (5-fluorouracil), 5-FUDR (floxuridine), vincristine, vinblastine, cytosine arabinoside, 6-mercaptopurine, thioguanine, 5-azacytidine, methotrexate, adriamycin (doxorubicin), daunomycin (daunorubicin), largomycine polypeptide, aminopterin, dactinomycin, mitomycin C, and podophyllotoxin derivatives, such as etoposide (VP-16) and teniposide. Among the antiviral agents, there can be mentioned ribavirin; acyclovir (ACV); amantadine (also of possible value as an anti-Parkinsonism agent); diarylamidines such as 5-amidino-2-(5-amidino-2-benzofuranyl)indole and 4',6-diimidazolino-2-phenylbenzo(b)thiophene; 2-aminooxazoles such as 2-guanidino-4,5-di-n-propyloxazole and 2-guanidino-4,5-diphenyloxazole; benzimidazole analogues such as the syn and anti isomers of 6[[(hydroxyimino)phenyl]methyl]-1-[(1-methylethyl)-sulfonyl]-1H-benzimidazol-2-amine; bridgehead C-nucleosides such as 5,7-dimethyl-2-β-D-ribofuranosyl-s-triazole(1,5-a)pyrimidine; glycosides such as 2-deoxy-D-glucose, glucosamine, 2-deoxy-2-fluoro-D-mannose and 6-amino-6-deoxy-D-glucose; phenyl glucoside derivatives such as phenyl-6-chloro-6-deoxy-β-D-glucopyranoside; (S)-9-(2,3-dihydroxypropyl)adenine; tiazofurin; selenazofurin; 3-deazauridine; 3-deazaguanosine; DHPG; 6-azauridine; idoxuridine; trifluridine (trifluorothymidine); BDVU (bisdihydroxyvinyluridine); zidovudine (AZT); dideoxycytidine; and 5,6-dichloro-1-β-D-ribofuranosylbenzimidazole. Among the anticancer/antitumor and antiviral agents, those of the nucleoside type (i.e. a purine or pyrimidine base-type structure bearing a singly or multiply hydroxylated substituent) are of particular interest. This group includes such compounds as Ara-AC, pentostatin, Ara-C, dihydro-5-azacytidine, tiazofurin, sangivamycin, Ara-A, 6-MMPR, desmethylmisonidazole, 5-FUDR, cytosine arabinoside, 5-azacytidine, ribavirin, acyclovir, (S)-9-(2,3-dihydroxypropyl)adenine, 6-azauridine, 5,6-dichloro-1-β-D-ribofuranosylbenzimidazole, 5,7-dimethyl-2-β-D-ribofuranosyl-s-triazole(1,5-a)pyrimidine, zidovudine (AZT), dideoxycytidine, dideoxyadenosine, dideoxyinosine and DHPG. Among the tranquilizers, there can be mentioned benzodiazepine tranquilizers, such as diazepam, oxazepam, lorazepam, chlordiazepoxide, flurazepam, bromazepam, chlorazepate, nitrazepam and temazepam; hydantoin-type tranquilizers/anticonvulsants such as phenytoin, ethotoin, mephenytoin; phenothiazine-type tranquilizers such as acetophenazine, carphenazine, fluphenazine, perphenazine and piperacetazine; and others. Among the hypotensives, there can be mentioned clonidine, methyldopa, bethanidine, debrisoquin, hydralazine, and guanethidine and its analogues. Among the sedatives, tranquilizes and antipsychotics, there can be mentioned the many specific compounds of this type disclosed above, especially the phenothiazines and benzodiazepines and their analogues. Among the cerebral stimulants, there also can be mentioned the many specific compounds set forth hereinabove, particularly the sympathomimetic amine-type cerebral stimulants and the tricyclic antidepressants, especially preferred tricyclics being the dibenzazepines and their analogues.

Also illustrative of the centrally acting drug species contemplated for combination with the redox carrier are centrally active metabolites of centrally acting drugs. Such metabolites are typified by hydroxylated metabolites of tricyclic antidepressants, such as the E- and Z-isomers of 10-hydroxynortriptyline, 2-hydroxyimipramine, 2-hydroxydesipramine and 8-hydroxychloripramine; hydroxylated metabolites of phenothiazine tranquilizers, e.g. 7-hydroxychlorpromazine; and desmethyl metabolites of N-methyl benzodiazepine tranquilizers, e.g. desmethyldiazepam. Other CNS active metabolites for use herein will be apparent to those skilled in the art, e.g. SL 75102, which is an active metabolite of progabide, a GABA agonist, and hydroxy-CCNU, which is an active metabolite of CCNU, an anticancer nitrosourea. Typically, these CNS active metabolites have been identified as such in the scientific literature but have not been administered as drugs themselves. In many cases, the active metabolites are believed to be comparable in CNS activity to their parent drugs; frequently, however, the metabolites have not been administered per se because they are not themselves able to penetrate the blood-brain barrier.

As indicated hereinabove, diagnostic agents, including radiopharmaceuticals, are encompassed by the expression "centrally acting drug" or the like as used herein. Any diagnostic agent which can be derivatized to afford a redox carrier system which will penetrate the BBB and concentrate in the brain in its quaternary form and can be detected therein is included. The diagnostic may be "cold" and be detected by X-ray (e.g. radiopaque agents) or other means such as mass spectrophotometry, NMR or other non-invasive techniques (e.g. when the compound includes stable isotopes such as C13, N15, O18, S33 and S34). The diagnostic alternatively may be "hot", i.e. radiolabelled, such as with radioactive iodine (I 123, I 125, I 131) and detected/imaged by radiation detection/imaging means. Typical "cold" diagnostics for derivation herein include o-iodohippuric acid, iothalamic acid, iopydol, iodamide and iopanoic acid. Typical radiolabelled diagnostics include diohippuric acid (I 125, I 131), diotyrosine (I 125, I 131), o-iodohippuric acid (I 131), iothalamic acid (I 125, I 131), thyroxine (I 125, I 131), iotyrosine (I 131) and iodometaraminol (I 123), which has the structural formula

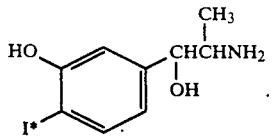

In the case of diagnostics, unlike the case of drugs which are for the treatment of disease, the "locked in" quaternary form will be the form that is imaged or otherwise detected, not the original diagnostic itself. Moreover, any of the centrally acting drugs which are intended for the treatment or prevention of medical disorders but which can be radiolabelled, e.g. with a radioisotope such as iodine, or labelled with a stable isotope, can thus be converted to a diagnostic for incorporation into the redox carrier system.

It will be apparent from the known structures of the many drug species exemplified above, that in many cases the selected drug will possess more than one reactive functional group, and, in particular, that the drug may contain hydroxyl or carboxyl or amino or other functional groups in addition to the groups to which the carrier will be linked, and that these additional groups will at times benefit from being protected during synthesis and/or during administration. The nature of such protection is described in more detail in the various patents and patent applications incorporated by reference herein. Obviously, such protected drug species are encompassed by the definition of "drug" set forth hereinabove.

It too will be appreciated that by "dihydropyridine carrier" or "[DHC]", there is intended any nontoxic carrier moiety comprising, containing or including the dihydropyridine nucleus, whether or not a part of any larger basic nucleus, and whether substituted or unsubstituted, the only criterion therefor being capacity for BBB penetration and in vivo oxidation thereof to the corresponding quaternary pyridinium salt carrier [QC]+. As aforesaid, the ionic pyridinium salt drug/carrier prodrug entity [D-QC]+ which results from such in vivo oxidation is prevented from efflux from the brain, while elimination from the general circulation is accelerated. Subsequently, the covalent or equivalent bond coupling the drug species [D] to the quaternary carrier [QC]+ is metabolically cleaved, which results in sustained delivery of the drug [D] in the brain and facile elimination of the carrier moiety [QC]+. Such "covalent or equivalent bond" between the drug and the quaternary carrier can be a simple direct chemical bond, e.g., an amide, an ester, or any other like bond, or same can even be comprised of a linking group or function, e.g., a thiazolidine bridge or a peptide linkage, typically necessitated when the drug species is not susceptible to direct chemical coupling to either the dihydropyridine carrier or the quaternary carrier. Nonetheless, the bond in the formulae [D-QC]+ and [D-DHC] is intended to be, and is hereby defined as inclusive of all such alternatives. And the cleavage of the [D-QC]+ prodrug to sustainedly deliver the drug species [D] in the brain with concomitant facile elimination of the carrier moiety [QC]+ is characteristically enzymatic cleavage, e.g., by esterase, amidase, cholinesterase, hydrolytic enzyme, or peptidase.

The expression "non-toxic pharmaceutically acceptable salts" as used herein generally includes the non-toxic salts of the reduced, dihydropyridine forms of the redox carrier or redox analog systems, formed with nontoxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a non-toxic pharmaceutically acceptable acid" as used herein, e.g. in connection with the oxidized, pyridinium salt forms of the redox carrier or redox analog systems, is intended to include anions of such inorganic or organic acids HX.

In the discussion to follow, the expression "at least one reactive functional group selected from the group consisting of amino, hydroxyl, mercapto, carboxyl, amide and imide" or portions of that expression are used. The functional groups designated in that expression have the following meanings:

The word "amino" means a primary or secondary amino function, i.e. —NH$_2$ or —NHR. The secondary amino function is also represented herein as —NH—, particularly since the exact identity of the R portion of —NHR is immaterial, R being a part of the drug residue D itself which is left unchanged by conversion of the drug to the redox carrier system.

The word "hydroxyl" means an —OH function.

The word "carboxyl" means a —COOH function.

The word "mercapto" means an —SH function.

The word "amide" means a carbamoyl (—CONH₂) or substituted carbamoyl (—CONHR) or a sulfamoyl (—SO₂NH₂) or substituted sulfamoyl (—SO₂NHR) functional group. The —CONHR and —SO₂NHR groups may also be represented herein as —CONH— and —SO₂NH—, respectively, since the identity of R is immaterial, R being a part of the drug residue D itself which is left unchanged by conversion of the drug to the redox carrier system.

The word "imide" means a functional group having the structure

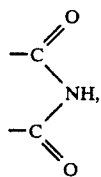

that is, the structure which characterizes imides (i.e. compounds having a succinimide-type or phthalimide-type structure).

Many different dihydropyridine⇌pyridinium salt redox carrier moieties are illustrated in the carrier patents and applications incorporated by reference hereinabove. The following is a list of representative major classes of dihydros and the corresponding quaternaries, but is not meant to be exhaustive:

(1) For linkage to a drug having at least one hydroxyl or mercapto or primary or secondary amino functional grouping, replacing a hydrogen atom from at least one of said functional groupings with one of the following [DHC] groupings:

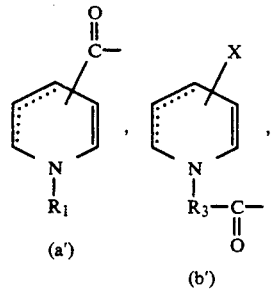

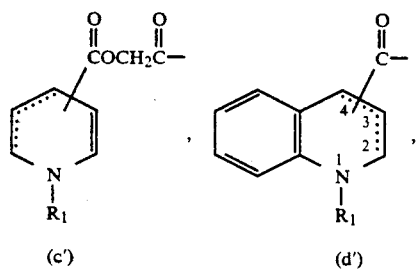

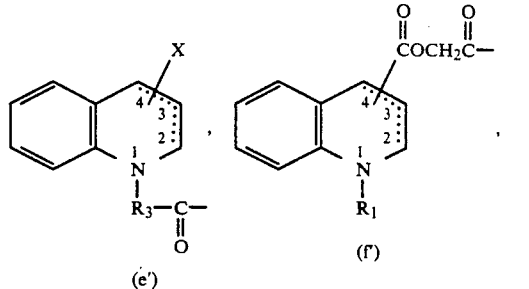

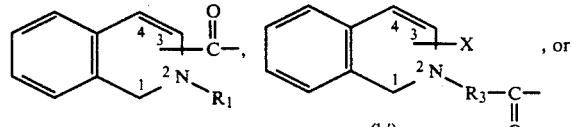

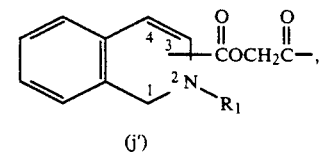

wherein the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$–$C_7$ alkyl, $C_1$–$C_7$ haloalkyl or $C_7$–$C_{10}$ aralkyl; $R_3$ is $C_1$ to $C_3$ alkylene; X is —CONR'R", wherein R' and R", which can be the same or different, are each H or $C_1$–$C_7$ alkyl, or X is —CH=NOR''' wherein R''' is H or $C_1$–$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at the 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring.

(2) For linkage to a drug having at least one carboxyl functional grouping, replacing a hydrogen atom from at least one of said carboxyl groupings with one of the following [DHC] groupings:

(a) When there are one or more —COOH groups to be derivatized:

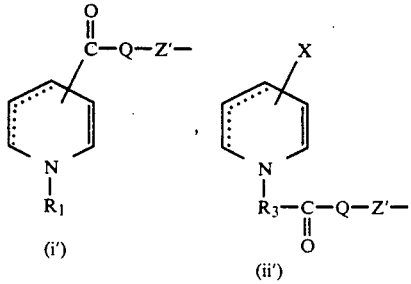

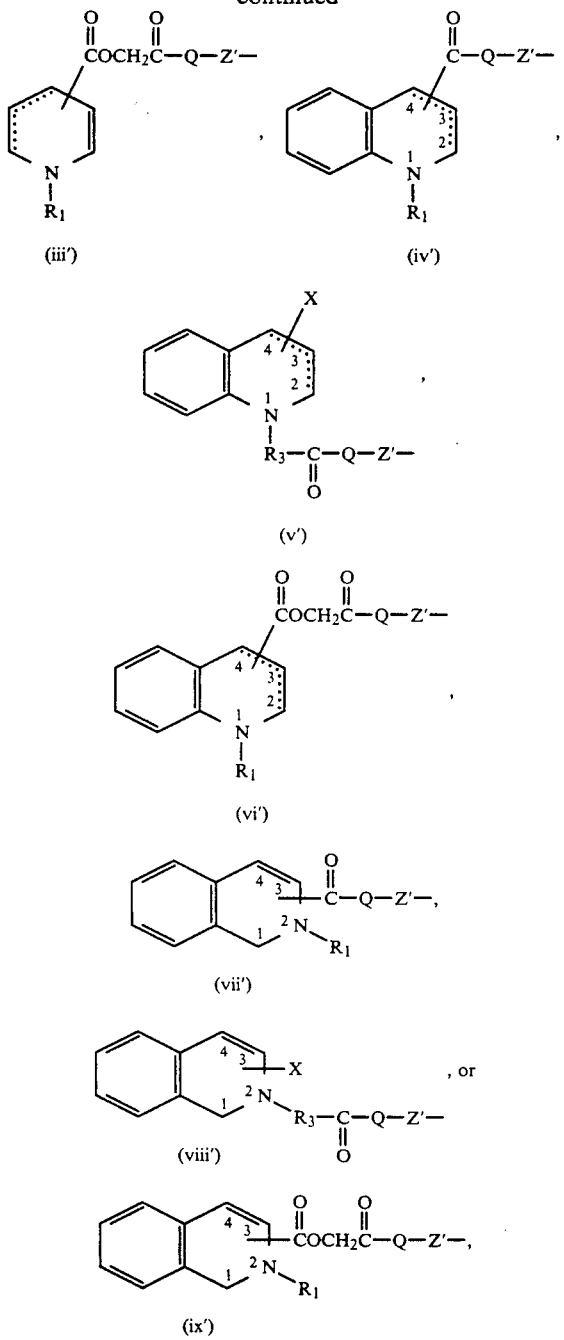

(iii')

(iv')

(v')

(vi')

(vii')

(viii')

(ix')

wherein the dotted line in formulas (i'), (ii') and (iii') indicates the presence of a double bond in either the 4 or 5 position of the dihydropyridine ring; the dotted line in formulas (iv'), (v') and (vi') indicates the presence of a double bond in either the 2 or 3 position of the dihydroquinoline ring; Z' is $C_1$–$C_8$ straight or branched alkylene, preferably $C_1$–$C_3$ straight or branched alkylene; Q is —O— or —NH—; $R_1$ is $C_1$–$C_7$ alkyl, $C_1$–$C_7$ haloalkyl or $C_7$–$C_{10}$ aralkyl; $R_3$ is $C_1$–$C_3$ alkylene; X is —CONR'R" wherein R' and R", which can be the same or different, are each H or $C_1$–$C_7$ alkyl, or X is —CH=NOR''' wherein R''' is H or $C_1$–$C_7$ alkyl; the X substituent in formula (ii') and the carbonyl-containing grouping in formulas (i') and (iii') can each be attached at the 2, 3 or 4 position of the dihydropyridine ring; the X substituent in formula (v') and the carbonyl-containing groupings in formulas (iv') and (vi') can each be attached at the 2, 3 or 4 position of the dihydroquinoline ring; and the X substituent in formula (viii') and the carbonyl-containing groupings in formulas (vii') and (ix') can each be attached at the 1, 3 or 4 position of the dihydroquinoline ring;

(b) Alternatively, when there is only one —COOH group to be derivatized:

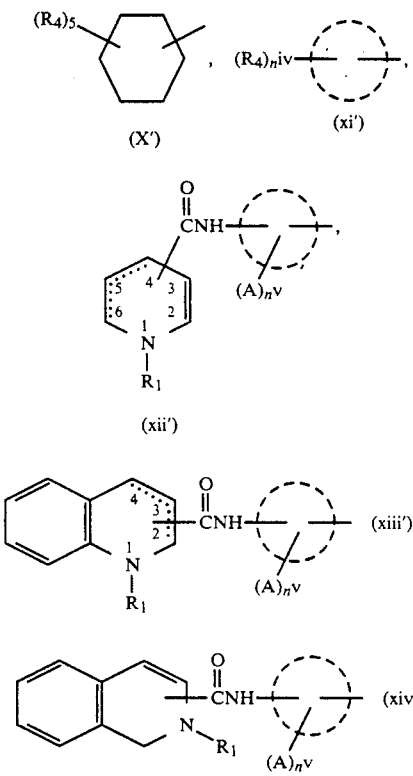

(X')

(xi')

(xii')

(xiii'), or (xiv'), wherein the dotted line in formula (xii') indicates the presence of a double bond in either the 4 or 5 position of the dihydropyridine ring; the dotted line in formula (xiii') indicates the presence of a double bond in either the 2 or 3 position of the dihydroquinoline ring; ⌒⌒ is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii'), (xiii') and (xiv') can independently be hydroxy or D', D' being the residue of a centrally acting drug containing one reactive carboxyl functional group, said residue being characterized by the absence of a hydrogen atom from said carboxyl functional group in said drug; and each $R_4$ in each of structures (x') and (xi') can independently be hydroxy,

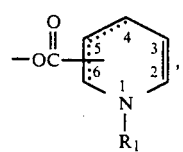

-continued

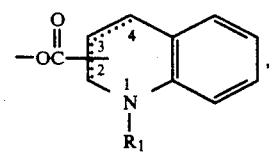

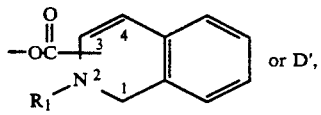
or D', wherein the dotted line is defined as with structures (xii') and (xiii'); D' is defined as with structures (xii'), (xiii') and (xiv'); $R_1$ is $C_1$-$C_7$ alkyl, $C_1$-$C_7$ haloalkyl or $C_7$-$C_{10}$ aralkyl; and the depicted carbonyl groupings can be attached at the 2, 3 or 4 position of the pyridinium or quinolinium ring or at the 1, 3 or 4 position of the isoquinolinium ring; with the proviso that at least one $R_4$ in each of structures (x') and (xi') is

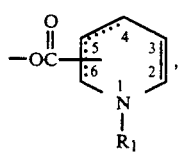

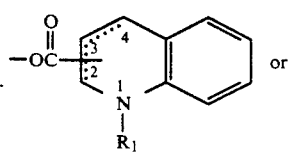
or

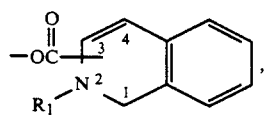

wherein $R_1$, the dotted lines and the position of the carbonyl-containing groupings are defined as above; and with the further proviso that when more than one of the $R_4$ radicals in a given compound are the aforesaid carbonyl-containing groupings, then all such carbonyl-containing groupings in said compound are identical.

(3) For linkage to a drug having at least one —NH— functional group which is part of an amide or imide structure or at least one low pKa primary or secondary amine functional group, replacing a hydrogen atom from at least one of said functional groupings with one of the following [DHC] groupings:

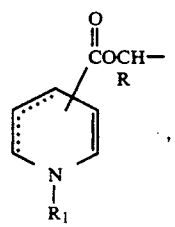 (k')

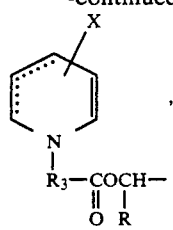 (l')

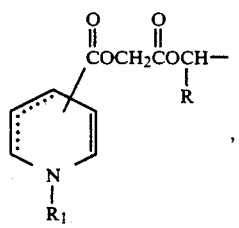 (m')

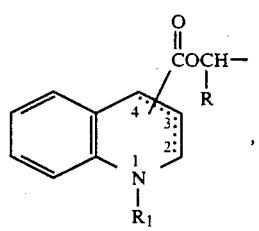 (n')

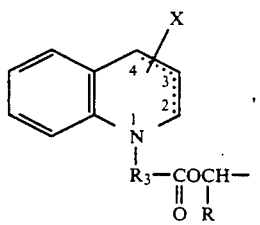 (o')

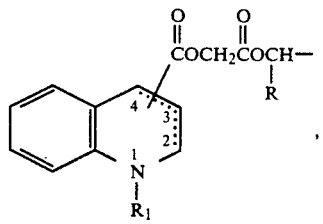 (p')

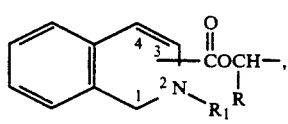 (q')

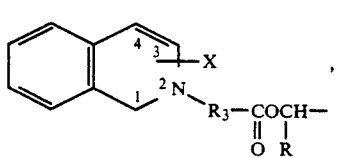 (r')

or

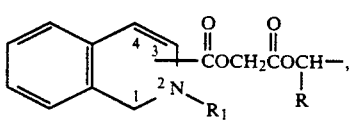 (s')

wherein R is hydrogen, $C_1$-$C_7$ alkyl, $C_3$-$C_8$ cycloalkyl, $C_1$-$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; the dotted line in formulas (k'), (l') and (m') indicates the presence of a double bond in either the 4 or 5 position of the dihydropyridine ring; the dotted line in formulas (n'), (o') and (p') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R", wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (k') and (m') and the X substituent in formula (l') can each be attached at the 2, 3 or 4 position of the dihydropyridine ring; the carbonyl-containing groupings in formulas (n') and (p') and the X substituent in formula (o') can each be attached at the 2, 3 or 4 position of the dihydroquinoline ring; and the carbonyl-containing groupings in formulas (q') and (s') and the X substituent in formula (r') can each be attached at the 1, 3 or 4 position of the dihydroisoquinoline ring.

Drugs containing secondary or tertiary hydroxyl functional groups can be linked to any of the [DHC] groupings (k') through (s') above in which the

portion is derived from an aldehyde $RCH_2O$ capable of reacting with said drug to form the corresponding hemiacetal, e.g. chloral, acetaldehyde, formaldehyde or benzaldehyde.

The following are especially preferred reduced, dihydropyridine forms of dihydropyridine⇌pyridinium salt redox carrier systems, also termed "chemical delivery systems" or "CDS", for brain-targeted drug delivery which are contemplated for use in parenteral formulations with the selected cyclodextrin in accord with the present invention:

| Structure | Chemical Name | Abbreviated Name | Synthesis | Pharmacological Use |
|---|---|---|---|---|
| [structure] | 1-methyl-3-{[N-{β-[3,4-bis(pivalyloxy)phenyl]ethyl}carbamoyl]}-1,4-dihydropyridine | dopamine-CDS₁ or DA-CDS | U.S. Pat. No. 4,540,564, Example 23 | dopaminergic agent (anti-hyperprolactinemia, anti-Parkinsonism) |
| [structure] | 1-methyl-3-{[N-{[β-[3,4-bis(isobutyryloxy)phenyl]ethyl]]}-carbamoyl-1,4-dihydropyridine | dopamine-CDS₂ | Example 4 hereinbelow | as dopamine-CDS₁ |
| [structure] | N-{β-[3,4-bis(pivalyloxy)phenyl]ethyl}aminocarbonyloxymethyl 1,4-dihydro-1-methyl-3-pyridine-carboxylate | dopamine-CDS₃ | Example 115 hereinbelow | as dopamine-CDS₁ |
| [structure] | 17β-[(1,4-dihydro-1-methyl-3-pyridinylcarbonyl)oxy]androst-4-en-3-one | testosterone-CDS₁ or T-CDS₁ | U.S. Pat. No. 4,479,932, Example 38 | androgenic agent |

| Structure | Chemical Name | Abbreviated Name | Synthesis | Pharmacological Use |
|---|---|---|---|---|
| (steroid structure with pyridine-CONH$_2$ ester) | 17β-{[(3''-carbamoyl-1',4'-dihydropyridinyl)acetyl]oxy}-androst-4-en-3-one | testosterone-CDS$_2$ or T-CDS$_2$ | Bodor et al, J. Pharm. Sci. (1987),75(1),29-35 | as testosterone-CDS$_1$ |
| (diphenyl imidazolidinedione with N-methyl dihydropyridine) | 5,5-diphenyl-3-[(1'-methyl-1',4'-dihydropyridin-3'-yl)carbonyloxymethyl]-2,4-imidazolidinedione | phenytoin-CDS$_1$ | Example 8 hereinbelow | anticonvulsant agent |
| (diphenyl imidazolidinedione with dihydropyridine-CONH$_2$) | 3-[(3'-carbamoyl-1',4'-dihydropyridin-1'-yl)acetyloxymethyl]-5,5-diphenyl-2,4-imidazolidinedione | phenytoin-CDS$_2$ | Example 15 hereinbelow | as phenytoin-CDS$_1$ |
| (diphenyl imidazolidinedione with propionyl dihydropyridine-CONH$_2$) | 3-[3'-[3''-carbamoyl-1'',4''-dihydropyridin-1''-yl)propionyloxymethyl]-5,5-diphenyl-2,4-imidazolidinedione | phenytoin-CDS$_3$ | Example 16 hereinbelow | as phenytoin-CDS$_1$ |

-continued

| Structure | Chemical Name | Abbreviated Name | Synthesis | Pharmacological Use |
|---|---|---|---|---|
| [structure: 1,4-dihydropyridine with N-CH3, 3-C(=O)-NH-(CH2)3-COOCH2-phenyl] | 1-methyl-3-N-[3-(benzyloxy-carbonyl)propyl]carbamoyl-1,4-dihydropyridine | GABA-CDS$_1$ | Anderson et al Psychopharmacology (1987)92:157-163 | anticonvulsant, anxiolytic agent |
| [structure: 1,4-dihydropyridine with N-CH3, 3-C(=O)NH(CH2)3CO-O-cyclohexyl] | 1-methyl-3-{N-[(3'-cyclohexyl-carbonyl)propyl]}carbamoyl-1,4-dihydropyridine | GABA-CDS$_2$ | Example 20 hereinbelow | as GABA-CDS$_1$ |
| [structure: 1,4-dihydropyridine with N-CH3, 3-C(=O)-NHCH2CH2OC(=O)-CH(CH2CH2CH3)2] | 1-methyl-3-[2'-(2''-propyl)-pentanoyloxy)ethylcarbamoyl-1,4-dihydropyridine | valproic acid-CDS$_1$ | Example 61 hereinbelow | anticonvulsant agent |
| [structure: 1,4-dihydropyridine with N-CH3, 3-C(=O)-OCH2CH2OC(=O)-CH(CH2CH2CH3)2] | 1-methyl-3-[2'-(2''-propyl)-pentanoyloxy)ethoxycarbonyl-1,4-dihydropyridine | valproic acid-CDS$_2$ | Example 65 hereinbelow | as valproic acid-CDS$_1$ |
| [structure: 1,4-dihydropyridine with N-CH2CH2OC(=O)-CH(CH2CH2CH3)2 and 3-CONH2] | 1-[2'-(2''-propyl)pentanoyloxy)ethyl-3-carboxamide-1,4-dihydropyridine | valproic acid-CDS$_3$ | Example 24 hereinbelow | as valproic acid-CDS$_1$ |

| Structure | Chemical Name | Abbreviated Name | Synthesis | Pharmacological Use |
|---|---|---|---|---|
| 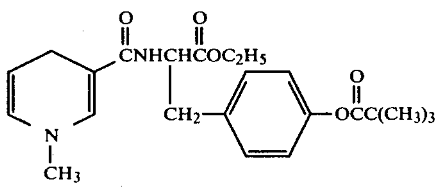 | 1-methyl-3-{N-[(1'-ethoxy-carbonyl)-2'-(4''-pivaloyloxy-phenyl)ethyl]}carbamoyl-1,4-dihydropyridine | tyrosine-CDS₁ | Example 29 hereinbelow | neurotransmitter amino acid |
| 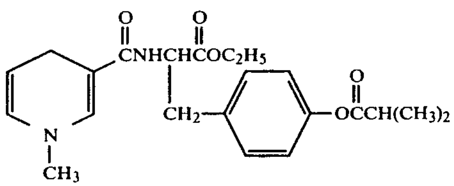 | 1-methyl-3-{N-[(1'-ethoxy-carbonyl)-2'-(4''-isobutyryloxy-phenyl)ethyl]}carbamoyl-1,4-dihydropyridine | tyrosine-CDS₂ | Example 30 hereinbelow | as tyrosine-CDS₁ |
| 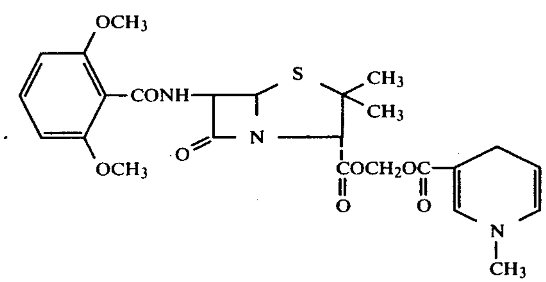 | [[(1,4-dihydro-1-methyl-3-pyridinyl)carbonyl]oxy]methyl [2S-(2α,5α,6β)]-3,3-dimethyl-7-oxo-6-[(2,6-dimethoxy)benz-amido]-4-thia-1-azabicyclo-[3.2.0]heptane-2-carboxylate | methicillin-CDS | Example 43 hereinbelow | antibiotic, antibacterial agent (e.g. for brain abscesses and neurosyphillis) |
| 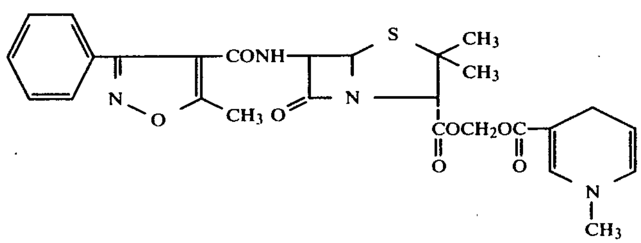 | [[(1,4-dihydro-1-methyl-3-pyridinyl)carbonyl]oxy]methyl [2S-(2α,5α,6β)]-3,3-dimethyl-6-(5-methyl-3-phenyl-4-isoxazole-carboxamido)-7-oxo-4-thia-1-azabicyclo[3.2.0]heptane-2-carboxylate | oxacillin-CDS | Example 44 hereinbelow | antibiotic, antibacterial agent (e.g. for brain abscesses, neurosyphillis) |

| Structure | Chemical Name | Abbreviated Name | Synthesis | Pharmacological Use |
|---|---|---|---|---|
| (structure) | [[(1,4-dihydro-1-methyl-3-pyridinyl)carbonyl]oxy]methyl [2S-(2α,5α,6β)]3,3-dimethyl-7-oxo-6-[(phenylacetyl)amino]-4-thia-1-azabicyclo[3.2.0]heptane-2-carboxylate | benzylpenicillin-CDS | Example 49 hereinbelow | antibiotic, antibacterial agent (e.g. for brain abscesses, neurosyphillis) |
| (structure) | [[(1,4-dihydro-1-methyl-3-pyridinyl)carbonyl]oxy]methyl [2S-(2α,5α,6β)]-6-[3-(2-chlorophenyl)-5-methyl-4-isoxazolecarboxamido]-3,3-dimethyl-7-oxo-4-thia-1-azabicyclo[3.2.0]heptane-2-carboxylate | cloxacillin-CDS | Example 45 hereinbelow | antibiotic, antibacterial agent (e.g. for brain abscesses, neurosyphillis) |
| (structure) | [[(1,4-dihydro-1-methyl-3-pyridinyl)carbonyl]oxy]methyl [2S-(2α,5α,6β)]-6-[3-(2,6-dichlorophenyl)-5-methyl-4-isoxazolecarboxamido]-3,3-dimethyl-7-oxo-4-thia-1-azabicyclo[3.2.0]heptane-2-carboxylate | dicloxacillin-CDS | Example 46 hereinbelow | antibiotic, antibacterial agent (e.g. for brain abscesses, neurosyphillis) |
| (structure) | [[N-[3-(10,11-dihydro-5H-dibenz[b,f]azepin-5-yl)propyl-N-methylamino)carbonyloxy]-methyl 1,4-dihydro-1-methyl-3-pyridinecarboxylate | desipramine-CDS$_1$ | Example 56 hereinbelow | antidepressant |

| Structure | Chemical Name | Abbreviated Name | Synthesis | Pharmacological Use |
|---|---|---|---|---|
| 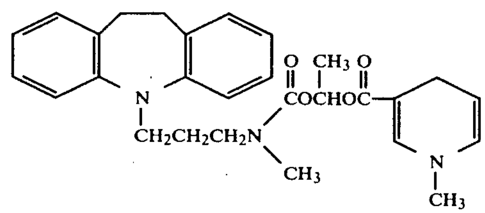 | [1-{N-[3-(10,11-dihydro-5H-dibenz[b,f]azepin-5-yl)]propyl-N-methylamino}carbonyloxy]ethyl 1,4-dihydro-1-methyl-3-pyridine-carboxylate | desipramine-CDS$_2$ | Example 57 hereinbelow | antidepressant |
| 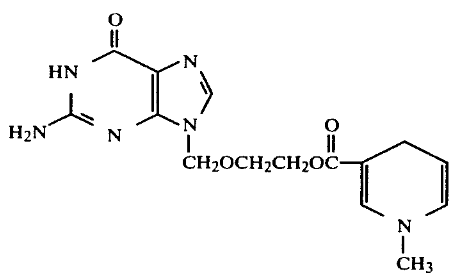 | 1-methyl-3-{[2-(9-guanylmethoxy)-ethoxy]carbonyl}-1,4-dihydropyridine | acyclovir-CDS or ACV-CDS | Example 103 hereinbelow | antiviral, anti-herpetic agent (e.g. for herpes simplex encephalitis) |
| 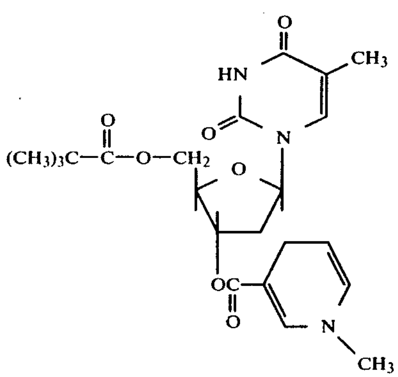 | 3'-(1,4-dihydro-1-methyl-3-pyridinylcarbonyl)-5'-pivaloyl-trifluorothymidine | trifluorothymidine-CDS or TFT-CDS | Example 107 hereinbelow | antiviral, anti-herpetic agent |

-continued

| Structure | Chemical Name | Abbreviated Name | Synthesis | Pharmacological Use |
|---|---|---|---|---|
| 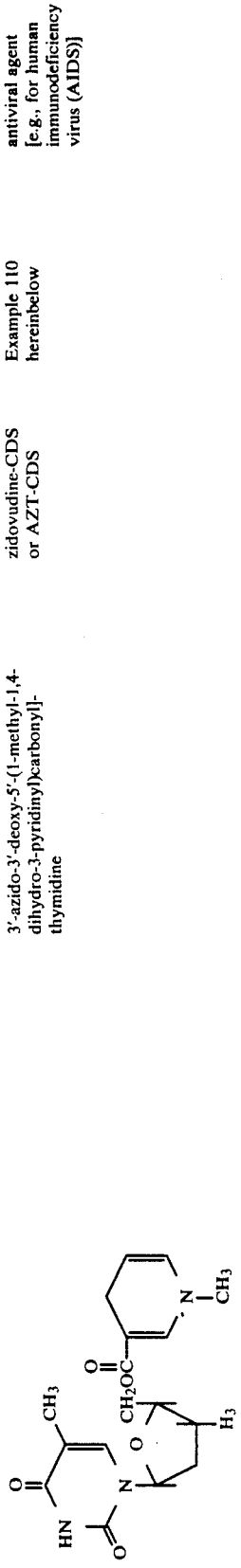 | 3'-azido-3'-deoxy-5'-{(1-methyl-1,4-dihydro-3-pyridinyl)carbonyl}-thymidine | zidovudine-CDS or AZT-CDS | Example 110 hereinbelow | antiviral agent [e.g., for human immunodeficiency virus (AIDS)] |
| 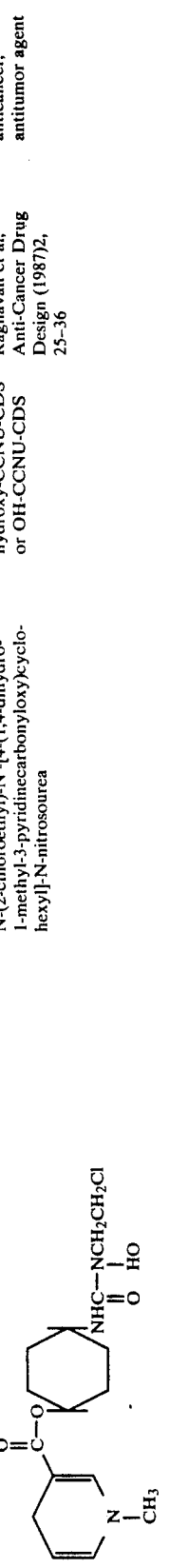 | N-(2-chloroethyl)-N'-[4-(1,4-dihydro-1-methyl-3-pyridinecarbonyloxy)cyclohexyl]-N-nitrosourea | hydroxy-CCNU-CDS or OH-CCNU-CDS | Raghavan et al, Anti-Cancer Drug Design (1987)2, 25-36 | anticancer, antitumor agent |
| 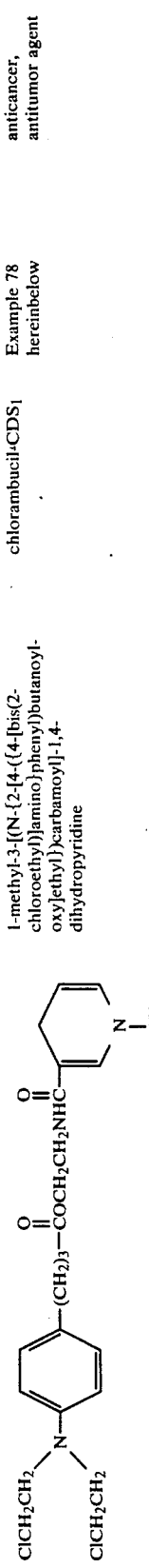 | 1-methyl-3-[{N-{2-[4-({4-[bis(2-chloroethyl)]amino}phenyl)butanoyloxy]ethyl})carbamoyl]-1,4-dihydropyridine | chlorambucil-CDS₁ | Example 78 hereinbelow | anticancer, antitumor agent |
| 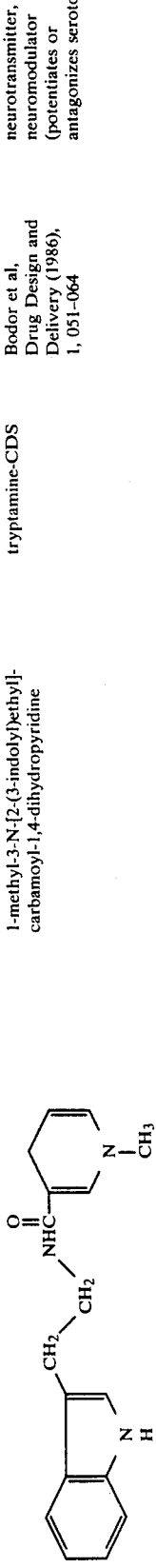 | 1-methyl-3-N-[2-(3-indolyl)ethyl]-carbamoyl-1,4-dihydropyridine | tryptamine-CDS | Bodor et al, Drug Design and Delivery (1986), 1, 051-064 | neurotransmitter, neuromodulator (potentiates or antagonizes serotonin) |

-continued

| Structure | Chemical Name | Abbreviated Name | Synthesis | Pharmacological Use |
|---|---|---|---|---|
| | 9-fluoro-11β,17-dihydroxy-16α-methyl-21-[[(1-methyl-1,4-dihydropyridin-3-yl)carbonyl]oxy]pregna-1,4-diene-3,20-dione | dexamethasone-CDS | Example 118 hereinbelow | antiinflammatory agent |
| | 11β,17-dihydroxy-21-[[(1-methyl-1,4-dihydropyridin-3-yl)carbonyl]oxy]pregn-4-ene-3,20-dione | hydrocortisone-CDS | Example 121 hereinbelow | antiinflammatory agent |
| | 3-hydroxy-17β-[[(1-methyl-1,4-dihydropyridin-3-yl)carbonyl]oxy}-19-nor-17α-pregna-1,3,5(10)-trien-20-yne | ethinyl estradiol-CDS | Example 69 hereinbelow | estrogen- as estradiol-CDS |

-continued

| Structure | Chemical Name | Abbreviated Name | Synthesis | Pharmacological Use |
|---|---|---|---|---|
| (steroid structure with N-methyl-dihydropyridinyl carbonyloxy group) | 17β-{[(1-methyl-1,4-dihydropyridin-3-yl)carbonyl]oxy}-19-norpregn-4-en-20-yn-3-one | norethindrone-CDS | Brewster et al, Pharmaceutical Research (1986), 3(5), 278–285 | progestin (e.g. for use in threatened abortion, endometriosis, other menstrual disorders, and as a contraceptive component) |
| (steroid structure with aromatic A-ring and N-methyl-dihydropyridinyl carbonyloxy group) | 3-hydroxy-17β-[(1-methyl-1,4-dihydropyridin-3-yl)carbonyl]-oxyestra-1,3,5(10)-triene | estradiol-CDS or E$_2$-CDS | U.S. Pat. No. 4,617,298, Example 11 | estrogen (e.g. for control of menopausal symptoms, for menstrual disorders such as dysmenorrhea, as a contraceptive component, for weight control, for prostate cancer, for male sexual dysfunction) |
| (steroid structure with N-methyl-dihydropyridinyl carbonyloxy group and angular methyl) | 17β-{[(1-methyl-1,4-dihydropyridin-3-yl)carbonyl]oxy}pregn-4-en-20-yn-3-one | ethisterone-CDS | Brewster et al, Pharmaceutical Research (1986), 3(5), 278–285 | progestin—as norethindrone-CDS |

| Structure | Chemical Name | Abbreviated Name | Synthesis | Pharmacological Use |
|---|---|---|---|---|
| | 13-ethyl-17β-[[(1-methyl-1,4-dihydropyridin-3-yl)carbonyl]oxy]-18,19-dinorpregn-4-ene-20-yn-3-one | norgestrel-CDS | Brewster et al, Pharmaceutical Research (1986), 3(5), 278-285 | progestin-as norethindrone-CDS |
| 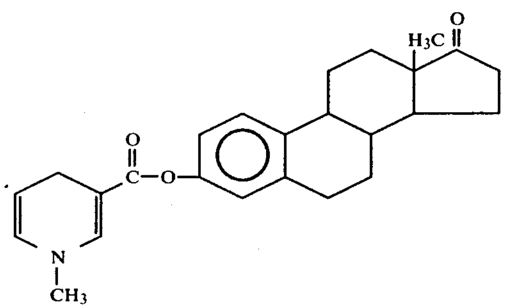 | 3-[(1-methyl-1,4-dihydro-3-pyridinyl)carbonyloxy]estra-1,3,5(10)-trien-17-one | estrone-CDS | U.S. Pat. No. 4,617,298, Example 3 | estrogen-as estradiol-CDS |
| 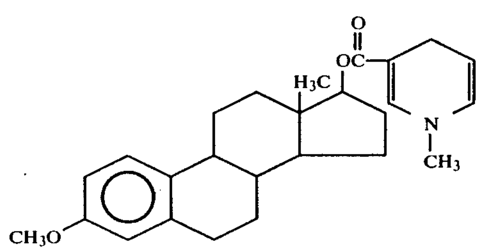 | 17β-[(1-methyl-1,4-dihydro-3-pyridinyl)carbonyloxy]estra-1,3,5(10)-trien-3-ol 3-methyl ether | estradiol 3-methyl ether-CDS | U.S. Pat. No. 4,617,298, Example 6 | estrogen-as estradiol-CDS |

-continued

| Structure | Chemical Name | Abbreviated Name | Synthesis | Pharmacological Use |
|---|---|---|---|---|
| | 3,17β-bis{[(1-methyl-1,4-dihydro-pyridin-3-yl)carbonyl]oxy}estra-1,3,5(10)-triene | estradiol bis-CDS | Example 72 hereinbelow | estrogen-as estradiol-CDS |
| | 3-(phenylcarbonyloxy)-17β-{[(1-methyl-1,4-dihydropyridin-3-yl)carbonyl]oxy}estra-1,3,5(10)-triene | estradiol benzoate-CDS | Example 75 hereinbelow | estrogen-as estradiol-CDS |
| | 17β-{[(1-methyl-1,4-dihydropyridin-3-yl)carbonyl]oxy}-19-norpregn-5(10)-en-20-yn-3-one | norethynodrel-CDS | from norethynodrel, analogously to methods of Brewster et al, Pharmaceutical Research (1986), 3(5), 278–285; also U.S. Pat. No. 4,540,564 | progestin-as norethindrone-CDS |

-continued

| Structure | Chemical Name | Abbreviated Name | Synthesis | Pharmacological Use |
|---|---|---|---|---|
| 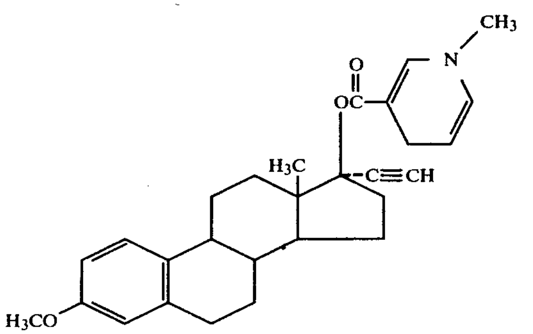 | 3-methoxy-17β-{[1-methyl-1,4-dihydropyridin-3-yl)carbonyl]oxy}-19 nor-17α-pregna-1,3,5(10)-trien-20-yne | mestranol-CDS | from mestranol, analogously to methods of Brewster et al, Pharmaceutical Research (1986), 3(5), 278–285; also U.S. Pat. No. 4,617,298 | estrogen-an estradiol-CDS |
| | 1-methyl-3-[N-(2-{1-(p-chlorobenzoyl)-5-methoxy-2-methyl-3-indolyl}acetoxy)ethyl)carbamoyl]-1,4-dihydropyridine | indomethacin-CDS | Example 97 hereinbelow | antiinflammatory agent |
| 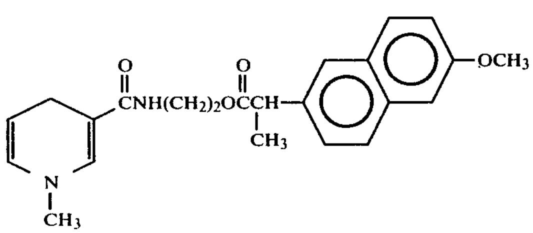 | 1-methyl-3-{N-[2-(6-methoxy-α-methyl-2-naphthalenylacetoxy)ethyl]-carbamoyl}-1,4-dihydropyridine | naproxen-CDS | Example 96 hereinbelow | antiinflammatory agent |

-continued

| Structure | Chemical Name | Abbreviated Name | Synthesis | Pharmacological Use |
|---|---|---|---|---|
| (structure) | 1-methyl-3-{N-{4-{4-({[bis(2-chloroethyl)]amino}phenyl)butanoyl-oxy]cyclohexyl}carbamoyl}-1,4-dihydropyridine | chlorambucil-CDS$_2$ | Example 82 hereinbelow | as chlorambucil-CDS$_1$ |
| (structure) | 1-methyl-3-[N-{2-[4-({4-[bis(2-chloroethyl)]amino}phenyl)butanoyl-oxy]propyl}carbamoyl]-1,4-dihydropyridine | chlorambucil-CDS$_3$ | Example 85 hereinbelow | as chlorambucil-CDS$_1$ |
| (structure) | 1-methyl-3-[N-(2-phenyl-2-({4-[bis(2-chloroethyl)]amino}phenyl)butanoyloxy)-ethyl}carbamoyl]-1,4-dihydropyridine | chlorambucil-CDS$_4$ | Example 90 hereinbelow | as chlorambucil-CDS$_1$ |
| (structure) | 1-methyl-3-[N-({1-[4-(4-{[bis(2-chloroethyl)]amino}phenyl)butanoyl-oxy]cyclohexyl}methyl)carbamoyl]-1,4-dihydropyridine | chlorambucil-CDS$_5$ | Example 101 hereinbelow | as chlorambucil-CDS$_1$ |

-continued

| Structure | Chemical Name | Abbreviated Name | Synthesis | Pharmacological Use |
|---|---|---|---|---|
|  | N-(2-fluoroethyl)-N'-{2-(1,4-dihydro-1-methyl-3-pyridinecarbonyloxy)ethyl]-N-nitrosourea | FENU-CDS | Example 127 hereinbelow | anticancer, antitumor agent |
| 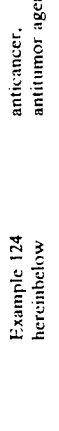 | N-(2-chloroethyl)-N'-{2-(1,4-dihydro-1-methyl-3-pyridinecarbonyloxy)ethyl]-N-nitrosourea | HENU-CDS | Example 124 hereinbelow | anticancer, antitumor agent |
| 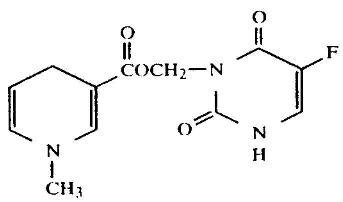 | 3-(1,4-dihydro-1-methyl-3-pyridinylcarbonyloxymethyl)-5-fluorouracil | 5-FU-CDS$_1$ | Example 135 hereinbelow | anticancer, antitumor agent |
| 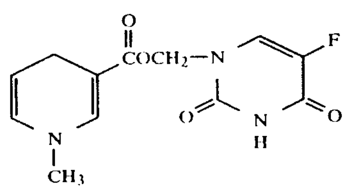 | 1-(1,4-dihydro-1-methyl-3-pyridinecarbonyloxy)methyl-5-fluorouracil | 5-FU-CDS$_2$ | Example 133 hereinbelow | anticancer, antitumor agent |

The cyclodextrins contemplated for use herein are hydroxypropyl, hydroxyethyl, glucosyl, maltosyl and maltotriosyl derivatives of β-cyclodextrin and the corresponding derivatives of γ-cyclodextrin. The hydroxyalkyl groupings may contain one or more hydroxyl groups, e.g. hydroxypropyl (2-hydroxypropyl, 3-hydroxypropyl), dihydroxypropyl and the like. The glucosyl, maltosyl and maltotriosyl derivatives may contain one or more sugar residues, e.g. glucosyl or diglucosyl, maltosyl or dimaltosyl. Various mixtures of the cyclodextrin derivatives may be used as well, e.g. a mixture of maltosyl and dimaltosyl derivatives. Specific cyclodextrin derivatives for use herein include hydroxypropyl-β-cyclodextrin (HPCD or HPBCD), hydroxyethyl-β-cyclodextrin (HEBCD), hydroxypropyl-γ-cyclodextrin (HPGCD), hydroxyethyl-β-cyclodextrin (HEGCD), dihydroxypropyl-β-cyclodextrin (2HPBCD), glucosyl-β-cyclodextrin ($G_1$-β-CD or $G_1$BCD), diglucosyl-β-cyclodextrin ($2G_1$-β-CD or $2G_1$BCD), maltosyl-β-cyclodextrin ($G_2$-β-CD or $G_2$BCD), maltosyl-γ-cyclodextrin ($G_2$-γ-CD or $G_2$GCD), maltotriosyl-β-cyclodextrin ($G_3$-β-CD or $G_3$BCD), maltotriosyl-γ-cyclodextrin ($G_3$-γ-CD or $G_3$GCD) and dimaltosyl-β-cyclodextrin ($2G_2$-β-CD or $2G_2$BCD), and mixtures thereof such as maltosyl-β-cyclodextrin/dimaltosyl-β-cyclodextrin.

Hydroxypropyl-β-cyclodextrin for use in the methods of the present invention is commercially available. Alternatively, it may be prepared by known methods, especially by use of the optimized procedure of Pitha et al, *International Journal of Pharmaceutics*, 29, 73–82 (1986). The following is a typical procedure using the Pitha et al method:

31 g of sodium hydroxide were dissolved in 250 mL of water. Then, 100 g of β-cyclodextrin were added and the solvent was warmed to effect solution. The flask was cooled and 50 mL of propylene oxide were added. The flask was fitted with a dry ice/acetone condenser during the addition. The solution was allowed to come to room temperature and was stirred for 72 hours. The solution was then neutralized with concentrated hydrochloric acid and diluted with water. The solvent was removed in vacuo, leaving a syrup which was taken up in ethanol. After stirring for 30 minutes at room temperature, the sodium chloride produced was removed by filtration. The filter cake was washed with ethanol and the combined ethanol layers were reduced in vacuo. The residue was dissolved in water and dialyzed in cellulose acetate (#7, 38 mm 4.6 mL/cm, molecular weight cut off=1000, Fisher Scientific). After 5 hours at 0° C., the solution was removed from the dialysis tubing and freeze-dried. The resulting solid was suspended in acetone and stirred overnight. The filtered solid was resuspended in acetone and stirred for 24 hours. The solid was collected by filtration and dissolved in 200 mL of water and then lyophilized. 75 grams of purified hydroxypropyl-β-cyclodextrin were obtained. The degree of substitution was calculated by NMR and by comparison with an authentic sample.

In forming a complex with $E_2$-CDS, a 50% solution (w/w) of 2-hydroxypropyl-β-cyclodextrin (HPCD) was made in distilled water. An excess of $E_2$-CDS was added and the solution then was purged with helium. The resulting suspension was then sonicated for 30 minutes, filtered through a glass filter (ASTM 10-15M, Pyrex No. 36060) and freeze-dried overnight. Best results were obtained by hard-freezing the aqueous solution of the $E_2$-CDS/HPCD complex for at least 10 hours before lyophilization. The degree of complex formation was determined by dissolving a small amount of the dry complex in methanol and then analyzing by high pressure liquid chromatography (HPLC). The degree of complexation was found to vary between 20–40 mg/g and the solubility of the complex was determined to be $2.2 \times 10^4$ mg/L.

The Pitha et al method for preparation of HPCD by condensation of propylene oxide with β-cyclodextrin in alkaline aqueous solution unfortunately suffers from disadvantages, particularly in purification of the product. After completion of the condensation, the reaction mixture is neutralized with hydrochloric acid, water is evaporated under vacuum and the syrupy residue is dissolved in ethanol to precipitate sodium chloride, the main by-product of the reaction. After filtration, ethanol is evaporated under vacuum and the residue is dissolved in water and dialyzed to remove the remaining sodium chloride and polymerization products of propylene oxide. During dialysis, part of the hydroxypropyl-β-cyclodextrin goes through the membrane and is lost. The dialysate is then freeze-dried, twice stirred in acetone and washed to remove the remaining polymerization products. Finally, hydroxypropyl-β-cyclodextrin is freeze-dried again. The second freeze-drying is necessary because the product after washing with acetone is not homogeneous.

To overcome these difficulties with the Pitha et al process, a new method has been developed by Maciej Smulkowski of the University of Florida, Gainesville, Fla. for the synthesis of HPCD. This new method involves removal of sodium hydroxide from the reaction mixture by an ion exchange resin ($H^+$); as a result, several time-consuming steps of Pitha et al's purification can be avoided. Moreover, the amount of sodium hydroxide used by Pitha et al (7 equivalents for one of β-cyclodextrin) can be decreased to 2 equivalents of sodium hydroxide per cyclodextrin molecule, and still produce a product with the appropriate NMR and optical rotation.

According to the new method, β-cyclodextrin is first condensed with propylene oxide in alkaline solution, sodium hydroxide is removed on an ion exchange column (Dowex 50W-X8, $H^+$ form), the eluate is evaporated under vacuum to one-half of the original volume, the remaining solution is freeze-dried, the resulting white solid is washed with acetone and freeze-dried again, then subjected to grinding and sieving. Possible modifications of this method include: (1) use of the ionic exchange resin for neutralization in the reaction flask, with filtration of the resin and washing on the filter funnel; (2) use of calcium, magnesium, lithium or potassium hydroxide to dissolve the cyclodextrin; (3) removal of hydroxides after the reaction by saturating the reaction mixture with carbon dioxide or neutralization with sulfuric acid in place of the ion exchange resin; (4) use of even less sodium hydroxide (between 1 and 2 equivalents); and (5) elimination of the second freeze-drying.

The following is a typical procedure using the new, improved method:

50 g of β-cyclodextrin was dissolved in a solution of 3.53 g of sodium hydroxide in 75 mL of water and treated with 29 mL of propylene oxide at 0° C. The reaction mixture was maintained for 5 hours at that temperature, then was kept at room temperature for 42 hours. At the end of that time, the reaction mixture was passed through the Dowex 50W-X8 column ($H^+$ form), the column was washed with water and the eluate was evaporated under vacuum to a volume of 100 mL, then freeze-dried. The resulting white solid was washed with acetone to give 51 g of HPCD, with the same degree of substitution (4.7) and NMR as the HPCD prepared by the Pitha et al method. Residue on ignition was 0.0%. Optical rotation also was identical to that of the Pitha et al product.

Condensation of 25 g of β-cyclodextrin using 7.71 g of sodium hydroxide gave similar results.

A further improvement in the new, improved HPCD synthesis utilizes activated carbon for purification of the solution prior to the last freeze-drying. Thus, when the aqueous solution from the Dowex 50 ionic exchange column was treated with activated carbon, most of the polymerization products were removed without loss of HPCD, and the filtrate after only one washing with ethyl acetate was ready for final freeze-drying. In this way, only one freeze-drying was required. Crystallization of the final product instead of freeze-drying is also possible, at least on a small scale.

The product from the modified new process (using activated carbon) appears to be superior to that of the original new process and the Pitha et al process. First, the product is snow white and produces a colorless aqueous solution, whereas solutions of the earlier products were yellow. Secondly, the product is not oily, which may be due to removal of more highly substituted, less soluble, oily cyclodextrins.

HPCD can be prepared in varying degrees of substitution, such as 5 or 7. Typically, the foregoing procedure is used to produce HPCD (ASDS 7). The mass spectra for the isomeric misture of HPCD centers around 7 degrees of substitution. This spectra is obtained by "softly" ionizing the sample using fast atom bombardment. The generated spectra is similar to those previously reported (obtained by Californium-252 plasma desorption) in both the symmetry of the isomeric distribution and the numerical spread of the isomers formed.

Hydroxyethyl-β-cyclodextrin (HEBCD) can be prepared analogously to HPCD, utilizing the improved procedure detailed above but substituting an equivalent quantity of ethylene oxide for the propylene oxide there employed.

The synthesis of 2-hydroxypropyl-γ-cyclodextrin (HPGCD) similarly uses the same basic procedure as for HPCD, substituting γ-cyclodextrin for the β-cyclodextrin starting material. However, because γ-cyclodextrin contains eight glucose residues compared to seven for β-cyclodextrin, the amount of propylene oxide used can be reduced in order to lower the degree of substitution. Use of 0.75 mole of propylene oxide per 0.077 mole of γ-cyclodextrin (~20% excess considering 8 OH groups) affords HPGCD with a degree of substitution of 8, while use of 0.56 mole of propylene oxide (~10% less than equivalent) gives a degree of substitution of about 7.

Hydroxyethyl-γ-cyclodextrin (HEGCD) can be prepared similarly to HPGCD as described in the preceding paragraph, simply using an equivalent quantity of ethylene oxide in place of the propylene oxide.

Thus, the hydroxyalkyl cyclodextrins intended for use herein can be prepared by procedures described by Pitha et al or variations thereof. Obtained by these procedures, the cyclodextrins are intrinsically amorphous mixtures. The importance of the amorphous nature of the cyclodextrins is described by Pitha et al, *J. Pharm.* *Sci.*, Vol. 74, No. 9, September 1985, 987–990, and in Pitha U.S. Pat. No. 4,727,064. The advantages of the amorphous nature of these materials are more pronounced at higher concentrations of cyclodextrin.

The other cyclodextrins intended for use in the present invention, i.e. the glucosyl, maltosyl and maltotriosyl derivatives of β- and γ-cyclodextrin, are branched cyclodextrins which are highly soluble in water as compared to the parent cyclodextrins. These branched cyclodextrins can be produced by microbiological processes from the parent cyclodextrins. Glucosyl-β-cyclodextrins can be obtained from the mother liquor of a large-scale β-cyclodextrin synthesis with *Bacillus ohbensis* cyclomaltodextrin glucanotransferase; see Koizumi et al, *Chem. Pharm. Bull.*, 35 (8), 3413–3418 (1987) and reference cited therein. Maltosyl and maltotriosyl β- and γ-cyclodextrins can be prepared from the parent cyclodextrin and maltose or maltotriose through the reverse action of Pseudomonas isoamylase or *Klebsiella aerogenes* pullulanase, while glucosyl-γ-cyclodextrin can be prepared by enzymatic hydrolysis of maltosyl-γ-cyclodextrin; see Okada et al, *Chem. Pharm. Bull.*, 36 (6), 2176–2185 (1988) and references cited therein. The preparation of maltosyl-β-cyclodextrin by reacting maltose with β-cyclodextrin in the presence of pullulanase is also described in Japanese Kokai No. 61-287902, published Dec. 18, 1986, and Japanese Kokai No. 61-197602, published Sept. 1, 1986. A mixture of maltosyl-β-cyclodextrin and various dimaltosyl-β-cyclodextrins may be conveniently employed. See also Kainuma et al U.S. Pat. No. 4,668,626, issued May 26, 1987.

The development of a carrier-mediated dihydropyridine⇌pyridinium salt redox system (which, in the dihydropyridine form, is also termed a chemical delivery system or CDS) has resulted in the enhanced and/or sustained delivery of a variety of drugs to the central nervous system. While the physiochemical properties of the CDS are optimized for brain-uptake and retention, they are often incompatible with aqueous formulations. A salient example is $E_2$-CDS, a CDS based on estradiol. This dihydronicotinate passes the BBB and is oxidized to the corresponding quaternary salt, $E_2Q^+$. The sustained levels of $E_2Q^+$ thus produced then slowly release estradiol, which exerts profound central estrogenic effects. These effects include LH-suppression in ovariectomized rats and a reversible suppression of cyclicity in intact female rats and are exerted for prolonged periods. The $E_2$-CDS is highly lipophilic and only poorly water soluble (0.2 µg/mL). This requires that $E_2$-CDS be administered in watermiscible organic solvents such as dimethylsulfoxide (DMSO) or dimethylacetamide (DMA). While this procedure is not inappropriate for laboratory animal studies, it is clearly inadequate for human use for reasons enumerated hereinabove. The development of an aqueous formulation of $E_2$-CDS was therefore investigated. Criteria for this formulation include that it have minimal toxicity, that it be equivalent with $E_2$-CDS in DMSO or DMA in delivering $E_2Q^+$ to the brain and that the technology developed be applicable to other dihydropyridine⇌pyridinium salt redox systems.

EXPERIMENTAL SECTION

Materials: 3-Hydroxy-17β-[(1-methyl-1,4-dihydropyridin-3-yl)carbonyl]oxyestra-1,3,5(10)-triene ($E_2$-CDS), 1-methyl-3-{{N-{β-[3,4-bis(pivalyloxy)phenyl]ethyl}-carbonyl}}-1,4-dihydropyridine (DA-CDS), 17β-[(1,4-dihydro-1-methyl-3-pyridinylcarbonyl)oxy]androst-4-en-3-one (T-CDS$_1$), 1-methyl-3-N-[3-(benzyloxycarbonyl)propyl]carbamoyl-1,4-dihydropyridine (GABA-CDS$_1$), 1-methyl-3-{[2-(9-guanylmethoxy)ethoxy]carbonyl}-1,4-dihydropyridine (ACV-CDS) and 17β-{[(1-methyl-1,4-dihydropyridin-3-yl)carbonyl]oxy}-19-norpregn-4-en-20-yn-3-one (N-CDS) were synthesized according to published procedures. 2-Hydroxypropyl-β-cyclodextrin (statistical degree of substitution=5.1 or 7) (HPCD) was prepared according to the method of Pitha et al. Other cyclodextrins (α, β or γ) were obtained from Aldrich Chemical Co. and other steroids (estradiol, estradiol 17-valerate, estriol, estrone, estradiol 3-methyl ether and testosterone 17-propionate), were purchased from Sigma Chemical Co. All prepared compounds were fully characterized by spectroscopic and microcombustion analysis (Atlantic Microlabs) prior to study. Mass spectroscopic studies were performed on a Kratos MS80RFA double-focusing instrument fitted with a fast atom gun. Cyclodextrin mixtures were analyzed by fast atom bombardment of the samples prepared in a glycerol matrix. Degrees of substitution were determined from the isomeric mass distribution. Nuclear magnetic resonance spectra were obtained on a Varian EM360 60 MHz spectrometer. Values were recorded relative to an internal standard [3-(trimethylsilyl)propionic 2,2,3,3-d4 acid, sodium salt, DDS] and all samples were run in D$_2$O. The degree of substitution was calculated by comparing the integrated area attributed to the anomeric hydrogen compared to that of the hydroxypropyl functionality.

Effect of Solubilizing Agents: An excess of E$_2$-CDS was sonicated with an aqueous solution of the appropriate solubilizing agent for 30 minutes. The suspension was then centrifuged, filtered through 0.45 μm polyvinylidene difluoride (Millex-HV4, Millipore ®) membranes and analyzed by HPLC. For studies with 2-hydroxypropyl-β-cyclodextrin, an excess of E$_2$-CDS was added to different concentrations (% w/v) of HPCD and the solubility (mg/mL) was determined spectroscopically (UV=360 nm, ε=6487 in methanol). An estimation of the bulk equilibrium constant was obtained by correlating the millimolarity of E$_2$-CDS solubilized and the millimolarity of the cyclodextrin added. This latter value was calculated using the average molecular weight of the isomeric mixture determined by mass spectroscopy. The solubilizing effect of a 50% w/w solution of HPCD was also examined for a series of steroids and dihydropyridines (CDS). These studies were carried out in a similar manner to those previously described.

Preparation of Solid Complexes: An excess of E$_2$-CDS or other CDS was added to a 50% w/w solution of HPCD. The suspension was sonicated for 30 minutes, filtered through 0.45 μm PVDF membranes and freeze-dried. The degree of incorporation was determined either spectrophotometrically or by HPLC. In some cases, the effect of solubilizing agents on the degree of incorporation was examined. This involved adding small amounts of polyoxyethylene 20 cetyl ether (Brij), polyoxyethylene sorbitan monooleate (Tween 80) or ethanol to the aqueous solution prior to lyophilization.

Analytical Methodology: In determining concentrations spectrophotometrically, a Cary 219 (Varian) or an HP 8451A Diode Array (Hewlett Packard) spectrophotometer was used. Standard curves were prepared in methanol and gave correlation coefficients greater than 0.999. For the CDS, the wavelength monitored was 360 nm while for estrogen 220 nm was used.

The HPLC system consisted of either an Autochrom M500 pump fitted with a Rheodyne injector or a Perkin-Elmer Series 4 pump, a Kratos Spectroflow 757 variable wavelength detector and either a Beckman recorder or an LCI-100 integrator (Perkin-Elmer). Separation was achieved on an Analytical Sciences, Inc. (ASI) 10 μm particle size, C18 reversed phase 30 cm×3.9 mm i.d. analytical column. The flow rate was 1 mL/min, the compounds were detected at 360 nm and in all determinations the temperature was ambient. A mobile phase containing 82:1:1:16 (acetonitrile:tetrahydrofuran:acetic acid:H$_2$O) eluted the E$_2$-CDS at 4.4 min, the DA-CDS at 4.4 min, the T-CDS$_1$ at 6.8 min and the N-CDS at 5.2 min. For the GABA-CDS$_1$, a mobile phase consisting of 50:1:1:48 of the same components was required. The retention time was 5.2 min. Other compounds were assayed spectrophotometrically.

Animal Studies: Conscious, restrained Sprague-Dawley rats (female, BW=200 g) were given either 15 mg/kg E$_2$-CDS in DMSO or 5 mg/kg of E$_2$-CDS complex in HPCD (E$_2$-CDS-HPCD) in water by intravenous injection (tail vein). At various times after the administration, animals were sacrificed and trunk blood and organs collected. The organs were then weighed, homogenized in water and deproteinized with cold acetonitrile. The organ homogenates were centrifuged and the supernatant analyzed for E$_2$Q$^+$ and E$_2$-CDS using a precolumn enrichment technique, the details of which are given hereinbelow.

RESULTS AND DISCUSSION

As discussed hereinabove, cyclodextrins have been used to increase the water solubility of a number of drugs, including steroids. These cyclic oligomers contain various numbers of α-1,4-linked glucose units. The number of these units (α=six, β=seven, γ=eight) determine the size of a cone-like cavity which is amenable to inclusion by many drugs. The stability of the complex formed depends on the fit of the drug into the cyclodextrin and the cyclodextrin concentration. Unfortunately, the cyclodextrin best suited for complexation with steroids, i.e. β-cyclodextrin, is poorly water-soluble. This property is derived from the high degree of hydrogen bonding which occurs in the crystal lattice. To add to the problem, β-cyclodextrin is known to cause nephrosis in rats, a toxicity which results, at least partially, from its poor water solubility. In any case, little change in the aqueous solubility of E$_2$-CDS was observed when it was equilibrated with various solutions of either α, β or γ-cyclodextrin. As illustrated in Table I, concentrations of α-cyclodextrin up to 50 mm increased the aqueous solubility of E$_2$-CDS only 25-fold while β and γ-cyclodextrin increase the solubility of the CDS 135 and 110-fold respectively. The relationship between the aqueous solubility of E$_2$-CDS and the concentration of the unsubstituted cyclodextrins was not linear, a situation which is also observed in the case of the parent steroid. In any case, the limited water solubility and the relatively poor complexation provided by α-, β- or γ-cyclodextrin are unsuitable for pharmaceutical exploitation. The toxicity of β-cyclodextrin underscores this assessment.

TABLE I
EFFECT OF VARIOUS CYCLODEXTRINS ON THE WATER SOLUBILITY OF $E_2$-CDS

| Cyclo-dextrin | Conc. Range (mM or % w/v) | Maximum Solubility (mg/mL) | Conc. of Cyclodextrin at Max. Solubility (mM or % w/v) | n |
|---|---|---|---|---|
| None | — | 0.0002 | — | — |
| Alpha (α) | 5–50 mM | 0.005 | 50 mM | 7 |
| Beta (β) | 5–15 mM | 0.027 | 10 mM | 5 |
| Gamma (γ) | 5–50 mM | 0.022 | 10 mM | 5 |
| HPCD (7 ASDS) | 0.78–62.5 % w/v | 30.19 | 62.5% w/v | 9 |
| HPCD (5.1 ASDS) | 1–62.5 % w/v | 35.12 | 62.5% w/v | 5 |

Several efforts have been made to increase the aqueous solubility and, therefore, usefulness of cyclodextrins. Various methylated derivatives have been described but, in general, the acute toxicity of the modified compound is greater than that of the parent. Recently, an amorphous cyclodextrin composition was obtained by hydroxypropylation of β-cyclodextrin. The product, 2-hydroxypropyl-β-cyclodextrin (HPCD), is a mixture of isomers which can be characterized by the average statistical degree of substitution (ASDS). Either NMR or mass spectroscopy can be used to determine this value. These highly water soluble mixtures were shown by Pitha et al to dramatically increase the solubility of a number of compounds including gonadal steroids. In addition, preliminary toxicity studies have shown few, if any, harmful effects after either oral or intravenous administration.

HPCD (ASDS 5.1 or 7) was prepared according to the method of Pitha et al. The mass spectra for the isomeric mixture of HPCD centered around 7 degrees of substitution. This spectra was obtained by "softly" ionizing the sample using fast atom bombardment. The generated spectra was similar to those previously reported (obtained by Californium-252 plasma desorption) in both the symmetry of the isomeric distribution and the numerical spread of the isomers formed. In the cited example, as in the 5.1 ASDS case, no underivatized (toxic) β-cyclodextrin was detected.

In applying this HPCD composition to $E_2$-CDS, HPCD with low ASDS's was selected. As the degree of substitution increases, not only does the complexing propensity of the cyclodextrin decrease, presumably due to steric interactions, but the surface activity of the complex increases. This is undesirable since, in general, as the surface activity increases, so does the tendency of the material to cause hemolysis. Both the 5.1 and 7 ASDS HPCD had a profound effect on the solubility of $E_2$-CDS. In the 7 ASDS case, a linear increase (r=0.995) in the solubility of $E_2$-CDS was evident as the concentration of HPCD was increased. At 62.5% w/v, 30.2 mg/mL could be solubilized. In the 5.1 ASDS material, 35 mg/ml of $E_2$-CDS could be solubilized at 62.5% w/v. The lower ASDS material gave a 15% increase in incorporation. These data reflect an increase in solubility of five orders of magnitude (150,000-fold) over the solubility of $E_2$-CDS in water (Table I). Plotting the data obtained from the 7 ASDS study as millimolarity of $E_2$-CDS solubilized versus the millimolarity of HPCD added (based on the average molecular weight of the mixture) gave a line with a slope of 0.2. This is an estimation of the bulk stability of the cyclodextrin complex and compares reasonably with other systems.

These solutions could be freeze-dried giving a solid complex. A 50% w/w solution of HPCD gave a solid containing 37 mg $E_2$-CDS/gm complex. The complex was stable as a dry powder and could be easily reconstituted with water. In these manipulations, it was important to maintain the HPCD component greater than 20% w/v. Below this level, precipitation would occur. Several attempts were made to increase the degree of incorporation of the complex by adding various agents such as Brij (0.7% w/w), Tween 80 (0.8% w/w) or ethanol (10% v/v). While the addition of Brij increased the degree of incorporation to 189 mg/g, the complex was not stable, falling to 42 mg/g in 12 days. The other agents had only modest effects. The upper limit for a stable complex, therefore, appeared to be approximately 40 mg/g under these circumstances.

Since an inclusion complex is formed between $E_2$-CDS and the various components of the cyclodextrin mixture, it is possible that some portion of the $E_2$-CDS would not rapidly dissociate, thus lowering the biologically available concentration of $E_2$-CDS. To investigate this possibility, the ability of the HPCD (5.1 ASDS) formulation of $E_2$-CDS ($E_2$-CDS-HPCD) to deliver $E_2Q^+$ to the brain was measured and compared with the delivery of $E_2Q^+$ when $E_2$-CDS was administered in DMSO. Brain concentrations of $E_2Q^+$ were measured after systemic administration of either 15 mg/kg $E_2$-CDS in DMSO or 5 mg/kg $E_2$-CDS in aqueous HPCD. When the difference in dose is accounted for, i.e. the data is presented as % dose/g, no significant difference exists between brain levels of $E_2Q^+$ after $E_2$-CDS administration in DMSO or $E_2$-CDS-HPCD in an aqueous media, although the latter produce data which are strikingly more consisted and less variable. Interestingly, the levels of $E_2Q^+$ in the lung are lower after $E_2$-CDS-HPCD administration. One explanation for this is that when $E_2$-CDS is given in a water miscible solvent such as DMSO, there may be some tendency for the highly water insoluble $E_2$-CDS to precipitate. After a bolus i.v. injection, the aqueous, ionic environment of the lung may provide a suitable site for this precipitation. The lower levels obtained in the lung after $E_2$-CDS-HPCD administrations reflect not only the higher water solubility of the complex but may also indicate something of its in vivo dissociation constant. Quite surprisingly, this dissociation appears to be fast enough so not as to alter the distribution of $E_2$-CDS in the CNS, but slow enough to allow pulmonary transit (or transit from other organs such as the liver) without significant precipitation. In addition, the values for various organ concentrations are far less variable after $E_2$-CDS-HPCD administration, which may be explained by the higher water solubility of the complex and its lower tendency to precipitate. Ongoing pharmacological studies corroborate the effectiveness of the $E_2$-CDS-HPCD formulation in brain-selective delivery.

The effect of a 50% w/w solution of HPCD on the solubility of a number of steriods and other CDS is given in Table II.

TABLE II

SOLUBILITY OF VARIOUS STEROIDS AND VARIOUS DRUG CHEMICAL DELIVERY SYSTEMS IN A 50% W/W SOLUTION OF 2-HYDROXYPROPYL-$\beta$-CYCLODEXTRIN (ASDS 5.1) AND THE AMOUNT OF DRUG INCORPORATED IN THE FREEZE-DRIED COMPLEX

| Drug | Solubility (mg/mL) in 50% w/w HPCD | Amount of Drug in Dry Complex (mg/g) |
|---|---|---|
| $E_2$-CDS | 22 | 37 |
| Estradiol | 25 | — |
| Estriol | 40 | — |
| Estrone | 9.52 | — |
| Estradiol 3-Methyl Ether | 30 | — |
| Estradiol 17-Valerate | 13.8 | 23.5 |
| Testosterone | 38 | — |
| Testosterone 17-Propionate | 38 | 65.6 |
| Testosterone-CDS (T-$CDS_1$) | 17.1 | 29.0 |
| Norethindrone | 68 | — |
| Norethindrone-CDS (N-CDS) | 0.35 | 0.6 |
| GABA-$CDS_1$ | 93 | 160 |
| DA-CDS | 16 | 27 |
| ACV-CDS | 14.9 | 25 |

Thus, $E_2$-CDS and several other CDS were successfully solubilized with HPCD, although this is not universal: norethindrone-CDS, for example, was not readily solubilized. The best solubilization of $E_2$-CDS occured in an aqueous solution of HPCD, ASDS 5.1 or 7. These complexes could be freeze-dried and were stable. They were easily reconstituted in water so long as the cyclodextrin component was at least 20% w/v. This formulation was equivalent with $E_2$-CDS administered in DMSO in delivering $E_2$-$Q^+$ to the brain of rats. In additon, the formulation significantly reduced the lung concentrations of $E_2Q^+$. Data available at present indicates this excipient is less toxic, easily compressed into tablets, rapidly dissolved and readily and reproducibly synthesized.

$E_2$-CDS and several other CDS have also been successfully complexed with other cyclodextrin derivatives as defined herein. The other cyclodextrin/CDS complexes have the improved characteristics as noted before for the HPCD complexes.

In one example of the formulation of a solid complex, an excess of a representative CDS, $E_2$-CDS, was added to a 40% aqueous solution of a mixture of maltosyl-$\beta$-cyclodextrin (71%) and various dimaltosyl-$\beta$-cyclodextrins (29%) obtained from Ensuiko Sugar Co., Ltd., Lot No. 88190, and mixed for several hours. The suspension was then filtered and freeze-dried, and the amount of complexed drug was determined analytically by UV spectraphotometry. The amount of incorporation was determined to be 81.88 mg/g. The comparable figure for HPCD is approximately 36.2.

In further testing, maximum concentrations of selected CDS in varying concentrations of selected cyclodextrins were determined. The concentration of $E_2$-CDS (mg/mL) was as follows:

| Cyclodextrin | 20% | 40% |
|---|---|---|
| HPCD | 6.73 | 11.9 |
| HEBCD | 3.09 | 6.07 |
| HPGCD | — | 4.0 |

The concentration (mg/g) of the norethindrone-CDS was 7.13 in 40% HPCD and 15.9 in 40% HPGCD.

As noted above, use of a representative dihydropyridine redox system drug, i.e. $E_2$-CDS, complexed with a representative cyclodextrin derivative, HPCD, led to lower initial lung concentrations (and thus increased initial brain to lung concentrations) of the quaternary form as compared to administration of the redox system drug in DMSO. In studies of another representative redox system drug, namely a testosterone-CDS, T-$CDS_1$, similar observations were made, as detailed below.

EXPERIMENTAL SECTION

Materials: 2-Hydroxypropl-$\beta$-cyclodextrin (HPCD, degree of substitution 5.1) was prepared and purified according to the method of Pitha et al. The cyclodextrin inclusion complexes were prepared by equilibrating an excess of either testosterone propionate or T-$CDS_1$ with a 50% w/v aqueous solution of 2-hydroxypropyl-$\beta$-cyclodextrin. The solution was degassed and the suspension was sonicated for 30 minutes, after which it was filtered and the filtrate was lyophilized. The dried filtrate contained 65.6 mg testosterone propionate or 29.6 mg T-$CDS_1$ per gram of cyclodextrin complex. Compounds were analyzed for decomposition by thin-layer chromatography and ultraviolet absorption.

Animals: Male Sprague-Dawley rats, weighing 250-275 g, were purchased from Charles River Breeding Laboratories (Wilmington, Mass.) and were housed in an animal room which was light (14 hours; lights on at 0500 hours) and temperature ($23°\pm 1°$ C.) controlled. To elevate serum luteinizing hormone (LH) and to reduce the source of endogenous testosterone, animals were bilaterally orchidectomized via a mid-ventral incision under light ether anesthesia. All experiments were initiated 2 weeks after orchidectomy.

Experiment 1: On day 15 after orchidectomy, rats were ether-anesthetized and the right external jugular vein exposed. Animals were then administered one of the following: testosterone-chemical delivery system (T-$CDS_1$ or T-$CDS_2$), testosterone (Steraloids Inc., Wilton, N.H.) or the vehicle, dimethyl sulfoxide (DMSO; Fisher Scientific, Fair Lawn, N.J.). The testosterone-chemical delivery systems were given at doses equimolar to testosterone (25 mg/kg) so that T-$CDS_1$ was administered at 35.5 mg/kg and rats received T-$CDS_2$ at a dose of 45.1 mg/kg. DMSO was injected at a volume of 1 mL/kg. All compounds were administered by infusion over a 2 minute period. One milliliter of blood was withdrawn from the external jugular vein immediately before giving the drugs (1000 hours) and blood was sampled by cardiac puncture after 6, 12, 24 hours and on days 4 and 7. The sera were separated by centrifugation at $500\times g$ for 20 min at 4° C. and stored at $-20°$ C.

Experiment 2: Two weeks after orchidectomy, rats were administered either T-$CDS_1$, testosterone propionate (TP; Steraloids Inc.) or DMSO by means of intravenous infusion into the right external jugular vein in an effort to more effectively enhance the brain delivery of testosterone. It has been shown that slow infusion improves brain delivery of drugs attached to the chemical-delivery systems. TP was selected for comparison since it, like both of the T-CDS compounds, has an ester grouping (propionate) attached at carbon-17 ($C_{17}$). Gonadally-intact animals received the drug vehicle only. Two Harvard Apparatus reciprocal infusion/- withdrawal pumps (model 944) were used so that 4 animals could be simultaneously infused. Rate of infusion was 15 μL/min and animals were infused for 17 to 25 minutes. TP was given at 25 mg/kg and T-CDS was infused at a dose equimolar to TP (29.7 mg T-CDS$_1$ per kg body weight). The drug vehicle, DMSO, was administered at a dose of 1 mL/kg. One mL of blood was removed from the external jugular vein prior to drug infusion and from the sub-orbital sinus at 1, 3, 5, and 7 days. The sera were separated and stored as previously described.

Experiment 3: Orchidectomized rats were administered either testosterone-chemical delivery system (T-CDS$_1$) in HPCD (T-CDS$_1$-HPCD), testosterone propionate in cyclodextrin (TP-HPCD) or the vehicle, cyclodextrin (HPCD), via a single tail vein injection. T-CDS$_1$-HPCD (11.9 mg/kg) was given so that animals received T-CDS$_1$ at a dose equimolar to TP-HPCD (10 mg TP/kg body weight). Control rats received 25% HPCD (w/v) at 3.0 mL/kg. Blood was removed by cardiac puncture on days 0, 1, 3, 5 and 7, and separated and stored as previously described.

To evaluate peripheral effects of the drugs, the right seminal vesicle, vas deferens and ventral prostate gland were removed, cleaned, expressed of fluid and weighed to 0.1 mg. Data are reported as mg per 100 g body weight.

Radioimmunoassay of LH: Serum LH concentrations were determined in duplicate with a radioimmunoassay kit (reference preparation LH-RP-2) provided through the Pituitary Hormone Distribution Program of the NIADDK. The intra- and interassay coefficients of variation were 2.9 and 15.6, respectively.

Radioimmunoassay of Testosterone: Serum testosterone concentrations were determined in duplicate with a Coat-A-Count radioimmunoassay kit (Diagnostic Products; Los Angeles, CA).

Statistical treatment: The significance of difference among mean values for LH and peripheral tissues was determined by analysis of variance (ANOVA) and Student-Newman-Keuls (SNK) tests. The level of significance for both tests was 0.05.

RESULTS AND DISCUSSION

In Experiments 1 and 2, in which DMSO served as the drug vehicle, indications of drug insolubility upon injection were observed, i.e. respiratory distress accompanied by lesioning of the lungs, regardless of the rate of injection or infusion. In an effort to increase water solubility of the steroids, T-CDS$_1$ and TP were solubilized in a HPCD in Experiment 3. The improvement in solubility for the T-CDS$_1$ suggests that a lower dose (10 mg/kg vs. 25 mg/kg) could be administered with, presumably, a diminished risk of toxicity to the animal. A 2.5-fold decrease in T-CDS$_1$ dosage resulted in a similar suppression of serum LH levels observed in the previous two experiments. An injection of T-CDS$_1$-HPCD resulted in a 50% decrease in serum LH by 24 hours and this suppression was observed through 3 days. Suppression of LH occured in animals treated with TP-HPCD at day 1 only.

Mild stimulation of the seminal vesicles by T-CDS$_1$-HPCD and of the ventral prostate gland by T-CDS$_1$-HPCD and TP-HPCD was observed at 7 days post-injection. As observed previously, the extent of stimulation by T-CDS$_1$-HPCD or TP-HPCD was minor relative to tissue weights observed in control (gonadally-intact) rats.

A 5.5-fold increase in serum testosterone was observed 1 day after rats were administered T-CDS$_1$-HPCD and serum testosterone remained elevated at day 3. However, testosterone levels returned to pre-injection levels 5 days after injection. At no time did TP-HPCD or HPCD induce an increase in serum testosterone.

These experiments offer support for the improved delivery of testosterone to the brain when the representative redox carrier drug, T-CDS$_1$, is complexed to the representative cyclodextrin, HPCD. The data show an equivalent suppression of LH by complexing T-CDS$_1$ to HPCD and lowering the effective single dose of T-CDS$_1$ by 2.5-fold. This finding implies that the dihydropyridine form of T-CDS$_1$ remains in solution in an aqueous medium (e.g. blood) for a longer time, thereby permitting improved passage of the drug through the blood-brain barrier. Earlier studies revealed that, when administered in a DMSO vehicle, T-CDS$_1$ probably precipitated in the blood (and lungs), causing respiratory distress and/or death in rats. No respiratory distress or animal loss occured when T-CDS$_1$ was complexed with HPCD.

To quantitate the improvement provided by the representative cyclodextrin, HPCD, in lowering initial lung concentrations of redox carrier compounds compared to brain concentrations, another series of experiments was undertaken investigating the HPCD complex of E$_2$-CDS. These studies, which are detailed below, utilize a reversed-phase-high-performance liquid chromatographic method for the analysis of E$_2$-CDS and its oxidized quaternary metabolite E$_2$-Quat in biological fluids or tissues. The assay utilizes a precolumn enrichment technique and detects plasma levels down to 10 ng/mL E$_2$-Quat and 20 ng/mL E$_2$-CDS. Sample preparation is rapid and simple. Samples are homogenized with acetonitrile, centrifuged, and the supernatant is directly injected into the HPLC-system. A water-delivering pump injects the sample on a pre-column where the drug is concentrated. Mobile phase back-flushes the retained compound onto the analytical column. At the same time, another sample can be injected onto a second pre-column. This alternating pre-column sample enrichment technique allows the injection of large volumes up to 1800 μL.

EXPERIMENTAL SECTION

Materials: E$_2$-CDS, E$_2$-Quat and E$_2$-CDS-HPCD were synthesized as described previously. Steroids (estradiol and ethinyl estradiol) were obtained from Sigma Chemical Co. HPLC grade acetonitrile and distilled, deionized water were used for the preparation of mobile phases. All other reagents used were of analytical grade.

Instrumentation: The HPLC system consisted of a LDC/Milton Roy Constametric III high-pressure pump, a LDC/Milton Roy variable wavelength UV detector, a Perkin Elmer ISS-100 automatic injector equipped with a 2000 μL loop and a DuPont Zorbax ODS column, 15 cm×4.6 mm I.D. (6 μm particle size). Vydac guard columns (5 cm×3.2 mm I.D.), dry-packed with DuPont Zorbax ODS material, were used. Chromatograms were recorded on a Hewlett-Packard Model 3390A computing integrator at a chart speed of 0.2 cm/min. In addition, in the precolumn enrichment system, an enrichment injector (Rheodyne Model 7067-005) with two high pressure switching valves, pneumatically turned by a tandem actuator (Rheodyne Model 7163), was inserted between the autoinjector and the analytical column. Switching of the valves was controlled vai the autoinjector. This system also contained a Bodine Electric Co. RR/035 HPLC Solvent Pump for flushing the samples onto the enrichment columns.

Methods: Assay Conditions: direct on-line HPLC

Chromatographic conditions for the analysis of $E_2$-CDS, $E_2$-Quat and estradiol were developed. The optimal wavelength for all compounds was 224 nm, but $E_2$-CDS can also be detected at 360 nm due to the dihydropyridine structure. Although the absorptivity at this wavelength is only about half as high as it is at 224 nm, 360 nm was chosen as the analytical wavelength for $E_2$-CDS because of the increased selectivity. Different analytical columns were tested and mobile phases for a reversed phase chromatography of all three compounds were varied widely with respect to the ratio of aqueous and organic phase as well as buffer concentration and pH. No isocratic system could be found that would detect all three compounds within a reasonable retention time and with satisfying compactness and separation of peaks. Therefore, two different systems were used for analysis.

$E_2$-Quat and $E_2$: The optimal mobile phase was found to consist of acetonitrile/water 40:60 containing 0.03 M/L sodium salt of octanesulfonic acid and 0.003 M/L tetrabutylammonium phosphate. The pH was adjusted to pH 5–5.5. The flow rate was 1.5 mL/minutes and the peaks were recorded at 224 nm.

$E_2$-CDS: The mobile phase used for $E_2$-CDS analysis was acetonitrile/water 70:30 at a flow rate of 1.5 mL/minute. Absorbance was monitored at 360 nm.

Analysis of $E_2$, $E_2$-CDS and $E_2$-Quat by pre-column enrichment technique

The loss of sensitivity resulting from the dilution step in the procedure optimal for pretreatment of biological samples (see sample preparation without extraction) could be compensated for by developing an HPLC system that allows injection of large volumes. A suitable HPLC-method which has been described in the literature [Roth et al, J. Chromatogr. 222: 13–22 (1981)] is based on alternating pre-column sample enrichment. The procedure used herein was as follows: The sample containing the drug is injected with a first pump A, delivering pure water, onto one of two pre-columns, which are alternatingly connected with the injection system by two pneumatically driven valves. Provided a certain lipophilicity, the drug is retained and concentrated on the pre-column, while accompanying water soluble co-products like proteins are being washed out as long as water is pumped through the pre-column. This allows the direct injection of body fluids. After a certain enrichment time (6 and 8 minutes), simulataneous rotation of the two valves is induced, causing pre-column 1, where the injected drug has been absorbed, to be switched to the solvent stream of the second pump, B. Also, at this point, the recording integrator is started. Pump B delivers the mobile phase, necessary for separation and chromatography, and backflushes the sample from pre-column 1 onto the analytical column. Parallel to this process, pre-column 2 is switched to the water stream of pump A so that a sample can be injected and enriched while the previous one is being eluted (alternating mode). Volumes up to 1800 μL can be injected due to the concentration effect of the enrichment phase.

Chromatographic conditions: This system was applicable to the quantification of $E_2$, $E_2$-CDS and $E_2$-Quat. The mobile phase for $E_2$-CDS was: Acetonitrile/water 80:20 at a flow rate of 1.8 mL/minute. Optimal peak shape and retention time for $E_2$ and $E_2$-Quat were obtained with pump B delivering a mixture of acetonitrile/water 42:58 which contained 0.025 M/L sodium salt of 1-octanesulfonic acid and 0.003 M/L tetrabutylammonium phosphate. The pH was adjusted to pH 5, and the flow rate was 1.5 mL/minute.

Standard solutions and stability

Sample stock solutions of $E_2$-CDS, $E_2$-Quat, $E_2$ and ethinyl-$E_2$ containing each 50 μg/mL were prepared in acetonitrile. All solutions were stored at 6° C. For $E_2$-CDS, the stock solution was prepared freshly every 2 weeks. All other solutions were stable over a period of at least six months. Spiked plasma samples containing all four compounds were frozen at −20° C. and analyzed repeatedly at different time intervals. No loss of drug was found under these storage conditions during two months.

Dihydropyridine derivatives like $E_2$-CDS are known to be easily oxidized and very labile in acidic solutions. The stability of $E_2$-CDS was investigated under different conditions at room temperature. These studies were performed by diluting the $E_2$-CDS stock solution 1:2 with different solvents or solutions at different pH values and monitoring eventual peak height loss for 24 hours by use of a modification of the direct on-line HPLC method described above: If water in the $E_2$-CDS mobile phase is replaced by 0.05M phosphate buffer at pH 7 and if the detection wavelength is set to 224 nm, $E_2$-Quat can be detected simultaneously at 6.33 min. However, the peak is relatively broad. These conditions were used to determine the degree of $E_2$-CDS oxidation under the tested conditions.

Sample preparation

Extraction of $E_2$-Quat and $E_2$: Various extraction procedures from plasma were investigated under different conditions and with several solvents and solvent mixtures. Estrone could be used as an internal standard, but is known to be a potential metabolite of estradiol. Therefore, 17-β-ethinyl estradiol was chosen as internal standard. Its peak did not interfere with $E_2$, $E_2$-Quat or estrone. Without addition of an anion reagent, $E_2$-Quat could not be extracted from aqueous solutions. Optimal results were obtained after a single-step extraction of the drugs with potassium iodide as an ion-pairing reagent to facilitate quaternary salt extraction. The method applied was as follows: 200 μL of a saturated potassium iodide solution were added to 1 mL of spiked plasma. After vortexing for a few seconds, 10 mL of a mixture of chloroform/ethyl acetate 9:1 was added. The tubes were shaken for 10 minutes and then centrifuged for 10 minutes at 2000 rpm. The upper aqueous phase was discarded and the organic layer transferred to a clean tube to achieve complete separation from proteins and traces of aqueous phase. The organic layer was evaporated to dryness under nitrogen at 40° C. and reconstituted in 150 μL of mobile phase. 40 μL were injected into the HPLC system. Appropriate blanks were prepared accordingly.

Extraction of $E_2$-CDS: Plasma and water containing $E_2$-CDS were repeatedly extracted with different organic solvents like chloroform, hexane, toluene, benzene and ethyl acetate. It was impossible to extract $E_2$-CDS reproducibly from aqueous phases, since the compound was shown to deteriorate unreproducibly during evaporation, even at room temperature and in the presence of oxygen-free nitrogen. Therefore, the compound had to be analyzed from biological fluids without an extraction procedure.

Preparation of plasma and tissues for analysis of $E_2$-CDS and $E_2$-Quat without extraction: Using the HPLC technique with pre-column enrichment described above, drugs can be detected from directly injected plasma without sample preparation. However, when large volumes are injected, in order to obtain maximum sensitivity, it is desirable to remove proteins to a large extent prior to injection in order to prevent frequent pre-column packing. The procedure of deproteinization was chosen to be applicable for subsequent analysis of both $E_2$-CDS and $E_2$-Quat so that only one preparation step had to be performed.

Acidic precipitating agents, which remove proteins when only small volumes are added to biological fluids, could not be used because they induce degradative loss of $E_2$-CDS. Neutral or slightly basic aqueous reagents used efficiently for deproteinization like $ZnSO_4/NaOH$, $CuSO_4/Na_2SO_4$ or saturated $(NH_4)_2SO_4$ would be more ideal to be injected onto the enrichment columns than organic solvents. But all of these reagents were shown to absorb the water-insoluble $E_2$-CDS on the precipitate. Thus, the method of choice to avoid instability problems and at the same time keep all compounds in solution was deproteinization with acetonitrile.

To obtain these results, the following sample preparation procedures were used for plasma and tissues: Plasma: 0.6 mL plasma was added to 1.2 mL acetonitrile. The mixture was vortexed for 5 seconds and allowed to stand for 10 minutes at room temperature, vortexed again and centrifuged for 10 minutes at 2000 rpm. 1000–1500 μL of the supernatant was injected into the pre-column enrichment system. Tissue (e.g. brain): 1 mL of water was added to one rat brain and the organ was thoroughly meshed. After sonication for 2 minutes and centrifugation at 2000 rpm for 10 minutes, the supernatant (1000–1500 μL) was injected into the enrichment system.

Animal Studies

In a first experiment, 15 mg/kg $E_2$-CDS dissolved in dimethylsulfoxide (DMSO) were administered intravenously to conscious, restrained male Sprague-Dawley rats weighing 190–300 g each. Animals were sacrificed in groups of 4 at 5, 15 and 30 minutes and at 1, 2, 4, 8, 24 and 48 hours after drug injection. Trunk blood was collected into heparinized tubes and plasma obtained and immediately frozen at $-20°$ C. until analysis. Organs were dissected and placed on dry ice within 2 minutes of death and stored at $-20°$ C. for later analysis by the HPLC method described above.

In a second experiment, the same procedure as above was followed, except that 5 mg/kg of $E_2$-CDS were administered as a complex with hydroxypropyl-$\beta$-cyclodextrin (HPCD) in water. The 5 mg/kg dose of $E_2$-CDS was delivered in 1 mL of aqueous solution containing approximately 20% w/v HPCD (prepared by dissolving a freeze-dried complex containing 3.5 mg $E_2$-CDS per gram in aqueous 20% HPCD, the freeze-dried complex having been prepared from a 50% solution of $E_2$-CDS in HPCD having 5.1 degrees of substitution).

Results and Discussion

Figure 1A:
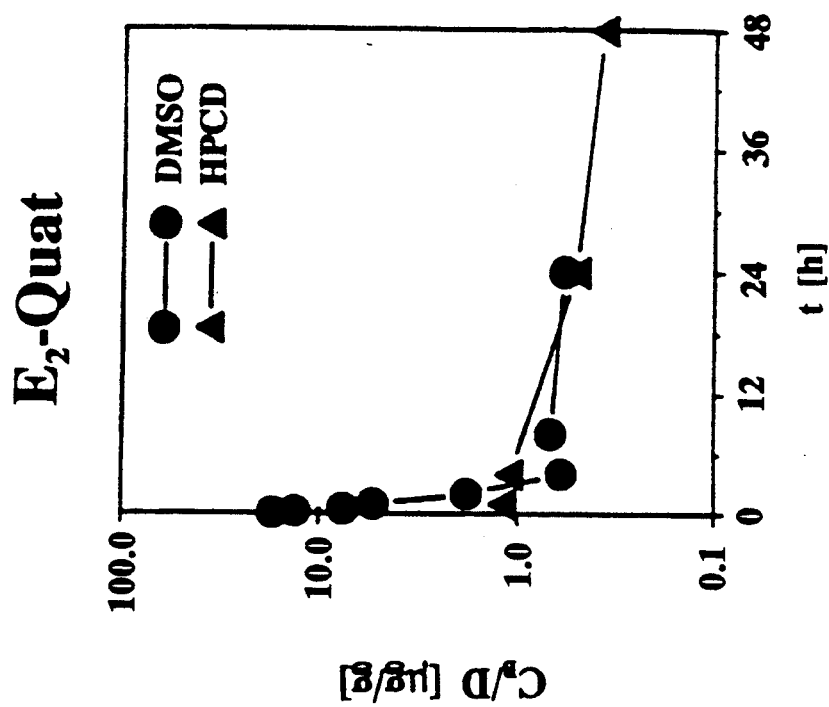
Figure 2:
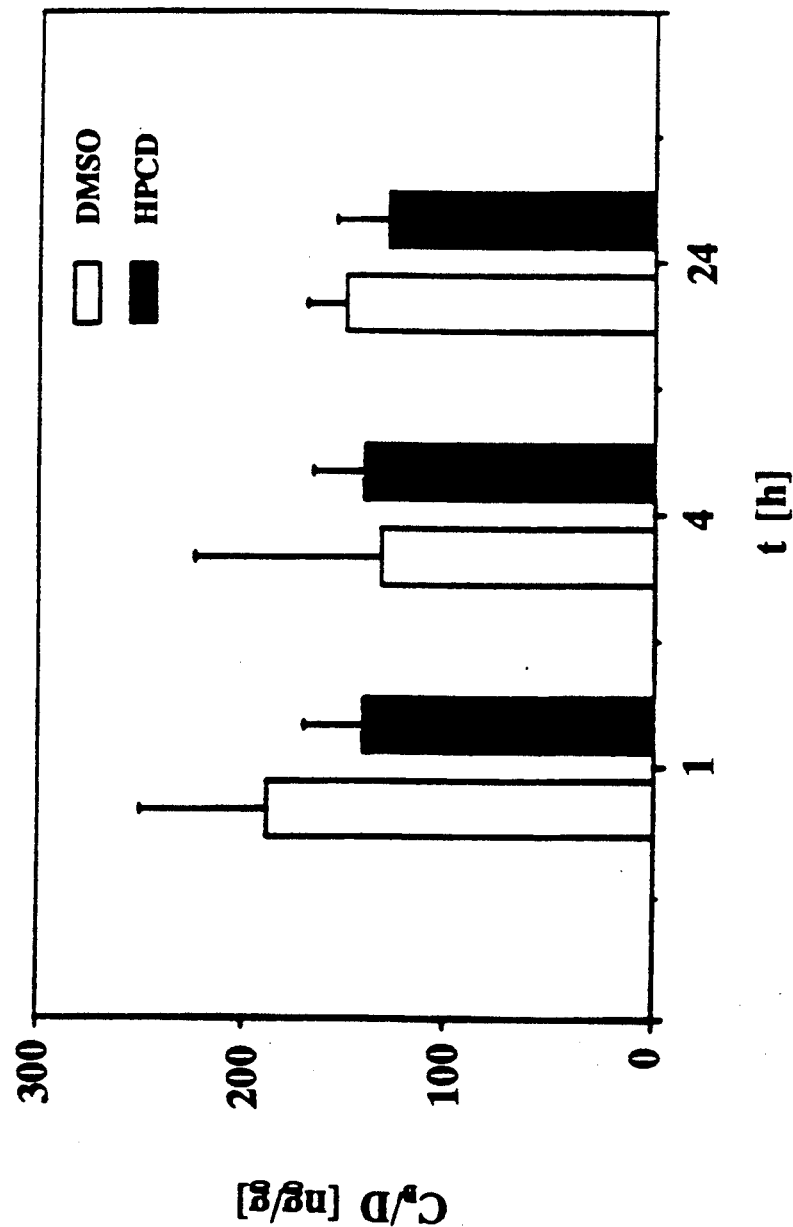
FIG. 2 is a bar graph illustrating, at selected time points, the concentrations of the quaternary cation, E$_2$Q$^+$ or Quat, in the brain in ng per gram dose, following systemic administration to rats of either 15 mg/kg E$_2$-CDS in dimethylsulfoxide ($\square$) or 5 mg/kg E$_2$-CDS inclusion complex with hydroxypropyl-$\beta$-cyclodextrin ($\blacksquare$) in water, corrected for dose.

The results are depicted in FIG. 1a, FIG. 1b FIG. 2. FIGS. 1a and 1b consist of a pair of semi-logarithmic plots comparing the concentrations in lung tissue in μg per g dose ($C_B/D$) of $E_2$-CDS in FIG. 1a and of $E_2$-Quat in FIG. 1b, corrected for dose. It can be seen from FIGS. 1a and 1b that when $E_2$-CDS was administered in DMSO, initial lung concentrations (i.e. concentrations within the first hour after drug injection) of both $E_2$-CDS and $E_2$-Quat were significantly (more than ten-fold) higher than the initial lung concentrations observed when $E_2$-CDS was administered as a complex with HPCD in water. The corresponding levels of $E_2$-Quat in brain tissue, also corrected for dose, are given in FIG. 2 in the form of a bar graph depicting the brain levels in ng per g dose ($C_B/D$) at selected time points. It can be seen that the brain levels after 1 hour are not significantly different for administration as HPCD complex in water as compared to administration in DMSO. Clearly, then, the carrier-drug can be administered as a complex with a selected cyclodextrin as defined herein, such as HPCD, in water and still achieve the brain levels needed to produce the desired biological effect, while avoiding the high initial lung concentrations responsible for respiratory distress and dysnia.

Complexation with 2-hydroxypropyl-$\beta$-cyclodextrin (HPCD) or other selected cyclodextrin derivative as defined herein has been found to be particularly advantageous in that it stabilizes the dihydropyridine redox systems. A direct comparison of stabilities in aqueous solution is, of course, not possible because of the low solubility of the dihydropyridine redox system drugs in water; for example, the solubility of $E_2$-CDS in water is only 0.0002 mg/mL. The $E_2$-CDS-HPCD complex contains about 40 mg of $E_2$-CDS/g and easily gives aqueous solutions containing 5 mg $E_2$-CDS/mL at 20% w/v cyclodextrin. Thus, complexation affords a 25,000-fold increase in aqueous solubility of $E_2$-CDS. The half-life of $E_2$-CDS in such a solution at room temperature in the dark is about 12.5 days (rate: $0.0554 \pm 0.0047 d^{-1}$).

Since the dihydropyridine redox system drugs are especially prone to oxidative degradation, a study was undertaken to quantitate the effect of a cyclodextrin derivative intended for use herein, e.g. HPCD, on the rate of oxidation of these drugs. A representative carrier-drug, $E_2$-CDS, was selected for this study.

The rate of ferricyanide-mediated oxidation of $E_2$-CDS was determined using a previously published method (Okamoto et al, *J. Chem. Soc. Chem. Comm.*, 1977, 181). In this procedure, 27.5 μL of a $5 \times 10^{-3}$M solution of $E_2$-CDS in acetonitrile was added to 2.75 mL of a solution containing $1 \times 10^{-4}$M $Fe(CN)_6^{-4}$, 0.06M $K^+$, 0.001M $Fe(CN)_6^{-3}$. All solutions were made using water which had been boiled for 30 minutes and cooled while a stream of pyrogallol-scrubbed nitrogen passed through it. The $E_2$-CDS was introduced via a syringe to the solution which was maintained at 37° C. in a thermostated cell holder and contained in an anaerobic screw-top cuvette. The cuvette had a Teflon-lined septum through which the compound was injected. For a given concentration of ferricyanide ions ($6 \times 10^{-4}$ to $8 \times 10^{-3}$M), the rate of disappearance of the $E_2$-CDS was determined. This was done by calculating the decrease in the absorbance band at 360 nm ($\pm 10$ nm)

subtracted from base line absorbance (500±10 nm). A plot of the 1 n, [Abs] versus time gave a slope for the pseudo-first-order rate constant. This was done at several different ferricyanide ion concentrations. The obtained first-order rate constants were then plotted as a function of ferricyanide ion concentration generating a slope from which the second order rate constant ($k_0$ $s^{-1}M^{-1}$) was obtained. In examining the effect of 2-hydroxypropyl-$\beta$-cyclodextrin on the rate of $E_2$-CDS oxidation, solutions containing the HPCD as well as those ions present in the first phase of the experiment were prepared. The second order constant was derived for each cyclodextrin concentration and a plot developed. The results show that the cyclodextrin dramatically slowed the rate of oxidation. There appears to be a saturation effect in that after 2% w/v, not much change in rate is evident. The second order rate of oxidation is inhibited by 42% at 0.5% w/v cyclodextrin, 60% at 1.0% w/v, 81% at 2% cyclodextrin and at 5-20% a value of approximately 90% reduction in the rate was obtained.

From the foregoing, it is apparent that formulation with a representative cyclodextrin derivative as defined herein has overcome problems associated with administration of the reduced lipoidal form of dihydropyridine ⇌ pyridinium salt redox carrier systems for brain-targeted drug delivery. In particular, it has been found that administration of aqueous parenteral carrier-drug formulations comprising from about 20 to about 50% w/w or w/v of the selected cyclodextrin, preferably hydroxypropyl-$\beta$-cyclodextrin, surprisingly changes the distribution of the drug and avoids the lung precipitation problems associated with organic solvents, leading to decreased toxicity. The advantageous time element, which could not have been predicted, is such that there is sufficient time after injection but before separation of the drug from the cyclodextrin to prevent aggregation of the drug molecules (i.e. precipitation of drug aggregates) in the lungs and other organs such as the liver, and yet the time is short enough to allow timely break-up of the drug/cyclodextrin, affording facile distribution of the drug molecules so as to achieve the desired pharmacological effect. Other lipophilic/hydrophic and/or water-labile drugs which have heretofor been formulated for parenteral administration only in organic solvents, and/or which have simply been unavailable in parenteral form, share to various extents the same sort of problems encountered with the redox carrier system and benefit from the same improved distribution and advantageous time element discussed above. Drugs which are particularly useful in the parenteral compositions and methods of the present invention are those which are relatively insoluble in water but whose water solubility can be substantially improved by formulation with 20 to 50% of the selected cyclodextrin, e.g. HPCD, in water. These characteristics can be determined by simple experiments of the type described below for representative drugs.

Apparatus

UV spectra were recorded on a Cary 210 double-beam spectrophotometer (Varian, Palo Alto, Calif.). High pressure liquid chromatography was performed on a component system consisting of Micromeritics 728 autosampler, Beckman 112 solvent delivery module, Waters Lambda-Max Model 481 LC spectrophotometer, and Fisher Recordall series 5000 recorder. The samples were sonicated in a Fisher Bransonic ultrasonic cleaner and equilibrated in a MGW Lauda constant temperature water bath.

Solubility Studies

Phase-solubility experiments were conducted by adding excess amounts of the drug to be tested to aqueous solutions containing various amounts of 2-hydroxypropyl-$\beta$-cyclodextrin and sonicating the mixture for one hour. After equilibration in a 25°±1° C. water bath in the dark for at least 48 hours, aliquots of the mixtures were filtered through 0.45 $\mu$m membrane filters, diluted and the drug concentrations measured by reversed-phase HPLC methods.

For comparison, the solubilities of the drugs in water were also detemined.

HPLC Methods

Chlordiazepoxide
Wavelength: 245 nm
Column: Waters $\mu$Bondapak CN, 3.9 mm (i.d.)×30 cm
Mobile phase: acetonitrile, acetic acid, water (60:1:39) containing 0.1% 1-hexasulfonic acid, sodium salt
Flow rate: 2.00 mL/min. Retention time: 4.0 min.

Dexamethasone
Wavelength: 263 nm
Column: ASI C18, 10 $\mu$m, 3.9 mm (i.d.)×30 cm
Mobile phase: acetonitrile, water (55:45)
Flow rate: 1.00 mL/min. Retention time: 3.6 min.

Diazepam
Wavelength: 241 nm
Column: Waters $\mu$Bondapak CN, 3.9 mm (i.d.)×30 cm
Mobile phase: acetonitrile, water (6:4)
Flow rate: 2.00 mL/min. Retention time: 3.2 min.

17$\beta$-Estradiol
Wavelength: 280 nm
Column: ASI C18, 10 $\mu$m, 3.9 mm (i.d.)×30 cm
Mobile phase: acetonitrile, water (55:45)
Flow rate: 2.00 mL/min. Retention time: 4.4 min.

17$\alpha$-Ethynylestradiol
Wavelength: 248 nm
Column: Fisher Resolvex C18, 4.6 mm (i.d.)×25 cm
Mobile phase: acetonitrile, water (6:4)
Flow rate: 1.50 mL/min. Retention time: 4.4 min.

Ethynylestradiol 3-methyl ether
Wavelength: 248 nm
Column: Fisher Resolvex C18, 4.6 mm (i.d.)×25 cm
Mobile phase: acetonitrile, water (7:3)
Flow rate: 2.00 mL/min. Retention time: 6.0 min.

Medazepam
Wavelength: 253 nm
Column: Waters $\mu$Bondapak CN, 3.9 mm (i.d.)×30 cm
Mobile phase: acetonitrile, acetic acid, water (60:1:39) containing 0.1% 1-hexanesulfonic acid, sodium salt
Flow rate: 2.00 mL/min. Retention time: 2.8 min.

Methotrexate
Wavelength: 308 nm
Column: Fisher Resolvex C18, 4.6 mm (i.d.)×25 cm
Mobile phase: methanol, acetic acid, water (50:1:49) containing 0.1% 1-octanesulfonic acid, sodium salt
Flow rate: 2.00 mL/min. Retention time: 3.5 min.

Norethindrone
Wavelength: 240 nm
Column: Fisher Resolvex C18, 4.6 mm (i.d.)×25 cm
Mobile phase: acetonitrile, water (6:4)
Flow rate: 1.50 mL/min. Retention time: 3.6 min.
Norethindrone acetate
Wavelength: 240 nm
Column: Fisher Resolvex C18, 4.6 mm (i.d.)×25 cm
Mobile phase: acetonitrile, water (7:3)
Flow rate: 2.00 mL/min. Retention time: 5.0 min.

D(−)-Norgestrel
Wavelength: 241 nm
Column: Fisher REsolvex C18, 4.6 mm (i.d.)×25 cm
Mobile phase: acetonitrile, water (7:3)
Flow rate: 2.00 mL/min. Retention time: 3.4 min.

Oxazepam
Wavelength: 230 nm
Column: Waters μBondapak CN, 3.9 mm (i.d.)×30 cm
Mobile phase: acetonitrile, water (35:65)
Flow rate: 2.00 mL/min. Retention time: 2.6 min.

Phenytoin
Wavelength: 258 nm
Column: Fisher Resolvex C18, 4.6 mm (i.d.)×25 cm
Mobile phase: acetonitrile, water (55:45)
Flow rate: 2.00 mL/min. Retention time: 1.6 min.

all-trans-Retinol
Wavelength: 325 nm
Column: Waters μBondapak C18, 10 μm, 3.9 mm (i.d.)×30 cm
Mobile phase: acetonitrile, water (55:45)
Flow rate: 1.00 mL/min. Retention time: 5.8 min.

Results

TABLE III

Solubilization of Drugs by 2-Hydroxypropyl-β-Cyclodextrin in Aqueous Solution at 25 ± 1° C.

| Drug[a] | Solubility in water (mg/mL) | Solubility in HPCD - Water Solution - Conc. of HPCD | Solubility in HPCD - Water Solution - Solubility (mg/mL) | Increase in Solubility (HPCD/water) |
|---|---|---|---|---|
| Chlordiazepoxide | 0.01[b] | 50% w/w | 147.8 | ~15,000 |
| Dexamethasone | 0.008 | 50% w/w | 44.3 | ~5,500 |
| Diazepam | 0.05[b] | 50% w/w | 7.4 | ~150 |
| 17β-Estradiol | 0.004[b] | 50% w/w | 40.5 | ~10,000 |
| 17α-Ethynylestradiol | 0.008 | 50% w/w | 68.2 | ~8,500 |
| Ethynylestradiol 3-methyl ether | 0.001 | 50% w/w | 13.3 | ~13,000 |
| Medazepam (pH 7.5) | 0.01 | 50% w/w | 8.3 | ~850 |
| Methotrexate (pH 7.6) | 0.045 | 50% w/w | 10.0 | ~200 |
| Norethindrone | 0.005 | 50% w/w | 19.0 | ~4,000 |
| Norethindrone acetate | 0.0002 | 50% w/w | 19.5 | ~97,500 |
| D(−)-Norgestrel | 0.002 | 50% w/w | 4.9 | ~2,500 |
| Oxazepam | 0.03 | 50% w/w | 4.2 | ~150 |
| Phenytoin | 0.02 | 50% w/w | 9.3 | ~450 |
| All-trans-Retinol | 0.001 | 50% w/w | 4.6 | ~4,600 |

[a]pH of the 2HPCD solution given when monitored.
[b]Literature values

TABLE IV

Solubilization of Drugs by 25% w/v Aqueous Hydroxypropyl-β-Cyclodextrin at 25 ± 1° C.

| Drug | Solubility (mg/mL) |
|---|---|
| Dexamethasone | 24.18 |
| 17β-Estradiol | 19.13 |
| 17α-Ethynylestradiol | 34.47 |
| 17α-Ethynylestradiol 3-methyl ether | 7.13 |
| Norethindrone | 9.13 |
| Norethindrone acetate | 9.41 |
| D(−)-Norgestrel | 2.19 |

Apparatus

UV spectra were taken on a Perkin-Elmer 550 SE double-beam spectrophotometer. The high pressure liquid chromatography was performed on a component system consisting of Rheodyne 7125 injector, LKB 2150 HPLC pump, LKB 2138 Lichrosorb RP18 10 mm column (4×250 mm), LKB 2138 uvicord 5 detector and Omniscribe recorder. The samples were sonicated in a Kerry Ultrasonic bath and equilibrated in Tecam TE-7 Tempette constant temperature water bath.

Solubility Studies

Phase-solubility experiments were conducted by adding excess amounts of the drug to be tested to aqueous solutions containing various amounts of 2-hydroxypropyl-β-cyclodextrin (HPCD) and sonicating the mixtures for up to four hours. After equilibration in a 30.0±0.2° C. water bath in the dark for up to 72 hours, aliquots of the mixtures were filtered through 0.45 Mm membrane filters, diluted and the drug concentration determined by HPLC or UV methods. The sonication and equilibration time was kept at a minimum because of the instability of the drugs.

HPLC Methods

Chlorambucil
Wavelength: 245 nm
Mobile phase: acetonitrile, acetic acid, water (45:1:54)
Flow rate: 2.00 mL/min.
Retention time: 4.4 min.

Lomustine
Wavelength: 254 nm
Mobile phase: methanol, water (7:3)
Flow rate: 2.00 mL/min.
Retention time: 3.6 min.

Melphalan
Wavelength: 254 nm
Mobile phase: Methanol, acetic acid, water (60:1:39)+0.19% 1-pentanesulfonic acid, sodium salt.
Flow rate: 2.00 mL/min.
Retention time: 3.6 min.

Results

Chlorambucil
The preliminary experiment indicated that the solubility was about 30 mg/g in 50% w/w HPCD/H$_2$O solution (sonication for 30 min. followed by equilibration at 30° for 4 hours). The drug is almost insoluble in water and the p.o. dose is about 100 mg/kg/day. Further experiments were done and the results are shown in TABLE V. Significant degradation occurred during the experiments (3.5 days).

Lomustine

The initial experiment indicated that the solubility was about 12 mg/g in 50% w/w HPCD/H$_2$O solution. The results of the follow-up experiments are shown in TABLE VI. Some degradation occurred.

Melphalan

The initial experiment indicated that the solubility was about 21.9 mg/g in 50% w/w HPCD/H$_2$O solution (sonication for one hour followed by equilibration at 30° for 4 hours). The results of the follow-up experiments are shown in TABLE VII. Some degradation occurred.

TABLE V

Solubility of chlorambucil in aqueous solutions of 2-hydroxypropyl-β-cyclodextrin (HPCD) at 30.0 ± 0.2° C.

| % w/v HPCD | Solubility (mg/mL) (1) | (2) |
|---|---|---|
| 0 | 0.01 | 0.41 |
| 1 | 0.74 | 0.55 |
| 2 | 1.48 | 0.84 |
| 3 | 2.37 | 0.68 |
| 4 | 3.22 | 1.50 |
| 5 | 1.46 | 1.80 |
| 7 | 2.71 | 3.76 |
| 10 | 4.96 | 5.20 |
| 15 | 6.36 | 7.60 |
| 20 | 8.49 | 13.09 |
| 25 | 8.85 | 18.40 |

(1) Sonication for 45 min. followed by equilibration at 30° for 3 hours.
(2) Sonication for 4 hours followed by equilibration at 30° for 3.5 days.

TABLE VI

Solubility of lomustine in aqueous HPCD solutions at 30 ± 0.2° C.

| % w/w HPCD | Solubility (mg/mL)* |
|---|---|
| 0 | 0.18 |
| 1 | 0.38 |
| 5 | 1.68 |
| 10 | 3.33 |
| 15 | 6.26 |
| 20 | 8.44 |
| 25 | 8.9 |

*The figures shown are average numbers from up to four experiments.

TABLE VII

Solubility of melphalan in aqueous HPCD solutions at 30.0 ± 0.2° C.

| % w/v HPCD | Solubility (mg/mL)* |
|---|---|
| 0 | 1.26 |
| 1 | 4.16 |
| 2 | 4.3 |
| 3 | 6.24 |
| 4 | 7.14 |
| 5 | 7.2 |
| 7 | 10.5 |
| 10 | 13.37 |
| 15 | 17.64 |
| 20 | 24.75 |
| 25 | 31.36 |

*The figures shown are average values of several experiments.

TABLE VIII

| | Chlorambucil | Lomustine | Melphalan |
|---|---|---|---|
| p.o. dose,* | 0.1–0.2 mg/kg** | 130 mg/m$^2$*** | 2–35 mg** |
| i.v. dose,* | — | — | — |
| solubility in water (mg/g) | 0.41 | 0.18 | 1.26 |
| solubility in 25% w/v HPCD (mg/g) | 18.40 | 8.9 | 31.36 |
| solubility in 20% w/v HPCD | 13.09 | 8.44 | 24.75 |

TABLE VIII-continued

| | Chlorambucil | Lomustine | Melphalan |
|---|---|---|---|
| (mg/g) increase: water/25% HPCD | 44.88 | 49.44 | 24.89 |

*From the Icelandic drug manual.
**Daily dose.
***Every 6 weeks.

Solubility Studies

Phase-solubility experiments were conducted by adding excess amounts of alfaxalone to phosphate buffer solutions containing 20% w/v of selected cyclodextrins and sonicating the mixtures for at least one hour. (The phosphate buffer solution was prepared by dissolving 1.183 g KH$_2$PO$_4$ and 4.320 g Na$_2$HPO$_4$ in water and diluting to 1 liter.) The mixtures were filtered through 0.45 μm Millipore syringe filters and diluted and the drug concentrations were measured by reversed phase HPLC methods. Alfaxalone itself is virtually insoluble in water.

HPLC Methods for Alfaxalone

Wavelength: 294 nm
Mobile phase: methanol:water (65:35)
Flow rate: 1.5 mL/min.
Retention tiem: ~14 min.

The results of these studies are summarized in TABLE IX below.

TABLE IX

Solubilization of Alfaxalone by 20% w/v Solutions of Selected Cyclodextrins at Room Temperature

| Cyclodextrin | Solubility (mg/mL) |
|---|---|
| maltosyl-β-cyclodextrin mixture | 20.02 |
| hydroxypropyl-γ-cyclodextrin | 18.41 |
| hydroxypropyl-γ-cyclodextrin | 15.11 |
| hydroxypropyl-β-cyclodextrin | 22.83 |
| hydroxypropyl-β-cyclodextrin | 24.42 |

The following examples illustrate the preparation of preferred reduced, dihydropyridine⇌pyridinium salt redox carrier systems for brain-targeted drug delivery which are contemplated for use in accord with the present invention and which have not been specifically described in publications to date.

EXAMPLE 1

Preparation of N-Nicotinoyldopamine

To a pyridine solution containing 11.7 g (0.05 mol) dopamine hydrobromide and 6.15 g (0.05 mol) nicotinic acid at 0° C. were added 10.3 g (0.05 mol) dicyclohexylcarbodiimide (DCC). The reaction mixture was stirred at room temperature for 24 hours and the formed dicyclohexylurea was removed by filtration. The pyridine was removed in vacuo and the residue was crystallized from water at 0° C. The product was isolated by filtration and dried over phosphorous pentoxide. Recrystallization from isopropanol gave 9.0 g (0.035 mol), 70% N-nicotinoyldopamine, m.p. 159°–162° C.; aqueous solution of the compound gave a green color with Fe$^{+3}$ and reduced AgNO$_3$; IR (KBr) 3300, 2960, 1725, 1630, 1590, 1520, 1430, 1290, 1190, 1115, 720 and 710 cm$^{-1}$; NMR (d$_6$-DMSO) δ9.25–6.25 (m, 7H), 3.3 (m, 2H) and 2.65 (m, 2H) ppm. Anal. (C$_{14}$H$_{14}$N$_2$O$_3$) C, H, N.

EXAMPLE 2

Preparation of
1-Methyl-3-{N-[β-(3,4-dihydroxyphenyl)-ethyl]}carbamoylpyridinium iodide To a solution of 2 g (7.7 mmol) of N-nicotinoyldopamine in 40 mL of dry methanol were added 2.5 g (17.6 mmol) of methyl iodide. The reaction mixture was refluxed with stirring for 6 hours. Methyl iodide (1.5 g, 1.05 mmol) was added and refluxing was continued overnight. Methanol was removed and ethyl acetate was added, affording yellowish crystals of the desired product. Yield 2.4 g (77%), m.p. 173°–174° C.

EXAMPLE 3

Preparation of
1-Methyl-3-{N-[[β-[3,4-bis(isobutyryloxy)phenyl]ethyl]]}carbamoylpyridinium trifluoroacetate To an ice-cold solution of the product of Example 2 (3 g, 7.5 mmol) in 30 mL of trifluoroacetic acid, isobutyryl chloride (2.4 g, 22.5 mmol) was added slowly, with stirring. Stirring was continued overnight at room temperature. Trifluoroacetic acid was evaporated under vacuum and the residue was crystallized from ethyl ether:hexane (3:1). Yield 1.2 g (30.4%), m.p. 87°–91° C.

EXAMPLE 4

Preparation of
1-Methyl-3-{N-[[β-[3,4-bis(isobutyryloxy)phenyl]ethyl]]}carbamoyl-1,4-dihydropyridine A solution of 0.55 g (1 mmol) of 1-methyl-3-{N-[[β-[3,4-bis(isobutyryloxy)phenyl]ethyl]]}carbamoylpyridinium trifluoroacetate in 50 mL of deaerated water containing 10 mL of methanol was extracted three times with 30 mL portions of ether. To the resultant aqueous solution were added NaHCO$_3$ (0.25 g, 3 mmol) and 50 mL of ethyl ether and the mixture was kept under nitrogen. To this ice-cold mixture was added sodium dithionite (0.52 g, 3 mmol) and the mixture was stirred vigorously for 30 minutes. The ether layer was separated and the aqueous layer was extracted twice with ether. The combined ether extracts were washed with water and dried over sodium sulfate. Ether was removed under vacuum, leaving an oily product. NMR analysis confirmed that the product had the structural formula:

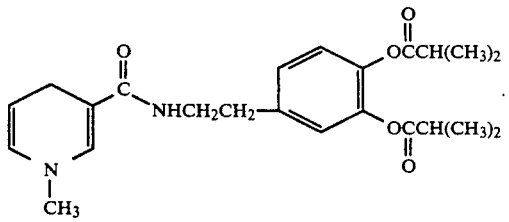

EXAMPLE 5

Preparation of
5,5-Diphenyl-3-hydroxymethyl-2,4-imidazolidinedione

Phenytoin (5 g, 0.02 mol) was suspended in 180 mL of water; 20 mL of formaldehyde (37% solution) and 0.25 g K$_2$CO$_3$ were added and the mixture was stirred at 25°–30° C. for 24 hours. The white solid which formed was removed by filtration and washed repeatedly with a 3% solution of formaldehyde, then air-dried for 3 to 4 hours and over P$_2$O$_5$ in a vacuum dessicator. Yield 91–93%, m.p. 185°–189° C. Anal. calc. for C$_{16}$H$_{14}$N$_2$O$_3$: C, 68.07; H, 5.00; N, 9.93. Found: C, 67.97; H, 5.05; N, 9.93. The product had the formula:

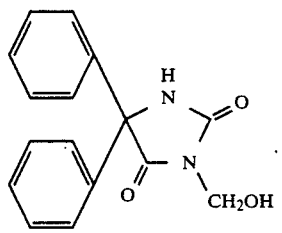

EXAMPLE 6

Preparation of
5,5-Diphenyl-3-[(3'-pyridyl)carbonyloxymethyl]-2,4-imidazolidinedione The product of Example 5 (3.00 g, 0.011 mol) was dissolved in 150 mL of dry pyridine, then nicotinic anhydride (4.25 g, 0.019 mol) was added. The resultant solution was stirred at room temperature (25°–30° C.), under dry conditions, for 40 hours. The solution was poured into 2.5 L of water and the resultant white solid was removed by filtration, washed well with water and dried over P$_2$O$_5$ in a vacuum dessicator. 95% yield, m.p. 178°–182° C. Anal calc. for C$_{22}$H$_{17}$N$_3$O$_4$: C, 68.21; H, 4.42; N, 10.85. Found: C, 68.12; H, 4.43; N, 10.83. The product had the formula:

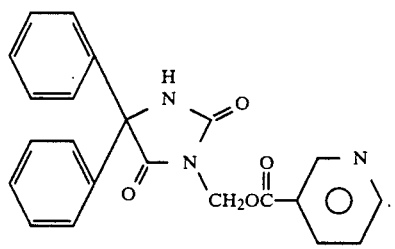

EXAMPLE 7

Preparation of
5,5-Diphenyl-3-[(1'-methyl-3'-pyridinium)carbonyloxymethyl]-2,4-imidazolidinedione iodide The product of Example 6 (0.5 g, 0.0013 mol) was dissolved in 50 mL of acetonitrile, then 0.3 mL of methyl iodide was added and the reaction mixture was maintained at room temperature for 6 days. The solvent was removed by vacuum distillation and ethyl ether was added to the residue. The ether solution was refrigerated for 2 hours, then the yellow, hygroscopic crystals which formed were dried over P$_2$O$_5$ in a vacuum dessicator, giving the desired product in 85% yield. UV and H$^1$NMR spectra confirmed that the product had the structure:

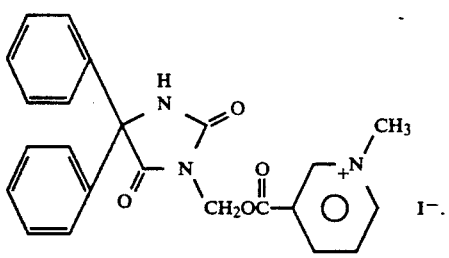

Repeating the above procedure in nitromethane at a 50°-70° C. bath temperature using excess methyl iodide, added gradually, for 5 to 6 hours, afforded the same product in nearly quantitative yield.

EXAMPLE 8

Preparation of 5,5-Diphenyl-3-[(1'-methyl-1',4'-dihydropyridin-3'-yl)carbonyloxymethyl]-2,4-imidazolidinedione The quaternary salt obtained in Example 7 (0.4 g, 0.0008 mol) was dissolved in 40 mL of water, 3 mL of methanol and 15 mL of ethyl acetate. The reaction mixture was cooled to 0° to 5° C. and deaerated, then sodium bicarbonate (0.39 g, 0.0046 mol) and sodium dithionite (0.54 g, 0.0032 mol) were added. The mixture was stirred under nitrogen at 0°-5° C. for 35 minutes. The organic layer was removed and the aqueous layer was extracted twice with 15 mL portions of ethyl acetate and the organic solutions were extracted with 10 mL of cold deaerated water. After drying over $Na_2SO_4$, the solvent was removed by vacuum distillation and the oily yellow solid was crystallized by addition of ether. Yield 70%. UV and $H^1NMR$ analyses confirmed that the product had the formula:

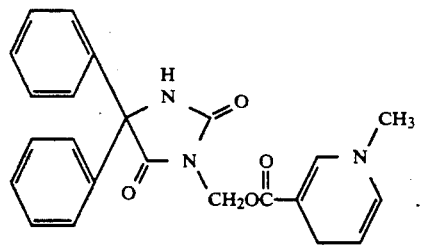

EXAMPLE 9

Preparation of 3-Bromoacetyloxymethyl-5,5-diphenyl-2,4-imidazolidinedione 5,5-Diphenyl-3-hydroxymethyl-2,4-imidazolidinedione (2 g, 0.0071 mol) was dissolved in bromoacetylchloride (15 g, 8 mL, 0.096 mol) by heating in an oil bath (70°-80° C. bath temperature) for about 15 minutes, until the formation of HCl ceased. The mixture was cooled and 30 mL of ethyl ether were added. White crystals formed. The mixture was cooled to 0° C., then the crystals were removed by filtration and dried over $P_2O_5$. Yield: 2.15 g (75%), m.p. 179°-183° C. Anal. calc. for $C_{18}H_{15}N_2O_4Br$: C, 53.61, H, 3.75; N, 6.95; Br, 19.82. Found: C, 53.6; H, 3.79; N, 6.92; Br, 19.9. The product had the formula:

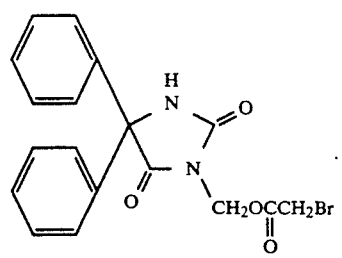

EXAMPLE 10

Preparation of 3-(3'-Bromopropionyl)oxymethyl-5,5-diphenyl-2,4-imidazolidinedione 5,5-Diphenyl-3-hydroxymethyl-2,4-imidazolidinedione (5 g, 0.018 mol) was reacted according to the procedure of Example 9 with 3-bromopropionyl chloride (6.8 g, 0.04 mol, 4 mL) using a bath temperature of 100° C. A white crystalline product was obtained in 65% yield (4.9 g), m.p. 133°-134° C. Anal. calc. for $C_{19}H_{17}N_2O_4Br$: C, 54.69; H, 4.11; N, 6.72; Br, 19.15. Found: C, 54.79; H, 4.12; N, 6.69; Br, 19.25. The product had the formula:

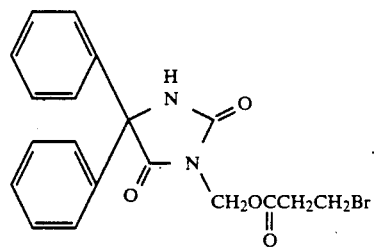

EXAMPLE 11

Preparation of 3-(2'-Bromopropionyl)oxymethyl-5,5-diphenyl-2,4-imidazolidinedione 5,5-Diphenyl-3-hydroxymethyl-2,4-imidazolidinedione (2 g, 0.0071 mol) was dissolved in 2-bromopropionyl chloride (8.5 g, 5 mL, 0.05 mol) by heating for 30 minutes on a 100°-110° C. oil bath. The reaction mixture was cooled, 20 mL of ethyl ether were added, and the resultant solution was extracted with aqueous potassium carbonate, dried and then crystallized. The product was obtained as a solid white substance (1 g, 34%), m.p. 112°-115° C. Anal. calc. for $C_{19}H_{17}N_2O_4Br$: C, 54.69; H, 4.11; N, 6.72; Br, 19.15. Found: C, 54.77; H, 4.15; N, 6.69; Br, 19.25. The product had the formula:

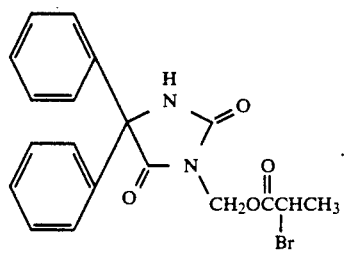

EXAMPLE 12

Preparation of 3-(3'-Carbamoyl-1'-pyridinium)acetyloxymethyl-5,5-diphenyl-2,4-imidazolidinedione bromide The product of Example 9 (2.02 g, 0.005 mol) dissolved in 15 mL of nitromethane was mixed with nicotinamide (0.61 g, 0.005 mol). The solution was stirred on a 90°–100° C. temperature oil bath for 2 hours. The mixture was cooled to 60°–70° C. and the white crystals which had formed were removed by filtration and washed with nitromethane. Yield 61% (1.65 g), m.p. 193°–197° C. (dec). Anal. calc. for $C_{24}H_{21}N_4O_5Br$: C, 54.87; H, 4.03; N, 10.67; Br, 15.21. Found: C, 54.70; H, 4.05; N, 10.64; Br, 15.25. The product had the formula:

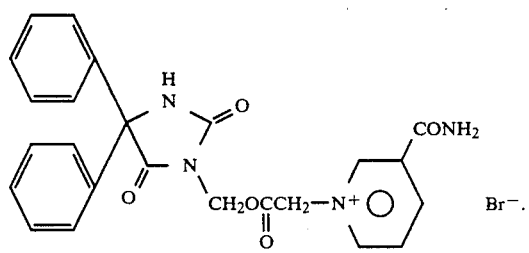

EXAMPLE 13

Preparation of 3-[3'-(3''-Carbamoyl-1''-pyridinium)-propionyloxymethyl]-5,5-diphenyl-2,4-imidazolidinedione bromide The product of Example 10 (2.09 g, 0.005 mol) was dissolved in 15 mL acetonitrile, then nicotinamide (0.61 g, 0.005 mol) was added. The solution was refluxed for 6 days, then the solvent was removed. To the gum-like residue, 30 mL of ethyl ether was added and the mixture was stirred for 2 hours. The white substance which formed was removed by filtration and washed with ether. Yield 78% (2.1 g); m.p. 98°–100° C. (dec.); UV and H$^1$NMR as expected. The product had the formula:

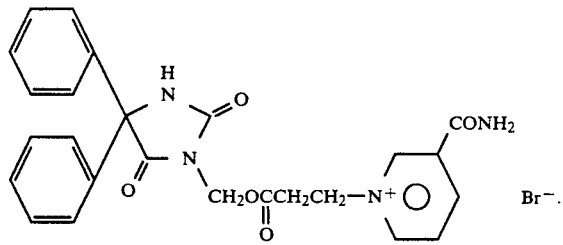

EXAMPLE 14

Preparation of 3-[2'-(3''-Carbamoyl-1''-pyridinium)propionyloxymethyl]-5,5-diphenyl-2,4-imidazolidinedione bromide The product of Example 11 (0.69 g, 0.00165 mol) was dissolved in 8 mL of acetonitrile, then nicotinamide (0.2 g, 0.00165 mol) was added and the solution was refluxed for 22 hours. The solvent was removed from the resultant brown noncrystalline substance at 50° C., then ethyl ether (15 mL) was added and the mixture was stirred for 2 hours. The light brown substance was removed by filtration and washed with ether. Yield 56% (0.5 g), m.p. 158° C. (dec.). The product had the formula:

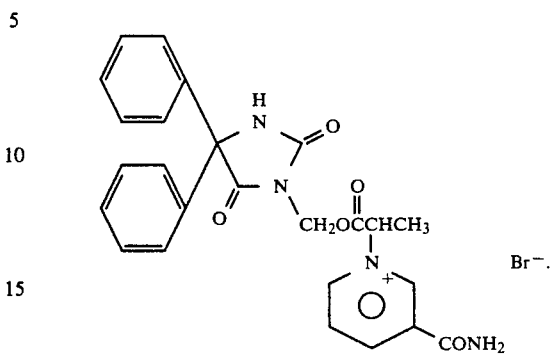

EXAMPLE 15

Preparation of 3-[(3'-Carbamoyl-1',4'-dihydropyridin-1'-yl)acetyloxymethyl]-5,5-diphenyl-2,4-imidazolidinedione The product of Example 12 (0.52 g, 0.001 mol) was dissolved in a mixture of 60 mL of water and 30 mL of ethyl acetate. The mixture was cooled at 5° C. and deaerated, then sodium bicarbonate (0.5 g, 0.006 mol) and sodium dithionite (0.7 g, 0.004 mol) were added and the resultant mixture was stirred, with deaeration and cooling, for 30 minutes. The layers were separated and the aqueous layer was extracted with 30 mL of ethyl acetate. The organic solution was extracted with 20 mL of cooled, deaerated water. After drying over sodium sulfate, the solvent was removed. Yield 55% (0.25 g) of yellow crystals, melting at 155°–160° C. (dec.). The product reduced alcoholic silver nitrate solution and had the formula:

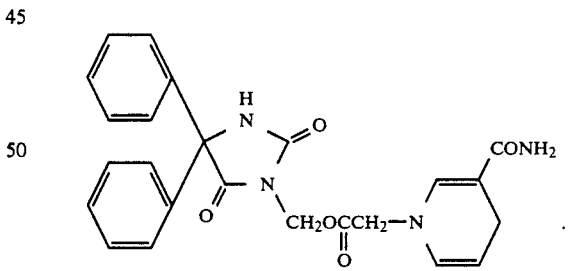

EXAMPLE 16

Preparation of 3-[3'-(3''-Carbamoyl-1'',4''-dihydropyridin-1''-yl)propionyloxymethyl]-5,5-diphenyl-2,4-imidazolidinedione Substitution of the product of Example 13 in the general procedure of Example 15 and substantial repetition of the sodium dithionite reduction there detailed afforded the desired product in 85% yield. The product melted at 100° C. (dec.) and had the formula:

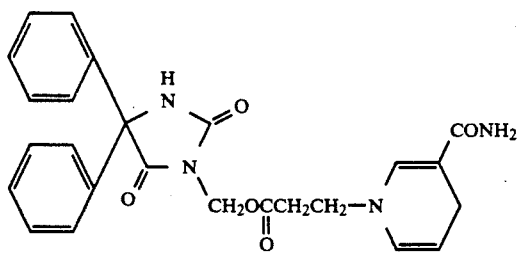

The product of Example 14 can be similarly reduced to the corresponding dihydro derivative, melting at 105° C. (dec.).

EXAMPLE 17

Preparation of 4-Aminobutanoic acid cyclohexyl ester hydrochloride

GABA (8 g, 77.6 mmol) was suspended in 100 mL (0.96 mol) of cyclohexanol. Thionyl chloride (40 mL) was added dropwise to the mixture at 0° C. The mixture was then refluxed for 4 hours, cooled and crystallized from ethyl ether. The white crystals obtained in this manner were filtered and dried. NMR analysis confirmed the identity of the product.

EXAMPLE 18

Preparation of 3-{N-[(3'-Cyclohexyloxycarbonyl)propyl]}carbamoylpyridine

Nicotinic acid (2.2 g, 18 mmol) was suspended in 50 mL of dry pyridine. Dicyclohexylcarbodiimide (3.68 g, 17.9 mmol) was dissolved in the solution, with stirring. 4-Aminobutanoic acid cyclohexyl ester hydrochloride (4 g, 18 mmol) was added and the mixture was stirred for 48 hours. Precipitated dicyclohexylurea was removed by filtration and the filtrate was evaporated to dryness. The residue was washed with 25 mL of ice cold water and extracted into ethyl acetate. The layers were separated and the organic layer was evaporated to dryness. NMR analysis confirmed the structure of the product.

EXAMPLE 19

Preparation of 1-Methyl-3-{N'-[(3'-Cyclohexyloxycarbonyl)propyl]} carbamoylpyridinium iodide The product of Example 18 (1.74 g, 6 mmol) was dissolved in a minimum amount of acetone and the resulting white precipitate was filtered. Methyl iodide (1.5 mL, 24 mmol) was added in one portion to the solution, with stirring, at 0° C. The mixture was allowed to gently reflux overnight. Filtration of a white precipitate and evaporation of the yellow filtrate produced a reddish oil, which was dissolved in acetone, filtered and evaporated to dryness. Anal. calc. for $C_{22}H_{23}O_3N_2I$: C,47.26; H,5.79; N,6.48; I,29.38. Found: C,47.03; H,5.85; N,6.44; I,29.26.

EXAMPLE 20

Preparation of 1-Methyl-3-{N-[(3'-cyclohexylcarbonyl)propyl]}carbamoyl-1,4-dihydropyridine The product of Example 19 (0.11 g, 0.26 mmol) was dissolved in 25 mL of ice cold deaerated water. NaHCO₃ (0.09 g, 4-fold excess) was added, followed by Na₂S₂O₄ (0.14 g, 3-fold excess). Ethyl acetate (25 mL) was added and the mixture was stirred under nitrogen for 30 minutes. The organic layer was extracted and dried to give an orange oil that reduced methanolic silver nitrate immediately. NMR analysis confirmed that the product had the structure:

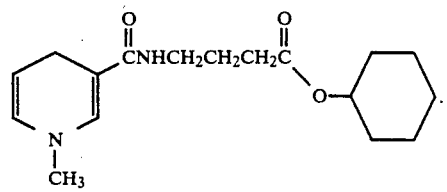

EXAMPLE 21

Preparation of Valproic acid chloride (2-Propylpentanoyl chloride)

To 4.32 g (30 mmol) of valproic acid in an ice bath, thionyl chloride (3.60 g, 30 mmol) was slowly added, with stirring. The neat mixture was allowed to come to room temperature and then heated in a water bath at 50° C. for 30 minutes. 50 mL portions of dry benzene were twice added and removed under reduced pressure. The resultant product was used in subsequent reactions without further purification.

EXAMPLE 22

Preparation of Valproic acid 2-iodoethyl ester (2'-Iodoethyl 2-propylpentanoate)

To the product of Example 21 (4.87 g, 30 mmol), 2-iodoethanol (5.16 g, 30 mmol) was added with stirring and cooling in an ice bath. The neat mixture was then heated to 100° C. in a water bath for 10 minutes, then removed from the heat and stirred for an additional 10 minutes. The reaction mixture was then dissolved in 50 mL of ether, washed with water (1×30 mL), 5% NaOH (2×30 mL), and again with water (2×30 mL). The ether layer was dried over anhydrous sodium sulfate and the solvent was removed under reduced pressure. A light yellow liquid product was obtained in 67% yield from valproic acid (6.0 g). Silver nitrate gave a bright yellow precipitate. NMR analysis confirmed the identity of the product.

EXAMPLE 23

Preparation of 1-[2'-(2''-Propyl)pentanoyloxy]ethyl-3-carbamoylpyridinium iodide The product of Example 22 (3.28 g, 11 mmol) and 50 mL of dimethylformamide were added to nicotinamide (1.22 g, 10 mmol). The mixture was heated to reflux for 3 hours, then was cooled. Removal of solvent under reduced pressure afforded a brown oily residue, which was stirred with ether (60 mL) for 30 minutes, giving a yellow powder. The ether was decanted and a fresh portion of ether (50 mL) was added. The crude product was vacuum filtered under N₂, then was recrystallized from isopropanol/ether to give 3.5 g of the desired product (84% yield), m.p. 111°–112° C. The product had the formula:

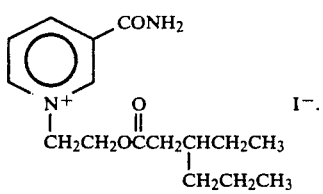

EXAMPLE 24

Preparation of 1-[2'-(2''-Propyl)pentanoyloxy]ethyl-3-carbamoyl-1,4-dihydropyridine To 50 mL of ice-cold degassed deionized water, the product of Example 23 (420 mg, 1 mmol) was added. To that solution, NaHCO$_3$ (366 mg, 4 mmol) and Na$_2$S$_2$O$_4$ (696 mg, 4 mmol) were added, with stirring. Nitrogen gas was bubbled through the solution for 30 minutes. The aqueous solution was then extracted with ether (6×25 mL) until the ether layer was no longer yellow. The combined ether extracts were washed with water (1×50 mL) and dried over MgSO$_4$. The ether layer was decanted from the drying agent and the solvent was removed under reduced pressure. To the oily residue, ether was added and then removed (10×5 mL) on a vacuum pump. A foam was formed, which returned to an oil upon exposure to the atmosphere. Structure was confirmed by NMR analysis.

EXAMPLE 25

Preparation of N-Nicotinoyltyrosine ethyl ester

Nicotinic acid (12.3 g, 0.1 mol) was dissolved in dry pyridine (300 mL). The solution was cooled and dicyclohexylcarbodiimide (20.6 g, 0.1 mol) was added. After dissolution, tyrosine ethyl ester hydrochloride (24.6 g, 0.1 mol) was added and the solution was stirred overnight. The precipitated dicyclohexylurea (DCU) was removed by filtration. Additional DCU was removed by triturating the oil with hot water. The product was purified with acetone. Calculated for C$_{17}$H$_{18}$N$_2$O$_4$.1/2-H$_2$O: C,63.16; H,5.88; N,8.66. Found: C,63.10; H,5.96; N,8.59. The product can also be named N-[1-ethoxycarbonyl-2-(4'-hydroxyphenyl)ethyl]nicotinamide.

EXAMPLE 26

Preparation of N-[(1-Methyl-3-pyridinium)carbonyl]-tyrosine ethyl ester iodide

N-Nicotinoyltyrosine ethyl ester (20 g, 0.06 mol) was dissolved in 200 mL of acetone. A two molar excess of methyl iodine (25.6 g, 0.18 mol) was added and the mixture was refluxed for 6 hours. The solvent was removed under reduced pressure to yield the desired product as a solid form. NMR analysis confirmed the identity of the product, which had the structural formula:

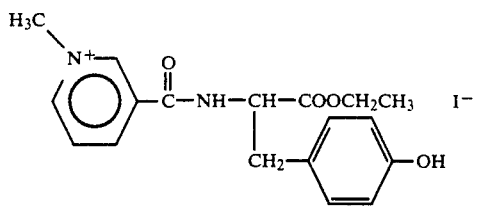

and can also be named 1-methyl-3-{N-[(1'-ethoxycarbonyl)-2'-(4''-hydroxyphenyl)ethyl]}carbamoylpyridinium iodide.

EXAMPLE 27

Preparation of 1-Methyl-3-{N-[(1'-ethoxycarbonyl)-2'-(4''-pivaloyloxyphenyl)ethyl]}carbamoylpyridinium trifluoroacetate The product of Example 26 (6 g, 0.013 mol) was dissolved in 50 mL of cold trifluoroacetic acid at 0° C. in an ice bath. Pivaloyl chloride (3.14 g, 0.026 mol) was slowly added and the solution was warmed to room temperature. After 24 hours, the solvent was removed under reduced pressure. The resulting dark oil was triturated with petroleum ether but no solidification occurred. Identity of the product was confirmed by NMR analysis. The product was dissolved in aqueous methanol (10%) and extracted with ethyl ether to remove a highly colored contaminant before using as the starting material in Example 29 below.

EXAMPLE 28

Preparation of 1-Methyl-3-{N-[(1'-ethoxycarbonyl)-2'-(4''-isobutyryloxyphenyl)ethyl]}carbamoylpyridinium trifluoroacetate The product of Example 26 (6 g, 0.013 mol) was dissolved in 50 mL of trifluoroacetic acid cooled to 0° C. in an ice bath. To that solution, with stirring, was slowly added isobutyryl chloride (2.77 g, 2.76 mL). The solution was stirred overnight at ambient temperature and the solvent was removed under reduced pressure. The oil was stirred overnight with petroleum ether and then dried in vacuo, but no solidification occurred. Identity of the product was confirmed by NMR analysis. The product was dissolved in aqueous methanol (10%) and extracted with ethyl ether to remove a highly colored contaminant before using in Example 30 below.

EXAMPLE 29

Preparation of 1-Methyl-3-{N-[(1'-ethoxycarbonyl)-2'-(4''-pivaloyloxyphenyl)ethyl]}carbamoyl-1,4-dihydropyridine The product of Example 27 (4.07 g, 0.0079 mol) was dissolved in 100 mL of 25% aqueous methanol. Nitrogen gas was bubbled through the solution. To the solution, stirring in an ice bath, was then added NaHCO$_3$ (2.02 g, 0.024 mol). Ethyl ether (100 mL) was added, followed by the addition of Na$_2$S$_2$O$_4$ (4.12 g, 0.024 mol). The yellow biphasic solution was stirred for 30 minutes, then the layers were separated and the aqueous layer was extracted twice with 75 mL portions of ethyl ether. The combined organic fractions were dried over Na$_2$SO$_4$ and the solvent was removed under reduced pressure to afford a solid foam which was oxidized by ethanolic silver nitrate. Anal. calc. for $C_{23}H_{20}N_2O_5 \cdot \frac{1}{2}H_2O$: C,65.23; H,7.33. Found: C,65.76; H,7.28; N,6.95.

EXAMPLE 30

Preparation of 1-Methyl-3-{N-[(1'-ethoxycarbonyl)-2'-(4"-isobutyryloxyphenyl)ethyl]}carbamoyl-1,4-dihydropyridine The product of Example 28 (2.20 g, 0.0044 mol) was dissolved in 100 mL of aqueous methanol. The solution was cooled in an ice bath with a stream of $N_2$ passing through it. To this solution, $NaHCO_3$ (1.11 g, 0.0132 mol) and ether (100 mL) were added. Then, sodium dithionite (2.30 g, 0.0132 mol) was added and the solution was stirred for 30 minutes. The layers were separated and the aqueous phase was washed with ethyl ether. The combined organic layers were dried over anhydrous $Na_2SO_4$ and reduced in volume. The resultant orange oil was oxidized by ethanolic silver nitrate. Identity of the product was confirmed by NMR analysis.

EXAMPLE 31

Preparation of Chloromethyl [2S-(2α,5α,6β)]-3,3-dimethyl-7-oxo-6-[(2,6-dimethoxy)benzamido]-4-thia-1-azabicyclo[3.2.0]heptane-2-carboxylate To a solution of 4.02 g (0.01 mol) methicillin sodium salt in 10 mL water and 10 mL $CH_2Cl_2$, 2.4 g sodium bicarbonate and 0.34 g tetrabutylammonium hydrogen sulfate were added. Then, 1.9 g (0.0115 mol) chloromethyl chlorosulfate dissolved in 3 mL $CH_2Cl_2$ were added with stirring, over a 5 minute period, keeping the temperature below 30° C. After an additional 30 minutes of stirring, the organic phase was separated, washed twice with water and dried over $MgSO_4$. By removing the solvent in vacuo, 4.24 g of the desired product were obtained as a yellow solid, melting at 88°-90° C.

EXAMPLE 32

Preparation of Chloromethyl [2S-(2α,5α,6β)-3,3-dimethyl-6-(5-methyl-3-phenyl-4-isoxazolecarboxamido)-7-oxo-4-thia-1-azabicyclo[3.2.0-]heptane-2-carboxylate Substantial repetition of the procedure of Example 31 using 2.12 g (0.005 mol) oxacillin sodium salt with 1.2 g $NaHCO_3$, 0.17 g tetrabutylammonium hydrogen sulfate and 0.95 g chloromethyl chlorosulfate afforded 1.87 g of the desired product melting at 78°-80° C. (dec.).

EXAMPLE 33

Preparation of Chloromethyl [2S-(2α,5α,6β)-6-[3-(2-chlorophenyl)-5-methyl-4-isoxazolecarboxamido]-3,3-dimethyl-7-oxo-4-thia-1-azabicyclo[3.2.0]heptane-2-carboxylate Using the same procedure as in Example 31, but substituting 2.38 g (0.005 mol) cloxacillin sodium salt (1 mol water), 1.2 g $NaHCO_3$, 0.17 g $Bu_4NHSO_4$ and 0.95 g chloromethyl chlorosulfate gave 2.27 g of the desired product melting at 97°-100° C. (dec.).

EXAMPLE 34

Preparation of Chloromethyl [2S-(2α,5α,6β)-6-[3-(2,6-dichlorophenyl)-5-methyl-4-isoxazolecarboxamido]-3,3-dimethyl-7-oxo-4-thia-1-azabicyclo[3.2.0]heptane-2-carboxylate Similarly, following the procedure of Example 31 but using 2.55 g (0.005 mol) dicloxacillin Na salt (1 mol water) with 1.7 g $NaHCO_3$, 0.17 g $Bu_4NHSO_4$ and 0.95 g chloromethyl chlorosulfate, 2.43 g of product were obtained melting at 98°-101° C. (dec.).

EXAMPLE 35

Preparation of [(3-Pyridinylcarbonyl)oxy]methyl[2S-(2α,5α,6β)]-3,3-dimethyl-7-oxo-6-[(2,6-dimethoxy)benzamido]-4-thia-1-azabicyclo[3.2.0]heptane-2-carboxylate Three and eight-tenth grams (0.0089 mol) of the methicillin chloromethyl ester produced in Example 31 and 1.6 g (0.01 mL) potassium nicotinate in 70 mL DMF were stirred 6 days at room temperature (20°-25° C.). 300 mL ethyl acetate were added, the resultant solid was removed by filtration and the solution was extracted 4 times with 50 mL concentrated aqueous NaCl and dried over $MgSO_4$. The solvent was removed in vacuo and the resultant residue was purified by chromatography (silica gel). Obtained as a white solid were 3 g of the desired product melting at 151°-157° C.

EXAMPLE 36

Preparation of [(3-Pyridinylcarbonyl)oxy]methyl[2S-(2α,5α,6β)]-3,3-dimethyl-6-(5-methyl-3-phenyl-4-isoxazolecarboxamido)-7-oxo-4-thia-1-azabicyclo[3.2.0]-heptane-2-carboxylate Following the procedure of Example 35, but utilizing 1.81 g (0.004 mol) of the oxacillin chloromethyl ester produced in Example 32 and 0.75 g (0.0046 mol) K nicotinate, afforded, after purification by chromatography, 0.75 g of the desired product as a white solid melting at 79°-82° C. (dec.).

EXAMPLE 37

Preparation of [(3-Pyridinylcarbonyl)oxy]methyl[2S(2α,5α,6β)]-6-[3-(2-chlorophenyl)-5-methyl-4-isoxazolecarboxamido]-3,3dimethyl-7-oxo-4-thia-1-azabicyclo-[3.2.0]heptane-2-carboxylate Using the procedure of Example 35, but substituting 2.1 g (0.0043 mol) of the cloxacillin chloromethyl ester produced in Example 33 and 0.8 g (0.005 mol) K nicotinate, gave 1.2 g of product melting at 83°-85° C. (dec.).

EXAMPLE 38

Preparation of [(3-Pyridinylcarbonyl)oxy]methyl [2S(2α,5α,6β)]-6-[3-(2,6-dichlorophenyl)-5-methyl-4-isoxazolecarboxamido]-3,3-dimethyl-7-oxo-4-thia-1-azabicyclo[3.2.0]heptane-2-carboxylate Similarly, following the procedure of Example 35 but using 2.27 g (0.0047 mol) of the dicloxacillin chloromethyl ester produced in Example 34 and 0.87 g (0.0054 mol) K nicotinate afforded 1.1 g of the product as a white solid melting at 87°-90° C. (dec.).

EXAMPLE 39

Preparation of [2S-(2α,5α,6β)]-3-[[[[[3,3-Dimethyl-7-oxo-6-[(2,6-dimethoxy)benzamido]-4-thia-1-azabicyclo[3.2.0]hept-2-yl]carbonyl]oxy]methoxy]carbonyl]-1-methylpyridinium iodide One and one-fourth grams (0.0024 mol) of the methicillin derivative produced in Example 35 in 35 mL nitromethane and 1.14 g (0.5 mL) (0.008 mol) methyl iodide were reacted in a closed system at room temperature (20°-25° C.) for 7 days. The solvent was removed in vacuo, the resultant residue was stirred with ether, filtered off, washed with ether and dried. There were thus obtained 1.6 g of yellow hygroscopic product melting at 95°-100° C. and being further characterized by the structural formula:

in Example 36 in 25 mL nitromethane and 0.45 g (0.2 mL) (0.003 mol) CH₃I produced, after 6 days, 0.6 g of the desired product melting at 75°-80° C. and having the formula:

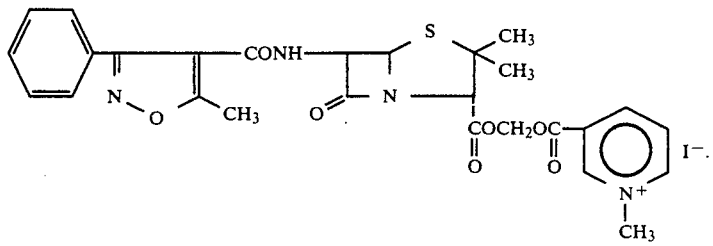

EXAMPLE 41

Preparation of [2S-(2α,5α,6β)]-3-[[[[[6-[3-(2-chlorophenyl)-5-methyl-4-isoxazolecarboxamido]-3,3-dimethyl-7-oxo-4-thia-1-azabicyclo[3.2.0]hept-2-yl]carbonyl]oxy]methoxy]carbonyl]-1-methylpyridinium iodide Similarly, using the procedure of Example 39, but substituting 0.44 g (0.0008 mol) of the cloxacillin derivative produced in Example 37 in 25 mL nitromethane and 0.45 g (0.2 mL) (0.003 mol) CH₃I, gave 0.45 g of product melting at 90°-95° C. (dec.) and having the formula:

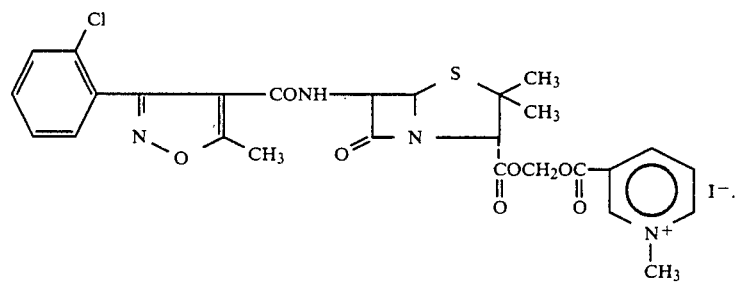

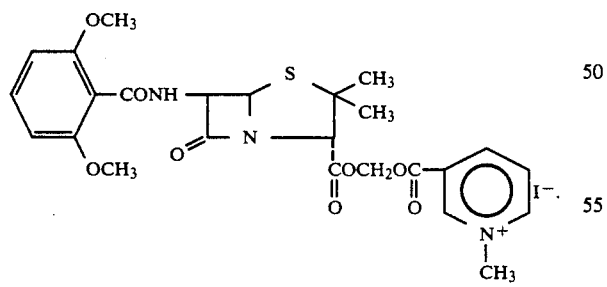

EXAMPLE 40

Preparation of [2S-(2α,5α,6β)]-3-[[[[[3,3-dimethyl-6-(5-methyl-3-phenyl-4-isoxazolecarboxamido)-7-oxo-4-thia-1-azabicyclo[3.2.0]hept-2-yl]carbonyl]oxy]methoxy]carbonyl]-1-methylpyridinium iodide Using the procedure of Example 39, but substituting 0.5 g (0.0009 mol) of the oxacillin derivative produced

EXAMPLE 42

Preparation of [2S-(2α,5α,6β)-3-[[[[[6-[3-(2,6-dichlorophenyl)-5-methyl-4-isoxazolecarboxamido]-3,3-dimethyl-7-oxo-4-thia-1-azabicyclo[3.2.0]hept-2-yl]carbonyl]oxy]methoxy]carbonyl]-1-methylpyridinium iodide In a similar manner, using the procedure of Example 39, but substituting 0.5 g (0.007 mol) of the dicloxacillin derivative produced in Example 38 in 25 mL nitromethane and 0.45 g (0.2 mL) (0.003 mol) CH₃I gave 0.55 g of product melting at 95°-100° C. (dec.) and having the formula:

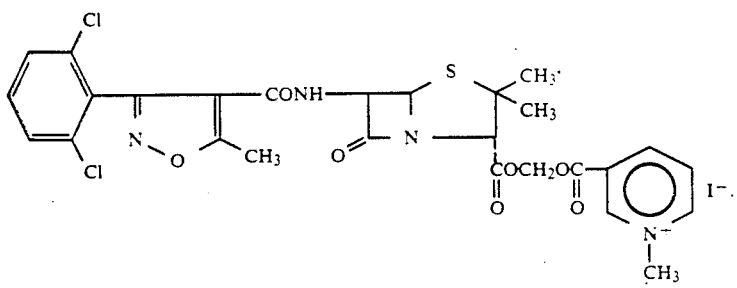

EXAMPLE 43

Preparation of
[[(1,4-Dihydro-1-methyl-3-pyridinyl)carbonyl]oxy]methyl[2S-(2α,5α,6β)]-3,3-dimethyl-7-oxo-6-[(2,6-dimethoxy)benzamido]-4-thia-1-azabicyclo[3.2.0]heptane-2-carboxylate 0.45 g (0.0007 mol) of the product of Example 39 dissolved in a mixture of deaerated 25 mL ethyl acetate and 70 mL water was reduced with a mixture of 0.34 g (0.004 mol) $NaHCO_3$ and 0.48 g (0.0028 mol) sodium dithionite at 0°–5° C. over 70 minutes. The disappearance of the 268 nm maxima and increase of 366 nm maxima in the U.V. spectra were followed. The layers were separated and the aqueous layer was extracted with 2×25 mL ethyl acetate, then the organic layers were extracted with 2×20 mL cold, deaerated water. After drying over $Na_2SO_4$, the solvent was removed in vacuo. 0.25 g of the product was obtained as a yellow solid melting at 88°–90° C. (dec.). The product had the formula:

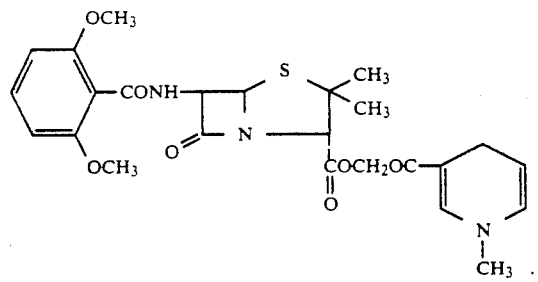

EXAMPLE 44

Preparation of
[[(1,4-Dihydro-1-methyl-3-pyridinyl)carbonyl]oxy]methyl[2S-(2α,5α,6β)]-3,3-dimethyl-6-(5-methyl-3-phenyl-4-isoxazolecarboxamido)-7-oxo-4-thia-1-azabicyclo[3.2.0]heptane-2-carboxylate Similarly, repetition of the general procedure of Example 43 using 0.17 g (0.00025 mol) of the product of Example 40, 0.08 g (0.0001 mol) $NaHCO_3$ and 0.51 g (0.001 mol) $Na_2S_2O_4$, in 15 mL water and 15 mL ethyl acetate, afforded 0.1 g of product melting at 93°–100° C. (dec.). The product had the formula:

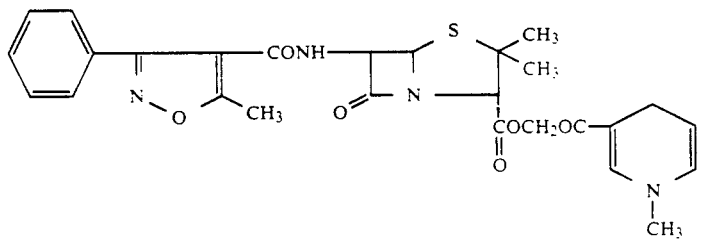

EXAMPLE 45

Preparation of
[[(1,4-Dihydro-1-methyl-3-pyridinyl)carbonyl]oxy]methyl[2S-(2α,5α,6β)]-6-[3-(2-chlorophenyl)-5-methyl-4-isoxazolecarboxamido]-3,3-dimethyl-7-oxo-4-thia-1-azabicyclo[3.2.0]heptane-2-carboxylate In a similar manner, following the procedure of Example 43, but substituting 0.18 g (0.00025 mol) of the product of Example 41, 0.089 $NaHCO_3$ and 0.17 g $Na_2S_2O_4$, gave 0.13 g of product as a yellow solid, melting at 80°–85° C. (dec.) and having the structural formula:

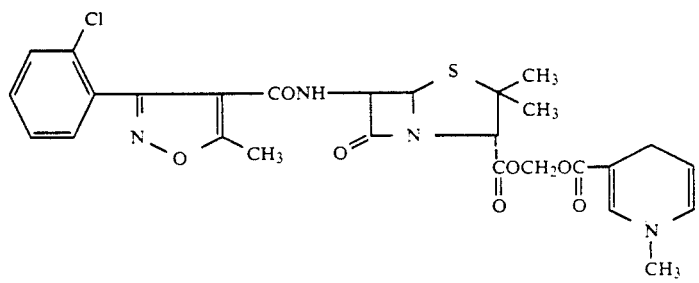

EXAMPLE 46

Preparation of
[[(1,4-Dihydro-1-methyl-3-pyridinyl)carbonyl]oxy]methyl[2S-(2α,5α,6β)]-6-[3-(2,6-dichlorophenyl)-5-methyl-4-isoxazolecarboxamido]-3,3-dimethyl-7-oxo-4-thia-1-azabicyclo[3.2.0]heptane-2-carboxylate In like manner, repetition of the procedure of Example 43 using 0.19 g (0.00025 mol) of the product of Example 42, 0.08 g NaHCO₃, 0.17 g Na₂S₂O₄ yielded 0.14 g of desired product melting at 98°-102° C. (dec.) and having the formula:

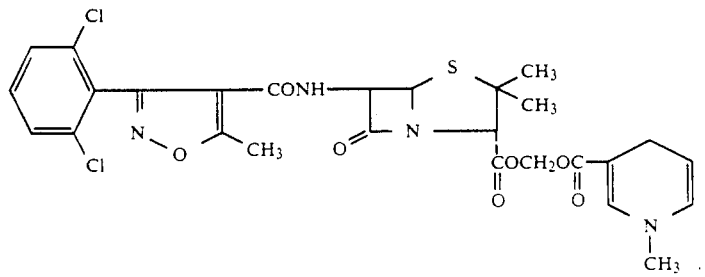

EXAMPLE 47

Preparation of
[(3-Pyridinylcarbonyl)oxy]methyl[2S(2α,5α,6β)]-3,3-dimethyl-7-oxo-6-[(phenylacetyl)amino]-4thia-1-azabicyclo[3.2.0]heptane-2-carboxylate A suspension of 3.83 g (0.01 mol) of the chloromethyl ester of benzylpenicillin, namely chloromethyl [2S-(2α,5α,6β)]-3,3-dimethyl-7-oxo-6-[(phenylacetyl)amino]-4-thia-1-azabicyclo[3.2.0]heptane-2-carboxylate, and 1.93 g (0.012 mol) potassium pyridine-3-carboxylate in 100 mL of dimethylformamide was stirred at 20°-25° C. for 6 days. Then, 300 mL of ethyl acetate were added and the solid was removed by filtration. The solution was extracted 4 times with concentrated aqueous sodium chloride solution, then dried over MgSO₄. The solvent was removed in vacuo to give 4.5 g of foamy solid. Purification by chromatography over silica gel using ethyl acetate as eluent afforded 2.5 g of product melting at 127°-130° C.

EXAMPLE 48

Preparation of
[2S-(2α,5α,6β)]-3-[[[[[3,3-Dimethyl-7-oxo-6-[(phenylacetyl)amino]-4-thia-1-azabicyclo[3.2.0]hept-2-yl]carbonyl]oxy]methoxy]carbonyl]-1-methyl-pyridinium iodide Two and one-half grams (0.053 mol) of the product of Example 47 dissolved in 100 mL of dry nitromethane were reacted with 2.25 g (1 mL, 0.016 mol) of methyl iodide in a closed system at 20°-25° C. for 6 days, at the end of which time thin layer chromatography showed complete reaction. The solvent was removed in vacuo and the solid residue was slurried with ether, filtered and dried in vacuo over P₂O₅. The product, melting at 90°-95° C. (dec.), was obtained as a yellow solid (2.91 g). It was assigned the structural formula:

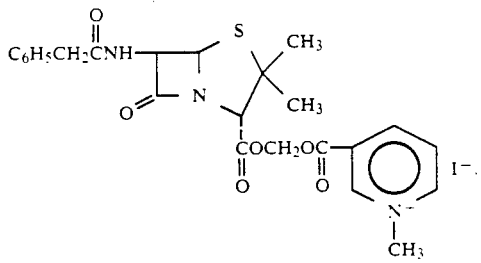

EXAMPLE 49

Preparation of
[[(1,4-Dihydro-1-methyl-3-pyridinyl)carbonyl]oxy]methyl[2S-(2α,5α,6β)]-3,3-dimethyl-7-oxo-6-[(phenylacetyl)amino]-4-thia-1-azabicyclo[3.2.0]heptane-2-carboxylate The quaternary salt prepared in Example 48 (3.25 g, 0.0053 mol) was dissolved in a mixture of 350 mL of water and 150 mL of ethyl acetate. The resultant mixture was cooled at 0°-5° C. and deaerated with nitrogen, then a mixture of 2.67 g (0.032 mol) of sodium bicarbonate and 3.69 g (0.021 mol) of sodium dithionite was added over a 2-3 minute period. The reaction mixture was stirred for 1 hour under the same conditions as before, then the layers were separated, the aqueous layer was extracted twice with 50 mL portions of ethyl acetate, and the combined organic extracts were washed twice with 30 mL portions of cold, deaerated water. Drying over sodium sulfate and removal of the solvent in vacuo afforded 1.7 g of yellow solid melting 98°-100° C. and having the formula:

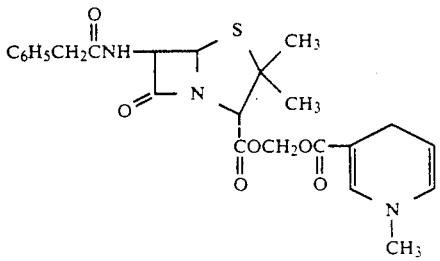

EXAMPLE 50

Preparation of Chloromethyl N-[3-(10,11-dihydro)-5H-dibenz[b,f]azepin-5-yl)]propyl-N-methylcarbamate Method A:

Desipramine hydrochloride (1.5 g, 0.005 mol) was dissolved in 20 mL of methylene chloride, cooled at 0°-5° C. Then 1 g NaHCO₃ was added, followed by 0.92 g (0.007 mol) chloromethyl chloroformate. The reaction mixture was stirred for 1 hour, then the salts were removed by filtration and the solution was extracted twice with 10 mL portions of 5% HCl. The organic layer was dried over MgSO₄ and the solvent was removed in vacuo to give the desired compound as a colorless oily substance in 76% yield (1.35 g).

Method B:

Imipramine hydrochloride (1.59 g, 0.005 mol) was dissolved in 15 mL of water, then 5 mL of 4% sodium hydroxide solution was added, with cooling. The resultant imipramine base was extracted twice with 10 mL portions of benzene. The solution was concentrated to 10 mL, then a solution of 0.7 g (0.0054 mol) chloromethyl chloroformate in 5 mL benzene was added with cooling at 10° C. The reaction mixture was stirred at 20°-25° C. for 30 minutes, then was refluxed for 1 hour. A small amount of imipramine hydrochloride resulted and was filtered off. The solution was extracted twice with 20 mL portions of 4% HCl and dried over MgSO₄. Removal of solvent in vacuo afforded 1.2 g (66%) of product having the same characteristics as that obtained by Method A.

EXAMPLE 51

Preparation of 1-Chloroethyl N-[3-(10,11-dihydro-5H-dibenz[b,f]azepin-5-yl)]propyl-N-methylcarbamate Following the general procedure of Example 50, but using 1.5 g (0.005 mol) of desipramine hydrochloride and 0.86 g (0.006 mol) chloroethyl chloroformate and carrying out the reaction at 5°-10° C. for 2 hours, gave 1.6 g (86%) of the title compound as a colorless oil.

EXAMPLE 52

Preparation of [{N-[3-(10,11-Dihydro-5H-dibenz[b,f]azepin-5-yl)]propyl-N-methylamino}carbonyloxy]methyl 3-pyridinecarboxylate The product of Example 50 (1.35 g, 0.0037 mol) dissolved in 5 mL dimethylformamide was added to a solution prepared from 0.57 g (0.046 mol) nicotinic acid and 0.45 g triethylamine in 5 mL dimethylformamide. The mixture was stirred for 24 hours at 25°-30° C., then 30 mL of ethyl acetate were added. The precipitated salts were removed by filtration and the solution was extracted 4 times with 15 mL portions of saturated aqueous sodium chloride solution. Drying over MgSO₄ and removal of the solvent in vacuo afforded 1 g (61%) of pure product as an oil.

EXAMPLE 53

Preparation of [1-{N-[3-(10,11-Dihydro-5H-dibenz[b,f]azepin-5-yl)]propyl-N-methylamino}carbonyloxy]ethyl 3-pyridinecarboxylate Following the general procedure of Example 52, but using 1.05 g (0.0028 mol) of the product of Example 51, 0.45 g (0.036 mol) of nicotinic acid and 0.36 g of triethylamine in 10 mL dimethylformamide and carrying out the reaction at 25°-30° C. for 48 hours, gave 0.5 g of the title compound as a yellow oil.

EXAMPLE 54

Preparation of 3-[{N-[3-(10,11-Dihydro-5H-dibenz[b,f]azepin-5-yl)]propyl-N-methylamino}carbonyloxy]methoxycarbonyl-1-methylpyridinium iodide Eight-tenths gram (0.0018 mol) of the product of Example 52 in 30 mL of nitromethane was methylated with 0.8 mL of methyl iodide at 25°-30° C. for 48 hours. The solvent was removed in vacuo and the residue was slurried with ethyl ether, filtered and dried over P₂O₅. The quaternary salt was obtained in 83% yield (0.88 g) as a light yellow solid melting at 172°-175° C. (dec.) and having the structural formula:

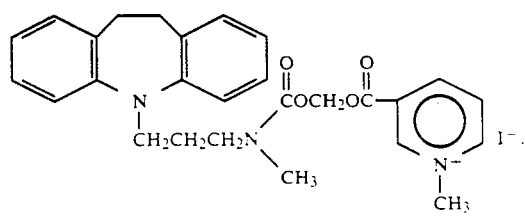

EXAMPLE 55

Preparation of 3-[1-{N-[3-(10,11-Dihydro-5H-dibenz[b,f]azepin-5-yl)]propyl-N-methylamino}carbonyloxy]ethoxycarbonyl-1-methylpyridinium iodide Following the general alkylation procedure of Example 54, but using 0.5 g (0.0011 mol) of the product of Example 53 in 15 mL nitromethane with 0.5 mL methyl iodide, and carrying out the reaction at 20°-25° C. for 6 days, afforded 0.33 g (50%) of the desired quaternary salt as a dark yellow solid melting at 101°-103° C. (dec.) and having the structural formula:

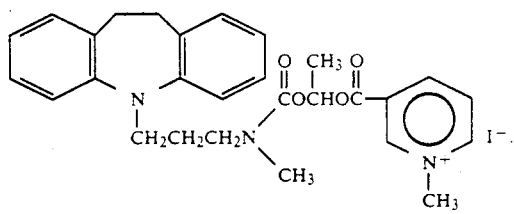

EXAMPLE 56

Preparation of [{N-[3-(10,11-Dihydro-5H-dibenz[b,f]azepin-5-yl)]propyl-N-methylamino}carbonyloxy]methyl 1,4-dihydro-1-methyl-3-pyridinecarboxylate Three-tenths gram (0.0005 mol) of the product of Example 54 in 30 mL water and 15 mL ethyl acetate was reduced with 0.25 g (0.003 mol) NaHCO₃ and 0.35 g (0.002 mol) sodium dithionite at 0°-5° C., with deaeration, for a 60 minute period. The layers were separated and the aqueous layer was extracted twice with 30 mL portions of ethyl acetate. The combined organic layers were then extracted twice with 20 mL portions of cool deaerated water. Drying over Na₂SO₄ and removal of the solvent in vacuo afforded 0.22 g (95%) of the title compound, melting at 59°-63° C. (dec.) and having the structural formula:

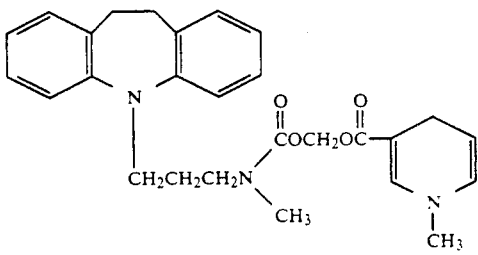

EXAMPLE 57

Preparation of
[1-{N-[3-(10,11-Dihydro-5H-dibenz[b,f]azepin-5-yl)]propyl-N-methylamino}carbonyloxy]ethyl 1,4-dihydro-1-methyl-3-pyridinecarboxylate Following the procedure of Example 56, but using 0.1 g (0.0017 mol) of the product of Example 55 in 10 mL water and 6 mL ethyl acetate, 0.11 g NaHCO$_3$ and 0.15 g Na$_2$S$_2$O$_4$ and carring out the reaction for a 60 minute period, gave 0.07 g (88%) of the title compound as a yellow solid, melting at 60°–65° C. (dec.) and having the structural formula:

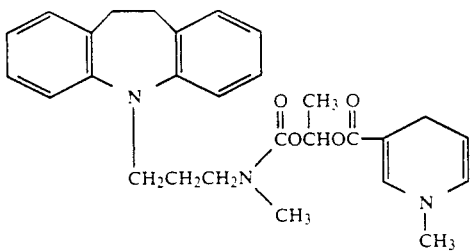

EXAMPLE 58

Preparation of
N-(2-Hydroxyethyl)-3-pyridinecarboxamide

A solution of 49.2 g (0.32525 mol) ethyl nicotinate and 72 g (1.17 mol) ethanolamine was heated at 70° C. for 60 hours. The excess ethanolamine was removed under reduced pressure and the resulting viscous cream oil was stirred with ether for 48 hours. The resulting white solid was removed by filtration, affording 46 g (85.1%) of the title compound melting at 75°–78° C.

EXAMPLE 59

Preparation of
3-[2'-(2"-propyl)pentanoyloxy]ethylcarbamoylpyridine

To a stirred solution of 1.0 g (0.006021 mol) of the product of Example 58 and 0.61 g (0.00598 mol) triethylamine in 40 mL dry dichloromethane, 1.96 g (0.012047 mol) of (2-propyl)pentanoyl chloride were added and the mixture was refluxed for 4 hours. The resultant solution was washed sequentially with 30 mL 5% NaHCO$_3$, 30 mL 5% HCl and 30 mL water. The organic layer was dried over MgSO$_4$ and the solvent was removed under reduced pressure to give 0.6 g (34.3%) of the product as a pale brown oil.

EXAMPLE 60

Preparation of
1-Methyl-3-[2'-(2"-propyl)pentanoyloxy]ethylcarbamoylpyridinium iodide To a solution of 1 g (0.00342 mol) of the product of Example 59 in 20 mL of dry ethyl acetate, 0.73 g (0.00513 mol) of methyl iodide was added. The reaction mixture was stirred overnight at room temperature. The pale yellow solid which formed was removed by filtration and recrystallized from ethyl acetate to give 1.35 g (90.9%) of the quaternary salt as a yellow crystalline solid. The product had the formula:

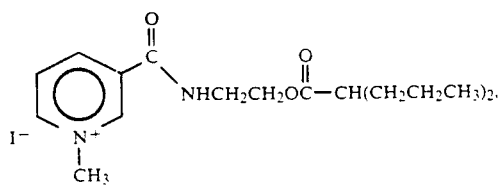

as confirmed by IR, NMR and UV analyses.

EXAMPLE 61

Preparation of
1-Methyl-3-[2'-(2"-propyl)pentanoyloxy]ethylcarbamoyl-1,4-dihydropyridine To 50 mL of vigorously stirred, degassed, ice-cold deionized water, a solution of 3.0 g (0.006909 mol) of the quaternary product of Example 60 in 50 mL of ethyl acetate was added. Throughout the reaction, the temperature and pH were maintained at 0° C. and 8 respectively, while nitrogen was bubbled through the reaction mixture. A mixture of 3.5 g (0.04145 mol) of sodium bicarbonate and 4.8 g (0.02763 mol) of sodium dithionite was added portionwise. After 45 minutes, the organic layer was separated and the aqueous layer was extracted with 100 mL of ice-cold ethyl acetate. The combined organic extracts were washed with ice-cold water and dried over MgSO$_4$. Solvent was removed under reduced pressure to give 2.1 g (98.8%) of the product as a pale yellow solid having the structural formula:

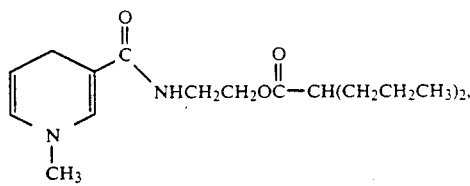

as confirmed by IR, NMR and UV analyses.

EXAMPLE 62

Preparation of 3-Pyridinecarboxylic acid (2-hydroxy)ethyl ester hydrochloride

To 120 mL cold (−10° C.) ethylene glycol, 16 mL of thionyl chloride were added dropwise. Upon completion of the addition, 24.6 g (0.2 mol) of nicotinic acid were added portionwise and the reaction mixture was heated overnight at 60° C. Then, 700 mL of hot tetrahydrofuran were added and the mixture was cooled. The solid which formed was removed by filtration and washed with ether to give 28.5 g of the title compound as white crystals.

EXAMPLE 63

Preparation of
3-[2'-(2''-Propyl)pentanoyloxy]ethoxycarbonylpyridine

To a solution of 10.0 g (0.0491 mol) of the product of Example 62 in 150 mL of dry $CH_2Cl_2$, 10.7 g (0.09819 mol) of triethylamine were added. After all of the solid was dissolved, 11.92 g (0.07364 mol) of 2-propylpentanoyl chloride were added and the reaction mixture was stirred at room temperature for 36 hours. Sequential washing with 5% $NaHCO_3$, 5% HCl and water afforded an organic layer which was then dried over anhydrous $MgSO_4$. Solvent was removed under reduced pressure to give a yellow-brown oil that was triturated with a 40:60 mixture of ether and petroleum ether to yield 9.7 g of the product as an orange oil.

EXAMPLE 64

Preparation of
1-Methyl-3-[2'-(2''-Propyl)pentanoyloxy]ethoxycarbonylpyridinium iodide To a solution of 2.0 g (0.006816 mol) of the product of Example 63 in 10 mL of dry acetone, 1.45 g (0.01022 mol) of methyl iodide were added and the mixture was refluxed overnight. Removal of solvent under reduced pressure afforded 1.84 g of the quaternary salt as a brown oil. The product had the structural formula:

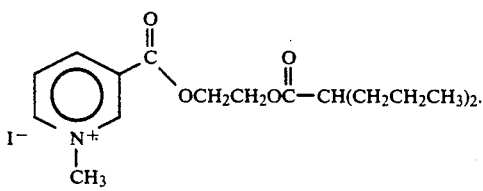

EXAMPLE 65

Preparation of
1-Methyl-3-[2'-(2''-propyl)pentanoyloxy]ethoxycarbonyl-1,4-dihydropyridine To 50 mL of vigorously stirred, degassed, ice-cold deionized water, a solution of 1.84 g (0.004226 mol) of the quaternary product of Example 64 in 50 mL of ethyl acetate was added. Throughout the reaction, the temperature and pH were maintained at 0° C. and 8, respectively, while argon was bubbled through the reaction mixture. A mixture of 2.13 g (0.02536 mol) of $NaHCO_3$ and 2.94 g (0.0169 mol) of $Na_2S_2O_4$ was added portionwise. After 55 minutes, the organic layer was separated and the aqueous layer was extracted with 100 mL of ice-cold ethyl acetate. The combined organic layers were washed with ice-cold water and dried over $MgSO_4$. The solvent was removed under reduced pressure to give 0.9 g of the title compound as a yellow oil. The product had the formula:

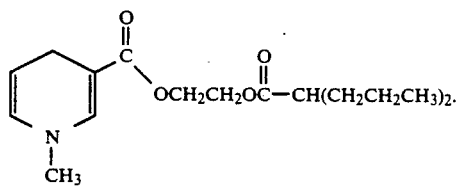

EXAMPLE 66

Preparation of
3,17β-Bis[(3-pyridinylcarbonyl)oxy]-19-nor-17α-pregna-1,3,5(10)-trien-20-yne To 2.0 g (6.7 mmol) of ethinyl estradiol dissolved in 50 mL of dry pyridine were added 6.16 g (0.027 mol) of nicotinic anhydride and a catalytic quantity of 4-(dimethylamino)pyridine (DMAP). The solution was warmed gently to 50° C. to effect solution. After 2 weeks, the pyridine solution was poured over ice and the solid produced was collected by filtration. The solid was dried over $P_2O_5$ in vacuo to give 3 g (85%) of an off-white powder.

EXAMPLE 67

Preparation of
3-Hydroxy-17β-[(3-pyridinylcarbonyl)oxy]-19-nor-17α-pregna-1,3,5(10)-trien-20-yne To 200 mL of 0.5% methanolic $KHCO_3$, 2.0 g (3.9 mmol) of the product of Example 66 were added. After 6 hours, the slurry was diluted with 200 mL of water and the mixture was extracted with chloroform. The organic layers were combined, dried over $MgSO_4$ and concentrated in vacuo. The resulting oil was triturated with hexane to give 1.48 g (94%) of a white solid. NMR and UV spectra and elemental analysis confirmed the identity of the title compound.

EXAMPLE 68

Preparation of
1-Methyl-3-{[(19-nor-17α-pregna-1,3,5(10)-trien-20-yn-17β-yl)oxy]carbonyl}pyridinium iodide To 50 mL of acetone, 1.0 g (2.5 mmol) of the product of Example 67 was added, followed by 2 mL of methyl iodide. The reaction mixture was refluxed for 12 hours. The solid which formed was collected by filtration, yielding 1.15 g (85%) of the quaternary salt as a yellow solid having the structural formula

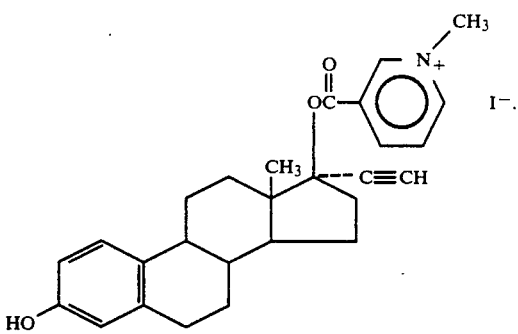

The assigned structure was confirmed by UV and NMR spectral analyses and by elemental analysis.

EXAMPLE 69

Preparation of
3-Hydroxy-17β-{[(1-methyl-1,4-dihydropyridin-3-yl)carbonyl]oxy}-19-nor-17α-pregna-1,3,5(10)-trien-20-yne To a cooled suspension of 1.0 g (1.8 mmol) of the product of Example 68 in 100 mL of 50:50 water: tert-butanol, 0.77 g of $NaHCO_3$ and 0.96 g of $Na_2S_2O_4$ were added. The reaction mixture was stirred at 0° C. for 1 hour, then was extracted twice with 100 mL portions of CH2Cl2. The organic extracts were combined, dried over MgSO4 and concentrated under reduced pressure to give 520 mg (69%) of the title compound as a yellow foam. The product was assigned the structure

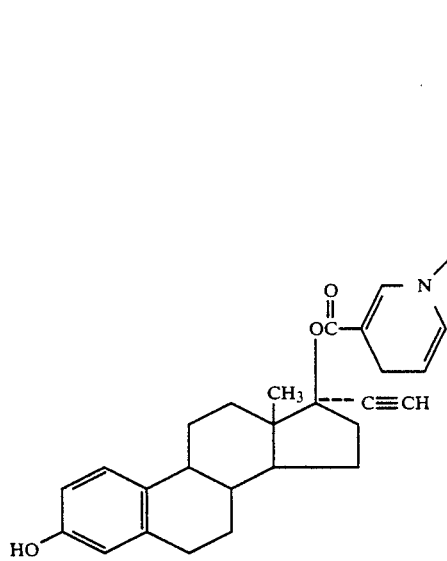

which was in accord with UV and NMR values as well as elemental analysis.

EXAMPLE 70

Preparation of 3,17β-Bis[(3-pyridinylcarbonyl)oxy]estra-1,3,5(10)-triene

To 5.3 g (0.03 mol) of nicotinoyl chloride in 30 mL of dry pyridine at 0° C. were added 2.0 g (0.0073 mol) of β-estradiol. The reaction mixture was refluxed for 1 hour, then was poured over 100 mL of ice water, and the resulting precipitate was collected by filtration. The precipitate was dried in vacuo over P2O5, affording 3.18 g (90%) of the title compound melting at 148°–150° C.

EXAMPLE 71

Preparation of 1,1'-Dimethyl-3,3'-{[(estra-1,3,5(10)triene-3,17β-diyl)-dioxy]dicarbonyl}dipyridinium diiodide To 50 mL of acetone and 2 mL (0.032 mol) of methyl iodide, 2.0 g (0.004 mol) of the product of Example 70 were added. The solution was heated at reflux overnight. The precipitate which formed was filtered, washed with acetone and dried to give 2.75 g (88%) of the quaternary salt melting at 251°–252° C. and having the structural formula

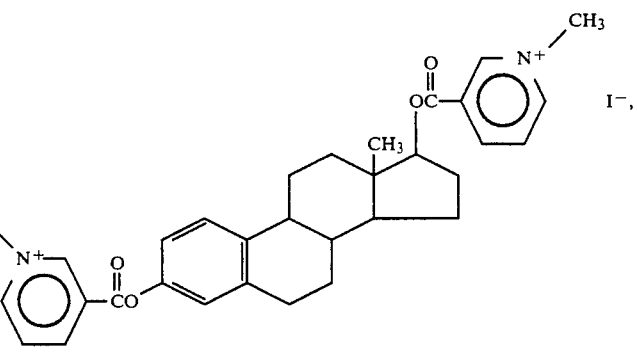

as confirmed by UV, NMR and elemental analyses.

EXAMPLE 72

Preparation of 3,17β-Bis{[(1-methyl-1,4-dihydropyridin-3-yl)carbonyl]oxy}estra-1,3,5(10)-triene One gram (1.31 mmol) of the product of Example 71 was dissolved in 100 mL of dry acetonitrile. To that solution, which was flushed with nitrogen, 0.28 g (1.31 mmol) of 1-(phenylmethyl)-4-(aminocarbonyl)-1,2-dihydropyridine was added, and the reaction mixture was stirred at 0° C. for 1 hour. Removal of the solvent under reduced pressure afforded a solid, which was suspended in methylene chloride and removed by filtration. The filtrate was chromatographed several times on a neutral alumina column prepared with methylene chloride. Purification and evaporation of the solvent in vacuo gave a solid foam. The product had the formula

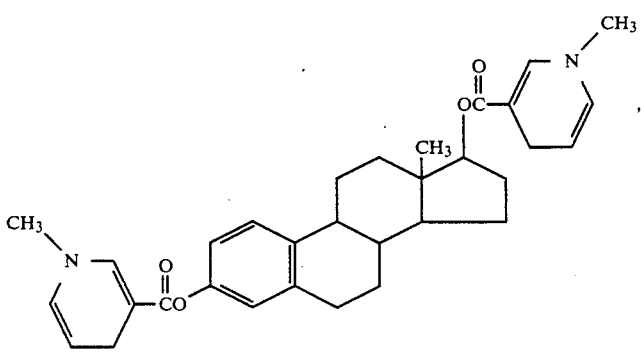

as confirmed by UV, NMR and elemental analyses.

EXAMPLE 73

Preparation of
3-(Phenylcarbonyloxy)-17β-[(3-pyridinylcarbonyl)oxy]estra-1,3,5(10)-triene Estradiol benzoate (2.5 g, 6.6 mmol) was dissolved in 50 mL of dry pyridine, then 1.66 g of nicotinic anhydride and a catalytic amount of 4-(dimethylamino)pyridine (DMAP) were added. The reaction mixture was stirred for 5 days at room temperature, then was poured into ice water. The solid which formed was collected by filtration and dried in vacuo, yielding 3.01 g (94%) of the product as a white solid melting at 151°–154° C.

EXAMPLE 74

Preparation of
1-Methyl-3-({[3-(phenylcarbonyloxy)estra-1,3,5(10)-trien-17β-yl]oxy}carbonyl)pyridinium iodide The product of Example 73 (1.5 g, 3.1 mmol) was suspended in 2.5 mL of acetone. Then, 2 mL of methyl iodide were added and the reaction mixture was refluxed overnight. The yellow solid (1.8 g, 93%) was collected by filtration and dried in vacuo. UV, NMR and elemental analyses confirmed that the product had the assigned structure:

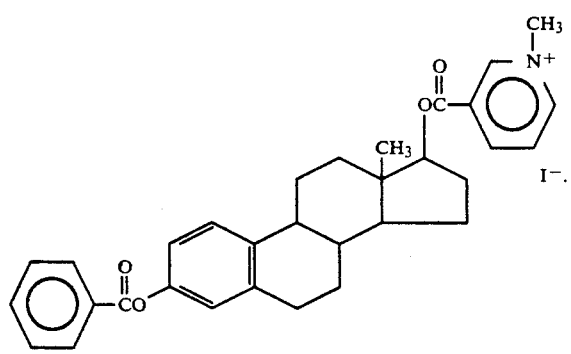

EXAMPLE 75

Preparation of
3-(Phenylcarbonyloxy)-17β-{[1-methyl-1,4-dihydropyridin-3-yl)carbonyl]oxy}estra-1,3,5(10)triene The quaternary salt prepared in Example 74 (1.2 g, 1.93 mmol) was suspended in 100 mL of 50:50 tert-butyl alcohol/water. Then, 0.81 g of NaHCO3 and 1.0 g of Na2S2O4 were added and the reaction was allowed to continue for 1.5 hours. The resultant solution was extracted with CH2Cl2, and the organic phase was dried over MgSO4 and concentrated in vacuo to afford 650 mg of title compound as a yellow foam. The identity of the product was confirmed by UV, NMR and elemental analyses. It was assigned the structure:

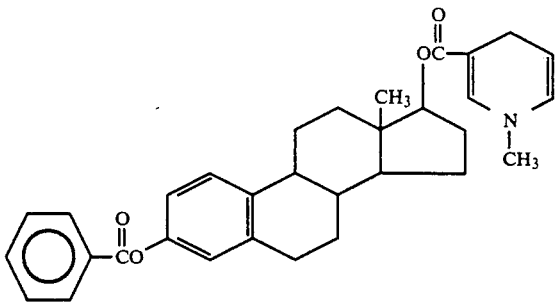

EXAMPLE 76

Preparation of
N-(2-{4-[Bis(2-chloroethyl)amino]butanoyloxy}ethyl)-3-pyridinecarboxamide Chlorambucil (20 g, 0.0657 mol) was dissolved in 800 mL of dry acetonitrile, then 13.1 g (0.079 mol) of N-(2-hydroxyethyl)-3-pyridinecarboxamide were added. Acetonitrile was added until the solution was clear. The total volume of acetonitrile used at this stage was 850 mL. To the stirred solution, maintained over argon, there were added 1.492 g (0.0723 mol) of dicyclohexylcarbodiimide and 0.802 g (0.0066 mol) of 4-(dimethylamino)pyridine (DMAP). The reaction mixture was stirred overnight at room temperature under dry conditions, and the progress of the reaction was followed by thin layer chromatography. At the end of the reaction period, the solid which formed was removed and washed with 50 mL of cold acetonitrile. The filtrate was evaporated in vacuo at 30° C., and the yellow solid thus obtained was dissolved in a minimum amount (15 mL) of 8:2 chloroform/tetrahydrofuran and applied to a column packed with 900 g of silica gel. The column was eluted with 8:2 chloroform/tetrahydrofuran. The adduct and chlorambucil were eluted within the first 500 mL, and the desired ester was then collected upon evaporation of the eluent under vacuum. The title compound was obtained in 82.7% yield as a yellow solid melting at 73°–75° C. It had the formula

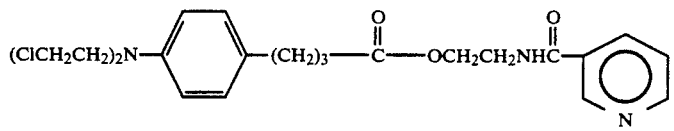

EXAMPLE 77

Preparation of
1-Methyl-3-[(N-{2-[4-({4-bis(2-chloroethyl)amino]}phenyl)butanoyloxy]ethyl})carbamoyl]pyridinium methanosulfate The product of Example 76 (2 g, 0.04 mol) was dissolved in 200 mL dry acetonitrile. Dimethyl sulfate (0.613 g, 0.0486 mol) was added and the mixture was refluxed overnight. The reaction was followed by thin layer chromatography (8:2 chloroform/tetrahydrofuran) until no more unquaternized ester remained. Evaporation of the solvent in vacuo gave a residue which was washed several times with dry ether. The red viscous liquid which remained was stored over argon for further use. Yield 97.35%. The product was identified as the desired quaternary salt by NMR analysis. It was assigned the structural formula:

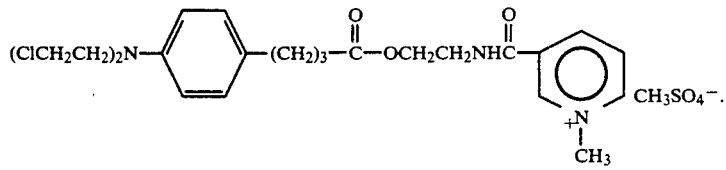

EXAMPLE 78

Preparation of 1-Methyl-3-[(N-{2-[4-({4-[bis(2-chloroethyl)]amino}phenyl)butanoyloxy]ethyl})carbamoyl]-1,4-dihydropyridine The quaternary salt prepared in Example 77 (2.49 g, 0.0043 mol) was dissolved in 350 mL of water. Nitrogen was bubbled through the solution throughout the reaction period. The aqueous solution was cooled over ice to 5° C., then 2.17 g (0.026 mol) of NaHCO₃ were added over a 5 minute period, followed by 2.997 g (0.017 mol) of sodium dithionite over a 10 minute period. The reaction mixture was maintained at 5° C. for 120 minutes, then the layers were separated. The aqueous layer was extracted 4 times with ethyl acetate. The ethyl acetate extracts were combined, dried over MgSO₄ and evaporated to dryness in vacuo. The semi-solid thus obtained was washed several times with dry ether to give the title compound as a yellow solid melting at 90°-92° C. and having the structural formula:

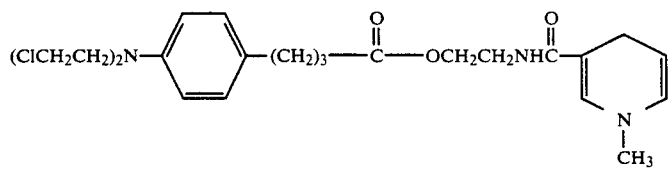

EXAMPLE 79

Preparation of N-(4-Hydroxycyclohexyl)-3-pyridinecarboxamide

Trans-4-aminocyclohexanol hydrochloride (5.05 g, 0.033 mol) was suspended in 50 mL of ethanol, then 33 mL of 1N NaOH were added slowly while cooling the reaction mixture to 10° C. The homogeneous mixture was evaporated to dryness, then three portions of a 50:50 mixture of benzene and acetone were added and evaporated to dryness in vacuo each time. The dry solid was extracted with 100 mL of chloroform and filtered, and the filtrate was evaporated to dryness. The residue was triturated with ether and dried to give 3.50 g (91.23%) of the free aminocyclohexanol melting at 111°-112° C.

Nicotinic acid (2.14 g, 0.017 mol) was suspended in 75 mL of dry tetrahydrofuran, then 1.76 g of freshly distilled triethylamine were added. The clear solution thus obtained was cooled to −4° C. in an ice bath under argon, then ethyl chloroformate (1.88 g, 0.014 mol) in 10 mL of tetrahydrofuran was added such that the temperature did not go above 0° C. The free aminocyclohexanol (2.0 g, 0.017 mol) was added as a powder to the cold reaction mixture, which was allowed to come to room temperature and stirred for 2 hours. The precipitate which formed was collected by filtration, dissolved in 28 mL of hot water and recrystallized as 3.25 g (85%) of fine colorless needles melting at 208°-210° C. and having the formula

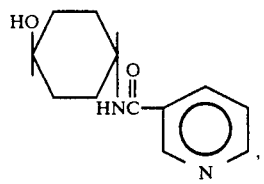

as confirmed by elemental analysis.

EXAMPLE 80

Preparation of N-{4-[4-({4-[Bis(2-chloroethyl)]amino}-phenyl)butanoyloxy]cyclohexyl}-3-pyridinecarboxamide Chlorambucil (1.38 g, 0.0045 mol) and N-(4-hydroxycyclohexyl)-3-pyridinecarboxamide (1.1 g, 0.0049 mol) were mixed together with 1.03 g (0.00459 mol) of dicyclohexylcarbodiimide and 55 mg (0.00045 mol) of 4-(dimethylamino)pyridine (DMAP) in 50 mL of freshly distilled acetonitrile. The reaction mixture was stirred at room temperature in the presence of argon for 2 days. The progress of the reaction was followed by thin layer chromatography using 8:2 chloroform/tetrahydrofuran. At the end of the reaction period, the precipitate was removed by filtration and the filtrate was evaporated to dryness in vacuo at low temperature. The residue was applied to a silica column and eluted with 8:2 chloroform/tetrahydrofuran. The appropriate eluting portions were combined and evaporated to dryness in vacuo. The product (1.86 g, 81%) was obtained as a light cream-colored powder melting at 120°-122° C. and having the formula

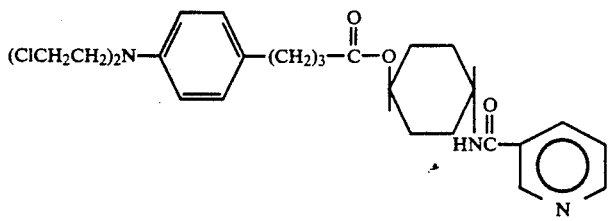

The identity of the product was confirmed by elemental analysis.

EXAMPLE 81

Preparation of
1-Methyl-3-(N-{4-[4-(4-{[bis(2-chloroethyl)]amino}phenyl)butanoyloxy]cyclohexyl}carbamoyl)-pyridinium methanosulfate The product of Example 80 (1 g, 0.0019 mol) was dissolved in 30 mL of dry acetonitrile and 0.249 g (0.0019 mol) of dimethyl sulfate was added. The mixture was refluxed under argon until thin layer chromatography (8:2 chloroform/tetrahydrofuran on silica) indicated quaternization was complete (about one and one-half days). The solvent was evaporated in vacuo, leaving an orange residue which was washed several times with anhydrous ether and evaporated in vacuo. The quaternary salt (1.04 g, 80.6%) was obtained as a sticky yellow mass. It had the structural formula:

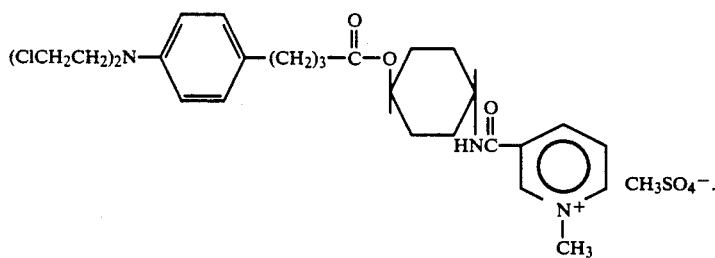

EXAMPLE 82

Preparation of
1-Methyl-3-(N-{4-[4-(4-{[bis(2-chloroethyl)]amino}phenyl)butanoyloxy]cyclohexyl}carbamoyl)-1,4-dihydropyridine The quaternary salt prepared in Example 81 (0.34 g, 0.0005 mol) was dissolved in 0.5 mL of acetonitrile and taken up in 20 mL of degassed water (bubbling N₂) cooled to 0° C. To the stirring solution, sodium bicarbonate (0.27 g, 0.003 mol) was added, followed first by 0.37 g (0.002 mol) of sodium dithionite and then by 20 mL of ethyl acetate. After 90 minutes, the organic phase was removed and the aqueous phase was extracted 3 to 4 times with ethyl acetate. The ethyl acetate extracts were combined, dried over sodium sulfate and evaporated in vacuo. The residual solid was washed several times with anhydrous ether and dried. The residue thus obtained was applied to a neutral alumina column and eluted with chloroform under pressure. Evaporation of chloroform left 0.18 g (65%) of a hygroscopic yellow solid of the formula

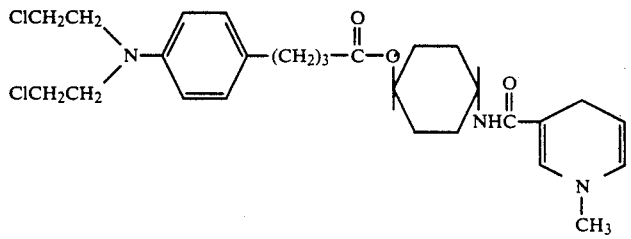

The identity of the product was confirmed by UV analysis.

EXAMPLE 83

Preparation of
N-(2-Hydroxy)propyl-3-pyridinecarboxamide

To 4.29 g (0.039 mol) of nicotinic acid suspended in 120 mL of dry tetrahydrofuran, 4.04 g (0.039 mol) of freshly distilled triethylamine was added in one portion. The resultant clear solution was cooled to −4° C. in an ice bath under argon. Ethyl chloroformate (4.33 g, 0.039 mol) in 25 mL of tetrahydrofuran was added at such a rate that the temperature of the solution did not exceed 0° C. Then, 3 g (0.039 mol) of 1-amino-2-propanol were added directly to the cold reaction mixture. The reaction mixture was allowed to come to room temperature and stirred for 2 hours. The precipitate was removed by filtration and the filtrate was evaporated in vacuo. The oily residue was washed several times with anhydrous ether and allowed to stand. The title compound was obtained as a white, hygroscopic, low-melting, waxy solid melting at 40° C. (6.11 g, 85%) and having the formula

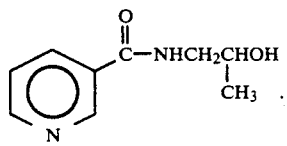

EXAMPLE 84

Preparation of
N-{2-[4-({4-[Bis(2-chloroethyl)]amino}phenyl)-butanoyloxy]propyl}-3-pyridinecarboxamide Chlorambucil (1.0 g, 0.003 mol) and N-(2-hydroxy)-propyl-3-pyridinecarboxamide (0.065 g, 0.0036 mol) were combined with 0.68 g (0.003 mol) of dicyclohexylcarbodiimide and 41 mg (0.0003 mol) of 4-(dimethylamino)pyridine (DMAP) in 40 mL of freshly distilled acetonitrile. The reaction mixture was stirred at room temperature in the presence of argon for 2 days, the progress of the reaction being followed by thin layer chromatography on silica using 8:2 methylene chloride/ethyl acetate. At the end of the reaction period, the precipitate was removed by filtration and the filtrate was evaporated to dryness in vacuo at 30° C. The residue was applied to a silica column and eluted with 8:2 methylene chloride/ethyl acetate. The appropriate eluting portions were combined and evaporated to dryness in vacuo. The title compound was obtained as a sticky material in 84% yield (1.53 g). It had the structural formula:

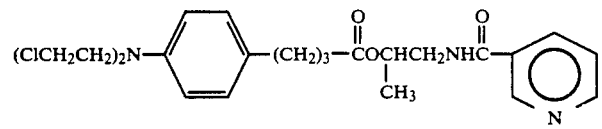

EXAMPLE 85

Preparation of
1-Methyl-3-[(N-{2-[4-({4-[bis(2-chloroethyl)]amino}phenyl)butanoyloxy]propyl})carbamoyl]pyridinium methanosulfate The product of Example 84 (2.2 g, 0.0047 mol) was dissolved in 45 mL of dry acetonitrile, dimethyl sulfate (0.59 g, 0.0047 mol) was added and the mixture was refluxed under argon. The progress of the reaction was followed by thin layer chromatography using 8:2 methylene chloride/ethyl acetate. After one and one-half days, the solvent was removed by evaporation in vacuo, leaving an orange residue. The residue was washed thoroughly with anhydrous ether and was dried in vacuo. The product, obtained as a yellow sticky mass in 92.47% yield, had the structural formula:

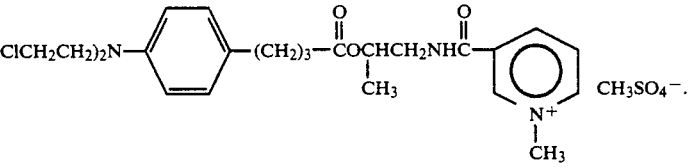

EXAMPLE 86

Preparation of
1-Methyl-3-[(N-{2-[4-({4-[bis(2-chloroethyl)]amino}phenyl)butanoyloxy]propyl})carbamoyl]-1,4-dihydropyridine The quaternary salt prepared in Example 85 (2.39 g, 0.004 mol) was dissolved in 1 mL of acetonitrile and then taken up in 100 mL of degassed water (bubbling $N_2$) and cooled to 0° C. in an ice-water bath. Sodium bicarbonate (2.03 g, 0.024 mol) was added to the stirring solution, followed by 2.81 g (0.016 mol) of sodium dithionite. To the resultant mixture, 60 mL of ethyl acetate were added. The reaction was allowed to continue for 90 minutes, then the phases were separated and the aqueous phase was extracted 3 or 4 times with 30 mL portions of ethyl acetate. The combined ethyl acetate extracts were dried over sodium sulfate and evaporated in vacuo. The residue was applied to a neutral alumina column and eluted with chloroform under pressure. The appropriate fractions were evaporated to give a hygroscopic yellow solid in 60% yield. The product had the formula:

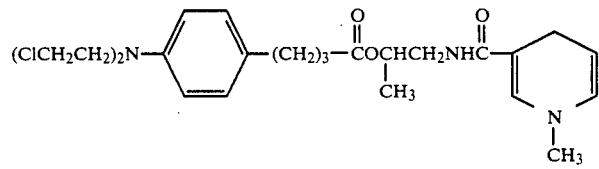

as confirmed by UV analysis.

EXAMPLE 87

Preparation of
N-(2-Hydroxy-2-phenyl)ethyl-3-pyridinecarboxamide

Nicotinic acid (1.79 g, 0.014 mol) was suspended in 60 mL of dry tetrahydrofuran and 1.48 g (0.014 mol) of freshly distilled triethylamine were added. The clear solution which resulted was cooled to −4° C. in an ice bath and argon was bubbled through it continuously. Ethyl chloroformate (1.58 g, 0.014 mol) in 10 mL of tetrahydrofuran was added at such a rate that the temperature did not exceed 0° C. Then, 2.0 g (0.014 mol) of 2-amino-1-phenylethanol were added as a solution in 5 mL of tetrahydrofuran. The reaction mixture was allowed to warm to room temperature and was stirred for 2 hours. The precipitate which formed was removed by filtration and the filtrate was evaporated in vacuo to give 3.22 g (91.1%) of a white crystalline solid melting at 122°–124° C. and having the formula

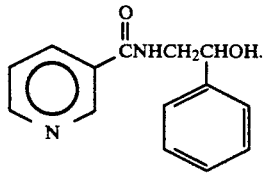

Elemental analysis confirmed the identity of the product.

EXAMPLE 88

Preparation of N-({2-Phenyl-2-[4-({4-[bis(2-chloroethyl)]amino}phenyl)butanoyloxy]}ethyl)-3-pyridinecarboxamide Chlorambucil (1.0 g, 0.003 mol) and N-(2-hydroxy-2-phenyl)ethyl-3-pyridinecarboxamide (0.88 g, 0.003 mol) were combined with 0.68 g (0.003 mol) of dicyclohexylcarbodiimide and 41 mg (0.0003 mol) of 4-(dimethylamino)pyridine (DMAP) in 35 mL of freshly distilled acetonitrile. The reaction mixture was stirred at room temperature under argon for 3 days. Thin layer chromatography using 8:2 methylene chloride/ethyl acetate was used to follow the progress of the reaction. The precipitate which formed was removed by filtration and the acetonitrile was evaporated in vacuo. The residue thus obtained was applied to a silica column and eluted with 8:2 methylene chloride/ethyl acetate. The appropriate fractions were collected and evaporated in vacuo to give a light tan powder (1.21 g, 70%) melting at 99°–101° C. and having the formula

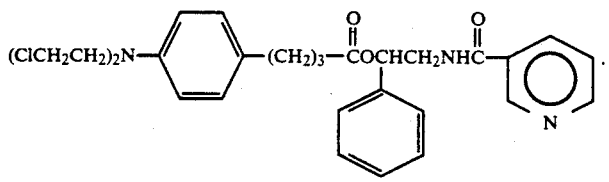

EXAMPLE 89

Preparation of 1-Methyl-3-[(N-{2-phenyl-2-[4-({4-[bis(2-chloroethyl)]amino}phenyl)butanoyloxy]}ethyl)carbamoyl]-pyridinium methanosulfate The product of Example 88 (0.5 g, 0.00094 mol) was dissolved in 20 mL of dry acetonitrile and 0.12 g (0.00094 mol) of dimethyl sulfate was added. The mixture was refluxed under argon for 2 days, then the solvent was removed by evaporation in vacuo. The residue which was obtained was washed several times with anhydrous ether and dried to give 0.54 g (91%) of a sticky light yellow product having the formula

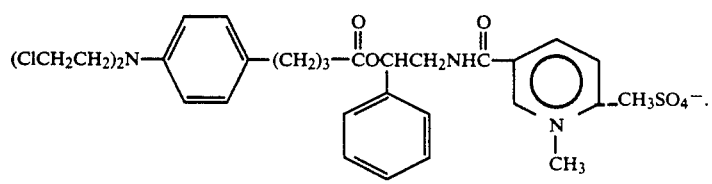

EXAMPLE 90

Preparation of 1-Methyl-3-[(N-{2-phenyl-2-[4-({4-[bis(2-chloroethyl)]amino}phenyl)butanoyloxy]}ethyl)carbamoyl-1,4-dihydropyridine The quaternary salt prepared in Example 89 (0.53 g, 0.0008 mol) was dissolved in 0.5 mL of acetonitrile and taken up in 20 mL of degassed, deionized water cooled to 0° C. Sodium bicarbonate was added to the stirring solution at 0° C., followed by 0.56 g (0.0032 mol) of sodium dithionite. Then, 20 mL of ethyl acetate were added and the reaction was allowed to continue for 2 hours. The organic phase was removed and the aqueous phase was extracted several times with ethyl acetate (total volume 70 mL), until color was no longer observed in the organic phase. The ethyl acetate extracts were combined and dried over sodium sulfate and evaporated in vacuo. The residue was applied to a neutral alumina column and eluted with chloroform. Evaporation of chloroform gave 0.2 g (45%) of a hygroscopic orangish yellow compound of the formula

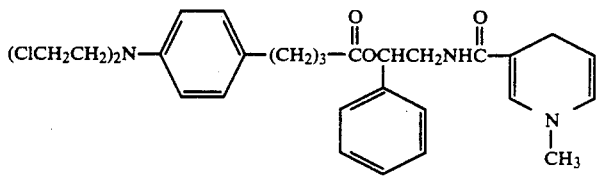

The identity of the product was confirmed by UV spectral analysis.

EXAMPLE 91

Preparation of N-(2-Hydroxyethyl)-3-pyridinecarboxamide

A neat mixture of 2-aminoethanol (6.1 g, 0.10 mol) and ethyl nicotinate (15.1 g, 0.10 mol) was refluxed overnight. As the mixture was cooled to room temperature, the product precipitated as a crystalline solid. It was filtered, washed with ether and then recrystallized from 2-propanol/ether. The final product was collected by vacuum filtration and washed with ether. The dried, white compound weighed 10.7 g, resulting in a 64.5% yield; mp 88.5°–89.5° C. (lit. value 92° C.).

EXAMPLE 92

Preparation of (+)N-[2-(6-Methoxy-α-methyl-2-naphthalenylacetoxy)ethyl]-3-pyridinecarboxamide Naproxen (2.30 g, 10.0 mmol) was coupled with the product of Example 91 (1.71 g, 10.0 mmol) using dicyclohexylcarbodiimide (2.30 g, 11.0 mmol) and 4-(dimethylamino)pyridine (122 mg, 1.00 mmol) in acetonitrile (150 mL). The reaction was stirred at room temperature for 48 hours. The precipitate was filtered, rinsed with acetonitrile and dried to a weight of 2.3 g. The solvent was removed under reduced pressure and the residual clear oil was stirred with anhydrous ether. The resulting white solid was vacuum filtered, washed with ether and air-dried. The crude product weighed 2.80 g. The compound was recrystallized from 2-propanol. The final product was filtered, washed with 0.5% aqueous sodium bicarbonate, water, and finally with ether. The compound was dried in a desiccator over $P_2O_5$. The recrystallized material weighed 2.40 g resulting in an overall yield of 63.4%; mp 79°–82° C.

EXAMPLE 93

Preparation of N-(2-{[1-(p-Chlorobenzoyl)-5-methoxy-2-methyl-3-indolyl]acetoxy}ethyl)-3-pyridinecarboxamide A reaction of indomethacin (1.79 g, 5.00 mmol) and the product of Example 91 (0.830 g, 5.00 mmol) was carried out, using dicyclohexylcarbodiimide (1.10 g, 5.50 mmol) as the coupling agent and acetonitrile as the solvent. The first two reactants were dissolved completely and the solution was then cooled to 0° C. The dicyclohexylcarbodiimide was added and the mixture was stirred overnight. The reaction was allowed to continue for 48 hours. The precipitate (1.2 g) was removed by vacuum filtration. The solvent was removed from the filtrate under reduced pressure leaving an oily residue. The product was solidified by stirring with anhydrous ether. It was filtered, air-dried and recrystallized from ethanol/ether. The final product was vacuum filtered, washed with ether, and air dried. The product weighed 1.65 g, giving a 65.2% yield; mp 123°–125° C.

EXAMPLE 94

Preparation of 1-Methyl-3-{N-[2-(6-methoxy-α-methyl-2-naphthalenylacetoxy)ethyl]carbamoyl}pyridinium iodide The quaternization of the naproxen ester prepared in Example 92 (1.0 g, 2.6 mmol) was carried out using methyl iodide (2.3 g, 16 mmol) in acetone (45 mL). The solution was heated to reflux for 20 hours. Methyl iodide (1.1 g, 8.0 mmol) was again added to the reaction flask. The precipitated product was filtered after an additional 4 hours of reaction time. The off-white powder was dried. The material weighed 2.2 g and was found to be analytically pure without recrystallization. The solvent was removed from the acetone filtrate and the residue was solidified with anhydrous ether. The resulting dark yellow powder was dissolved in water and washed with ether (4×30 mL). The water was then removed under vacuum giving 0.2 g of a lighter yellow powder. The overall yield of the reaction was 93%; mp 169°–170° C. The product had the structural formula

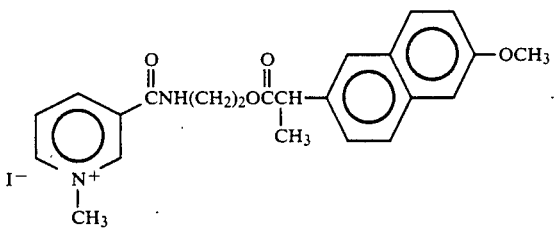

as further confirmed by UV, NMR and elemental analyses.

EXAMPLE 95

Preparation of 1-Methyl-3-[N-(2-{[1-(p-chlorobenzoyl)-5-methoxy-2-methyl-3-indolyl]acetoxy}ethyl)carbamoyl]pyridinium iodide The quaternization of the indomethacin ester prepared in Example 93 (0.50 g, 1.0 mmol) was carried out in acetone, using methyl iodide (1.7 g, 12 mmol). The reaction was refluxed overnight. The solvent was removed under reduced pressure and a yellow solid was obtained. The product was recrystallized using ethanol and a very small amount of ether. Small mold-like crystals were obtained which were light yellow in color. The reaction gave 0.43 g or a 66% yield of the purified material; mp 178°–179° C. UV, NMR and elemental analyses confirmed that the product had the structural formula:

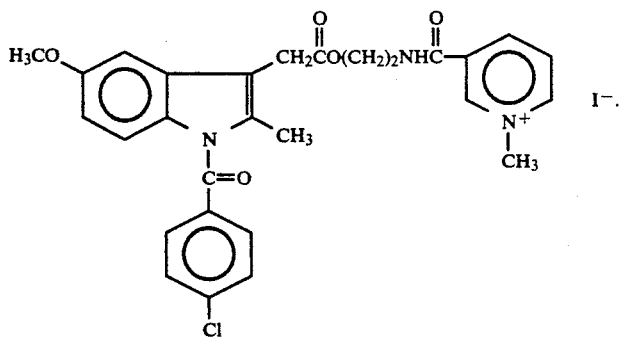

EXAMPLE 96

Preparation of 1-Methyl-3-{N-[2-(6-methoxy-α-methyl-2-naphthalenylacetoxy)ethyl]carbamoyl}-1,4-dihydropyridine The quaternary salt prepared in Example 94 (780 mg, 1.5 mmol) was dissolved in degassed, deionized water (200 mL) and acetonitrile (10 mL). Sodium dithionite (780 mg, 4.5 mmol) and sodium bicarbonate (630 mg, 7.5 mmol) were combined and added to the solution at room temperature. The reaction was continued for 1 hour, while nitrogen gas was slowly bubbled through the solution. The partially precipitated product was extracted repeatedly with ether (8×30 mL). The extracts were combined, washed with water (25 mL) and dried over magnesium sulfate. The drying agent was filtered and the solvent was removed from the filtrate under reduced pressure. The oily residue was dissolved in methylene chloride (3×5 mL) and removed under reduced pressure. The resulting foam was rinsed with anhydrous ether (3 mL) and the solvent was removed under vacuum. The final product weighed 390 mg, giving a 66% yield. The hygroscopic solid foam was stored under nitrogen at −100° C. It had the structural formula:

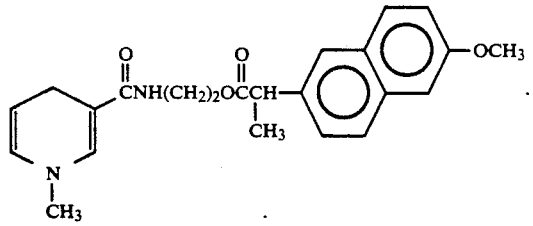

as confirmed by UV, NMR and elemental analyses.

EXAMPLE 97

Preparation of 1-Methyl-3-[N-(2-{[1-(p-chlorobenzoyl)-5-methoxy-2-methyl-3-indolyl]acetoxy}ethyl)carbamoyl]-1,4-dihydropyridine The indomethacin quaternary salt prepared in Example 95 (140 mg, 0.22 mmol), was dissolved in a minimum amount of water:acetonitrile (8:2). The water had been bubbled with nitrogen for 20 minutes prior to its use. Sodium bicarbonate (91 mg, 1.1 mmol) and sodium dithionite (110 mg, 0.65 mmol) were added to the solution while stirring at 0° C. The solution was then allowed to warm to room temperature. The reaction was continued for about 1 hour. Some of the product had precipitated during the reaction. This was dissolved in ethyl ether. The water layer was extracted several times with ether until no more yellow color transferred to the organic layer. The ether portions were combined and dried with magnesium sulfate, filtered and the ether was removed under reduced pressure. The resulting oil was dissolved in acetone and the solvent was removed (2×10 mL) under reduced pressure to form a dry foam. The final product weighed 92 mg. The yield was 82%; mp 60°-65° C. The product had the formula:

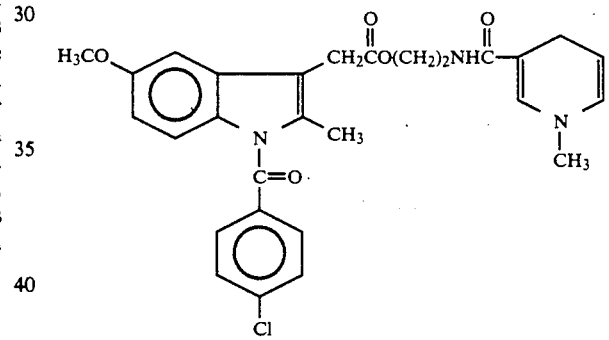

as confirmed by UV, NMR and elemental analyses.

EXAMPLE 98

Preparation of N-[(1-Hydroxycyclohexyl)methyl]-3-pyridinecarboxamide

To 1.48 g (0.012 mol) of nicotinic acid suspended in 50 mL of dry tetrahydrofuran, 2.44 g (0.014 mol) of freshly distilled triethylamine were added, with stirring. The resultant clear solution was cooled to −4° C. in an ice bath, under argon. Then, 1.3 g (0.012 mol) of ethyl chloroformate in 10 mL of tetrahydrofuran were added at such a rate that the temperature of the reaction mixture did not exceed 0° C. To the cold reaction mixture, 2.0 g (0.012 mol) of 1-aminomethyl-1-cyclohexanol hydrochloride were added directly as a powder. The reaction mixture was allowed to warm to room temperature and stirred for 2 hours, then the triethylamine hydrochloride which formed was removed by filtration and the filtrate was evaporated in vacuo to afford a white solid. The solid was recrystallized from water, washed with acetone and ether and dried. The title compound, obtained in 85% yield (2.4 g), melted at around 110° C., and was further characterized by the structural formula

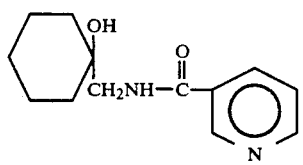

as confirmed by elemental analysis.

EXAMPLE 99

Preparation of
N-({1-[4-({4-[Bis(2-chloroethyl)]amino}phenyl)-butanoyloxy]cyclohexyl}methyl)-3-pyridinecarboxamide Chlorambucil (1.18 g, 0.0038 mol) and N-[(1-hydroxycyclohexyl)methyl]-3-pyridinecarboxamide (0.99 g, 0.004 mol) were combined with 0.8 g (0.0038 mol) of dicyclohexylcarbodiimide and 47 mg (0.00038 mol) of 4-(dimethylamino)pyridine (DMAP) in 60 mL of freshly distilled acetonitrile. The reaction mixture was stirred at room temperature under argon for 7 days. At the end of that time, the precipitate which formed was separated by filtration and the filtrate was evaporated to dryness at low temperature in vacuo. The residue was applied to a silica column and eluted, first with 8:2 methylene chloride/ethyl acetate, then with 8:2 chloroform/tetrahydrofuran. The appropriate eluting portions were combined and evaporated to dryness in vacuo. The title compound was obtained in 26% yield as a light yellow solid melting at 92°–94° C. It had the structural formula

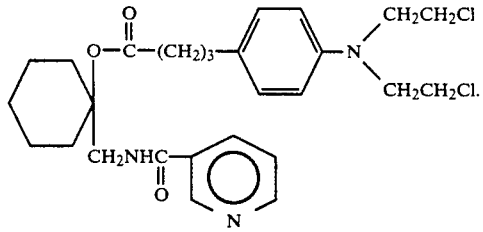

as confirmed by elemental analysis.

EXAMPLE 100

Preparation of
1-Methyl-3-[N-({1-[4-(4-{[bis(2-chloroethyl)]amino}phenyl)butanoyloxy]cyclohexyl}methyl)carbamoyl]-pyridinium methanosulfate:

To 0.69 g (0.0013 mol) of the product of Example 99, dissolved in 25 mL of dry acetonitrile, was added 0.17 g (0.0013 mol) of dimethyl sulfate. The mixture was refluxed until the reaction was complete (approximately 2 days), as evidenced by thin layer chromatography using 8:2 chloroform/tetrahydrofuran. The solvent was removed by evaporation in vacuo to afford an orange residue, which was washed several times with anhydrous ether and dried. The product was obtained as a sticky yellow mass (85%, 0.72 g) having the formula:

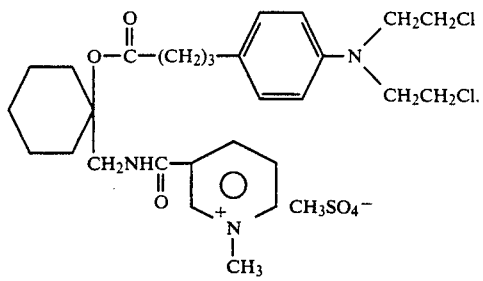

EXAMPLE 101

Preparation of
1-Methyl-3-[N-({1-[4-(4-{[bis(2-chloroethyl)]amino}phenyl)butanoyloxy]cyclohexyl}methyl)carbamoyl-1,4-dihydropyridine The quaternary salt prepared in Example 100 (0.78 g, 0.0012 mol) was dissolved in 0.5 mL of acetonitrile and taken up in 20 mL of water degassed with bubbling $N_2$, cooled to 0° C. To the stirring solution, 0.61 g (0.0072 mol) of sodium bicarbonate was added, followed by 0.84 g (0.0048 mol) of sodium dithionite and 20 ml of ethyl acetate. The reaction was allowed to proceed for 75 minutes, then the layers were separated and the aqueous layer was extracted 3 to 4 times with 20 mL of ethyl acetate. The organic extracts were combined, dried over sodium sulfate and evaporated in vacuo. The residue was applied to a neutral alumina column and eluted with chloroform under pressure. Evaporation afforded the product as a sticky yellow mass (0.31 g, 49%) having the structural formula:

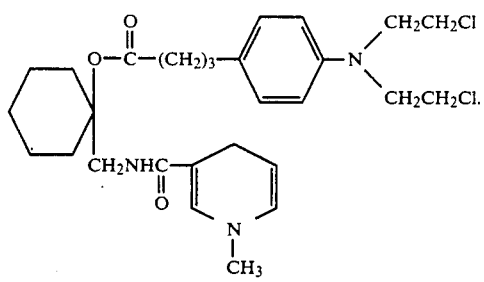

EXAMPLE 102

Preparation of
1-Methyl-3-{[2-(9-guanylmethoxy)ethoxy]carbonyl}-pyridinium iodide Trigonelline anhydride diiodide (1-methylpyridinium-3-carboxylic acid anhydride diiodide) was prepared as described by Brewster et al, *Synthetic Communications*, 17(4), 451–455 (1987).

To a solution of 1.0 g (4.4 mmol) of acyclovir in 25 mL of freshly distilled dry pyridine were added 2.27 g (4.4 mmol) of trigonelline anhydride diiodide and a catalytic amount (5.4 mg, 4 mmol) of 4-(dimethylamino)pyridine (DMAP). The resultant suspension was stirred for 4 days under argon at room temperature. As the reaction proceeded, the orange color of the anhydride was replaced with a yellow color. When all of the acyclovir had been consumed, the reaction was stopped, the precipitate (containing the product ester plus the trigonelline formed as a by-product) was removed by filtration and washed with acetone and ether to remove DMAP. The yellow solid was then stirred in dry methanol at room temperature to remove trigonelline, unreacted anhydride and acyclovir. The title compound was obtained in 87% yield (1.82 g), melting at 201°–202° C. NMR and UV analyses confirmed that the product had the formula:

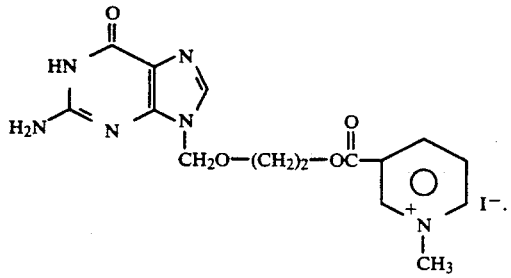

EXAMPLE 103

Preparation of 1-Methyl-3-{[2-(9-guanylmethoxy)ethoxy]carbonyl}-1,4-dihydropyridine To a solution of 1.58 g (3.3 mmol) of the product of Example 102 in 120 mL of degassed water were added 1.69 g (20.1 mmol) of $NaHCO_3$ in one portion. The mixture was stirred at 0° C. while 2.33 g (13.18 mmol) of sodium dithionite were added over a 5 minute period. The flask was flushed with nitrogen throughout the reaction process. The dihydropyridine product was insoluble in water and formed cream-colored crystals on top of the water layer. The crystals were separated by filtration and washed, first with ice-cold water and then with anhydrous ether. Drying over $P_2O_5$ in a dessicator maintained at $-15°$ C. afforded 0.626 g (54%) of the title compound melting at 163°–165° C. NMR and UV analyses confirmed that the product had the formula:

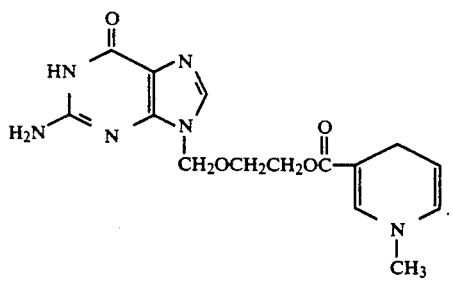

EXAMPLE 104

Preparation of 5'-Pivaloyltrifluorothymidine

To a stirring solution of 150 mg of trifluorothymidine in 5 mL of pyridine was added a solution of 90 mg of pivaloyl chloride in 1 mL of pyridine, with cooling. Stirring was continued at room temperature for 10 hours, then the reaction mixture was poured into 20 mL of ice water and extracted with 50 mL of ethyl acetate. The extract was washed with water and dried over sodium sulfate. The ethyl acetate was removed and the residue was purified by silica gel column chromatography using 20:1 chloroform/methanol as eluent. The title compound melted at 130°–132° C. after recrystallization from a mixture of ether and n-hexane.

EXAMPLE 105

Preparation of 3'-(3-Pyridylcarbonyl)-5'-pivaloyltrifluorothymidine

To a stirring solution of 450 mg of 5'-pivaloyltrifluorothymidine

To a stirring solution of 450 mg of 5'-pivaloyltrifluorothymidine in 10 mL of pyridine was added 1.0 g of nicotinoyl chloride hydrochloride under ice-cooling. The reaction mixture was stirred at room temperature for 3 days, then was poured into 100 mL of ice water and extracted with 100 mL of ethyl acetate. The extract was washed with water, dried over anhydrous sodium sulfate and then evaporated in vacuo to give an oil. Crystallization from n-hexane afforded 500 mg (87%) of colorless needles melting at 175°–177° C. The product had the structure

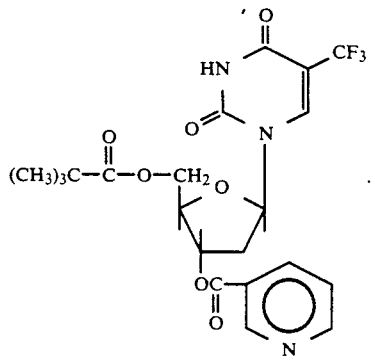

as further confirmed by NMR spectral analysis.

EXAMPLE 106

Preparation of 3'-(1-Methyl-3-pyridiniumcarbonyl)-5'-pivaloyltrifluorothymidine iodide To 440 mg of the product of Example 105 dissolved in 10 mL of acetone, 1.0 g of methyl iodide was added. The mixture was refluxed for 10 hours, then the precipitate which formed was collected by suction filtration to give 550 mg of the desired product as yellow leaves melting at 188°–190° C. with decomposition. NMR analysis confirmed that the product had the structural formula:

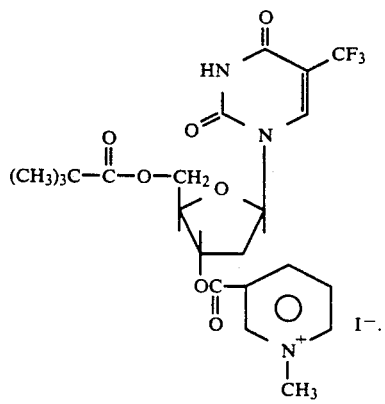

EXAMPLE 107

Preparation of 3'-(1,4-Dihydro-1-methyl-3-pyridinylcarbonyl)-5'-pivaloyltrifluorothymidine To a stirring solution of 100 mg of the product of Example 106 in a mixture of 20 mL of water and 20 ml of ethyl acetate were added 64 mg of NaHCO$_3$ and 115 mg of Na$_2$S$_2$O$_4$ under N$_2$ gas. The resultant mixture was stirred at room temperature for 1 hour, then the organic layer was separated and washed with water. The extract was dried over anhydrous Na$_2$SO$_4$ and evaporated in vacuo. The residue was triturated with a mixture of ether and n-hexane and the yellow needles which formed were collected by suction filtration (50 mg, 62%). The product melted at 168°–170° C. NMR analysis confirmed that the product had the structural formula:

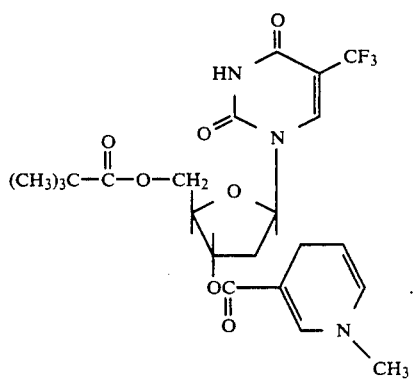

EXAMPLE 108

Preparation of 3'-Azido-3'-deoxy-5'-(3-pyridylcarbonyl)thymidine

A mixture of 1.18 g (4.42 mmol) of azidothymidine, 1.11 g (4.86 mmol) of nicotinic anhydride and 0.15 g (1.22 mmol) of N-(dimethylamino)pyridine was combined in 50 mL of pyridine. The reaction mixture was stirred at room temperature overnight. The clear, colorless reaction mixture was concentrated in vacuo to a semisolid opaque mass which was triturated with ether overnight. The suspension was filtered and dried to give 1.97 g of solid. Then, 1.0 g of the solid was chromatographed over 20 g of silica gel using 10% ethanol/chloroform as eluent. The desired fraction was isolated as 0.53 g of a white foam, which was crystallized from a solvent mixture of ethanol, diethyl ether and hexane. The product melted at 138.5°–141.5° C. and had the structural formula

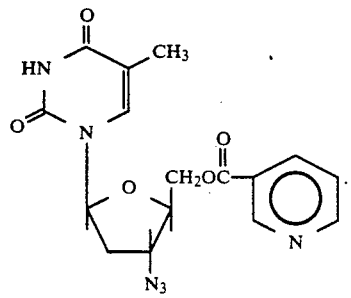

as confirmed by NMR and IR.

EXAMPLE 109

Preparation of 3'-Azido-3'-deoxy-5'-[(1-methyl-3-pyridinium)carbonyl]thymidine iodide A mixture of 0.53 g (2.0 mmol) of azidothymidine, 1.02 g (2.2 mmol) of trigonelline anhydride diiodide and 67 mg (0.5 mmol) of N-(dimethylamino)pyridine was combined in 25 mL of pyridine. The reaction mixture was stirred at room temperature for 5 days, then was filtered. The filtrate was concentrated in vacuo to a residue which was triturated with acetone overnight. The resulting suspension was filtered and the filtrate was concentrated in vacuo to a foam, which was treated with water and filtered to remove a small amount of insoluble material. The filtrate was concentrated in vacuo to a solid yellow glass (0.50 g, 49%). NMR and UV analysis confirmed that the product had the formula:

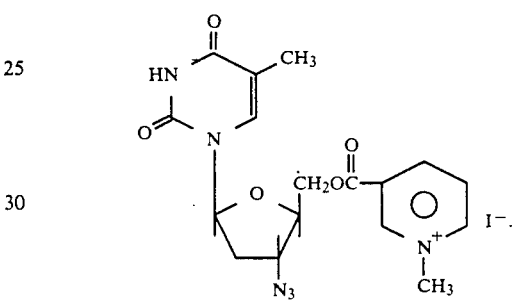

EXAMPLE 110

Preparation of 3'-Azido-3'-deoxy-5'-[(1-methyl-1,4-dihydro-3-pyridinyl)carbonyl]thymidine The crude azidothymidine quaternary derivative prepared according to the procedure of Example 109 (1.45 g, 2.82 mmol) was dissolved in 50 mL of water and filtered. The filtrate was cooled in an ice bath and saturated with argon. Then, 100 mL of ethyl acetate and 2.90 g of NaHCO$_3$ were added, followed by 1.45 g of Na$_2$S$_2$O$_4$ after 5 minutes. The reaction was allowed to proceed for 1 hour, then the ethyl acetate layer was removed and fresh ethyl acetate was added. This procedure was repeated to give three organic extracts and a reaction time of 3 hours. The extracts were pooled and concentrated in vacuo to a foam weighing 1.01 g (92%). The foam was crystallized from methanol to give the title compound of the formula

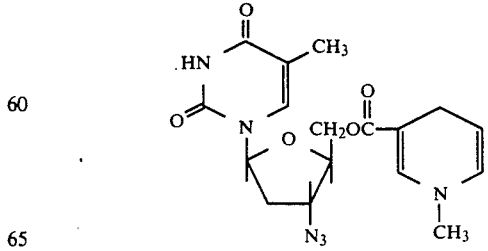

melting at 138°–140° C. Its structure was confirmed by elemental analysis as well as NMR and UV.

EXAMPLE 111

Preparation of Dopamine dipivalate, oxalate salt

To a stirred mixture of 28.1 g of pivaloyl chloride and 150 mL of trifluoroacetic acid, 18.01 g of dopamine hydrobromide were added. The mixture was stirred for 2 hours, then 14 mL of water were added and the mixture was concentrated in vacuo. The residual oil was dissolved in chloroform and washed with cold 10% KHCO3 solution until CO2 evolution ceased. The layers were separated and washed with water and the chloroform layer was dried over MgSO4, filtered and evaporated to dryness. The residue was taken up in 100 ml of ethyl acetate and 7 g of oxalic acid were added together with 100 mL of ethyl acetate. The resultant solution was filtered to remove insoluble materials and 1.6 g oxalic acid in 25 mL of ethyl acetate were added. The mixture was concentrated in vacuo and cooled. The crystals which formed were isolated by filtration, giving 13 g of the title compound. Cooling of the mother liquor afforded a second crop of crystals (5.9 g). The product had the formula:

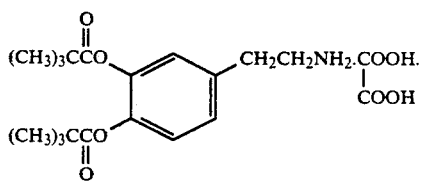

EXAMPLE 112

Preparation of Chloromethyl N-{β-[3,4-bis(pivalyloxy)phenyl]ethyl}aminocarboxylate Dopamine dipivalate, oxalate salt (822 mg, 2 mmol) was suspended in 15 mL of dry tetrahydrofuran. Triethylamine (278 mL, 1 mmol) was added, the mixture was stirred for 15 minutes and a further 278 mL (1 mmol) of triethylamine were then added. Addition of ClCO2CH2Cl (390 mg, 6 mmol) resulted in immediate formation of a heavy white precipitate and the evolution of gas. The reaction mixture was stirred overnight at room temperature, then the precipitate was removed by filtration and the filtrate was washed with 10 mL of 0.1M hydrochloric acid. Drying over magnesium sulfate and evaporation to dryness afforded 1.1 g of a golden oil of the structural formula

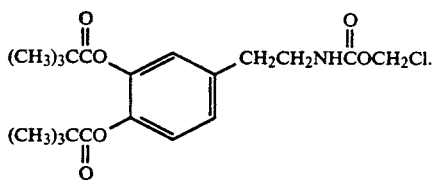

The identity of the product was confirmed by elemental analysis.

EXAMPLE 113

Preparation of N-{β-[3,4-Bis(pivalyloxy)phenyl]ethyl}aminocarbonyloxymethyl 3-pyridinecarboxylate The chloromethyl carbamate prepared in Example 112 (1.26 g, 3.04 mmol) was combined with 10 mL of dry dimethylformamide and that mixture was added to a premixed solution of nicotinic acid (375 mg, 3.04 mmol) and triethylamine (445 mL, 5% excess) in 15 mL of dry dimethylformamide at room temperature. The reaction mixture was stirred for 4 days, then the precipitate which formed was removed by filtration. The filtrate was evaporated to dryness and the residue was taken up in 20 mL of methylene chloride. That solution was washed twice with 10 mL portions of water. Removal of the solvent in vacuo afforded the title compound of the formula:

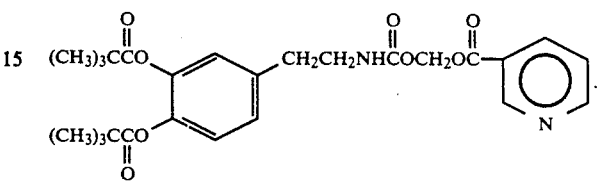

The identity of the product was confirmed by NMR.

EXAMPLE 114

Preparation of N-{β-[3,4-Bis(pivalyloxy)phenyl]ethyl}aminocarbonyloxymethyl 1-methyl-3-pyridinium carboxylate iodide The product of Example 113 (860 mg, 1.78 mmol) was combined with 15 mL of dry acetonitrile and that mixture was treated with 223 mL (3.56 mmol) of methyl iodide. The resultant mixture was stirred for 6 hours at room temperature, then an additional 223 mL (3.56 mmol) of methyl iodide was added and the mixture was stirred overnight. Evaporation to dryness afforded, as an orange-red oil, the title compound of the formula

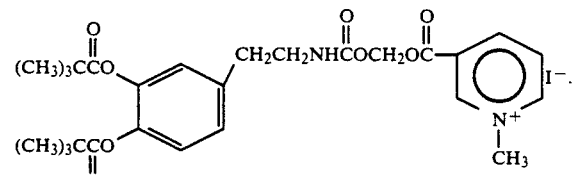

The identity of the product was confirmed by NMR analysis.

EXAMPLE 115

Preparation of N-{β-[3,4-Bis(pivalyloxy)phenyl]ethyl}aminocarbonyloxymethyl 1,4-dihydro-1-methyl-3-pyridinecarboxylate The quaternary salt prepared in Example 114 (54 mg, 0.084 mmol) in 10 mL of water was treated at 0° C. under nitrogen with NaHCO3 (30 mg, 4 eqivalents), Na2S2O4 (60 mg, 4 equivalents) and ethyl acetate (20 mL). The reaction was allowed to proceed for 1 hour 20 minutes, then the aqueous and organic layers were separated and the aqueous layer was re-extracted with 20 mL of ethyl acetate. The combined organics were dried over magnesium sulfate. Removal of the solvent in vacuo gave a red-orange oil which was taken up in chloroform and partially purified by elution with chloroform from a short neutral alumina column. The desired fraction was subjected to preparative thin layer chromatography on silica using 80:20 chloroform/acetone. The highest band was taken as the title compound of the structural formula:

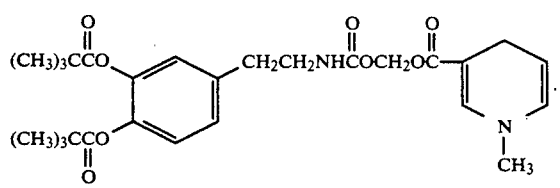

The identity of the product was confirmed by HPLC (high pressure liquid chromatography) determinations for its ability to release dopamine from plasma and brain homogenate.

EXAMPLE 116

Preparation of 9-Fluoro-11β,17-dihydroxy-16α-methyl-21-[(3-pyridinylcarbonyl)oxy]pregna-1,4-diene-3,20-dione Dexamethasone (1 g, 2.5 mmol) was dissolved in 50 mL of dry pyridine. To that solution were added 680 mg (3.0 mmol) of nicotinic anhydride and a trace of 4-(dimethylamino)pyridine (DMAP). The reaction was allowed to proceed for 4 hours, then the reaction mixture was poured over ice water and refrigerated overnight. The solid was collected by filtration and dried to give 1.08 g (87%) of product melting at 262°-265° C. and having the structural formula

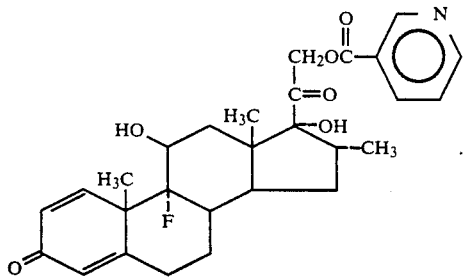

as confirmed by elemental analysis.

EXAMPLE 117

Preparation of 1-Methyl-3-{[(9-fluoro-11β,17-dihydroxy-16α-methyl-pregna-1,4-diene-3,20-dion-21-yl)oxy]carbonyl} pyridinium iodide The product of Example 116 (0.74 g, 1.5 mmol) was dissolved in 50 mL of acetone to which 2 mL of methyl iodide was added. A small amount (10 mL) of CH₃NO₃ was subsequently added to increase solubility. The reaction was allowed to proceed for 2 days, then the solid was collected to give 0.54 g (56% yield) of the title compound melting at 218°-221° C. and having the formula

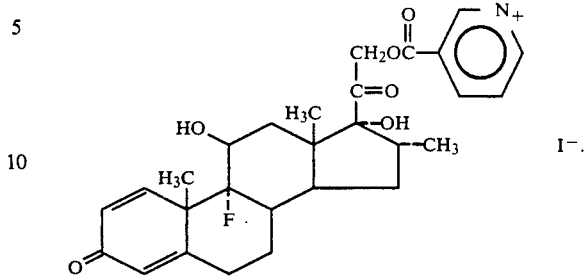

The structure of the product was confirmed by elemental analysis.

EXAMPLE 118

Preparation of 9-Fluoro-11β,17-dihydroxy-16α-methyl-21-{[(1-methyl-1,4-dihydropyridin-3-yl)carbonyl]oxy}pregna-1,4-diene-3,20-dione The general reduction procedure of Example 11 of U.S. Pat. No. 4,617,298 was followed, using 0.78 mmol of the steroidal quaternary salt prepared in Example 117, 0.33 g of NaHCO₃ and 0.41 g of Na₂S₂O₄ in 50% aqueous methanol at 0° C., with a nitrogen purge. The product had the structural formula:

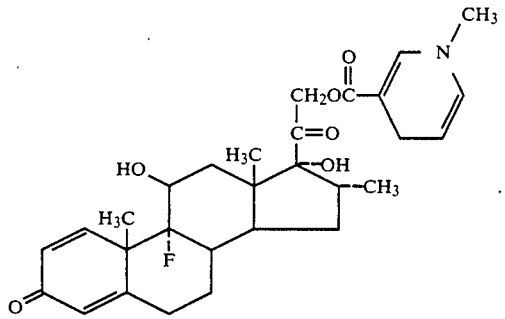

EXAMPLE 119

Preparation of 11β,17-Dihydroxy-21-[(3-pyridinylcarbonyl)oxy]-pregn-4-ene-3,20-dione Hydrocortisone (2 g, 5.5 mmol) was dissolved in 50 mL of dry pyridine. Then, 1.38 g of nicotinoyl anhydride (6.05 mmol) and a trace of 4-(dimethylamino)pyridine (DMAP) were added and the reaction was allowed to proceed for 4 hours at room temperature. The pyridine solution was poured into ice water and the resulting solid was collected by filtration. The solid was dried over P₂O₅ in vacuo to give 2.4 g (93%) of the title compound of the formula

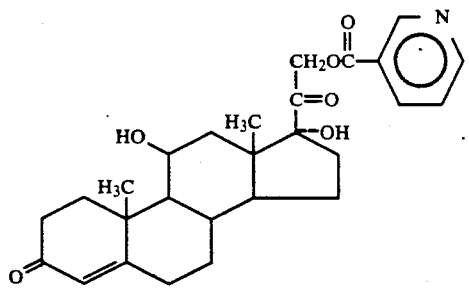

as confirmed by elemental analysis and UV spectral analysis.

EXAMPLE 120

Preparation of
1-Methyl-3-{[(11β,17-dihydroxypregn-4-ene-3,20-dion-21-yl)oxy]carbonyl}pyridinium iodide The product of Example 119 (1 g, 2.1 mmol) was dissolved in 50 mL of acetone and 4 mL of methyl iodide were added. The solution was stirred at the reflux temperature overnight. Removal of the solvent gave the title compound as a yellow powder in 98% yield. Elemental analysis confirmed that the product had the formula:

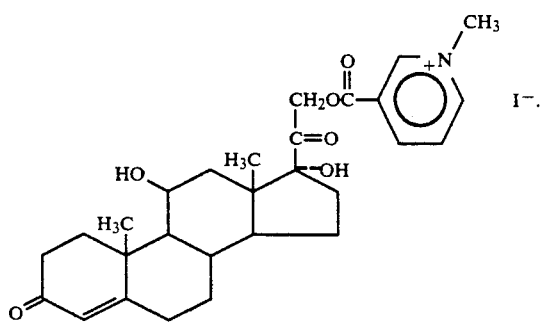

EXAMPLE 121

Preparation of
11β,17-Dihydroxy-21-{[(1-methyl-1,4-dihydropyridin-3-yl)carbonyl]oxy}pregn-4-ene-3,20-dione The general reduction procedure of Example 11 of U.S. Pat. No. 4,617,298 was followed, using 0.8 mmol of the steroidal quaternary salt prepared in Example 120, 0.34 g of NaHCO$_3$ and 0.42 g of Na$_2$S$_2$O$_4$ in 50% aqueous methanol at 0° C., with a nitrogen purge. The product had the structural formula:

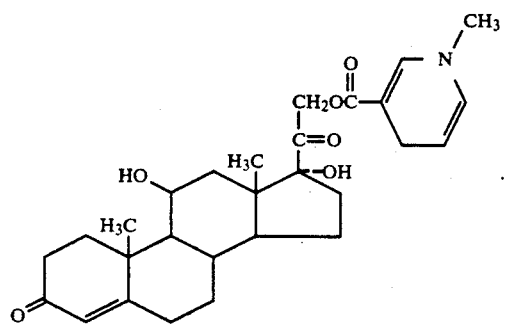

EXAMPLE 122

Preparation of
N-(2-Chloroethyl)-N'-[2-(3-pyridinecarbonyloxy)ethyl]-N-nitrosourea A solution of 2aminoethyl nicotinate dihydrochloride (1.25 g, 52 mmol) and 2,4,5-trichlorophenyl-N-(2-chloroethyl)-N-nitrosocarbamate (2 g, 6 mmol) in 40 mL of pyridine was stirred under nitrogen at room temperature for 24 hours. The reaction was monitored by thin layer chromatography (silica, 1:1 chloroform/ethyl acetate, R$_f$ 0.26). The solvent was removed in vacuo and the residue was chromatographed on a silica gel column by eluting, first with benzene to remove unreacted nitrosocarbamate and trichlorophenol by-product, and then with chloroform, to give the desired product. The resultant oil solidified in the freezer. It melted at 63°–64° C. and had the formula

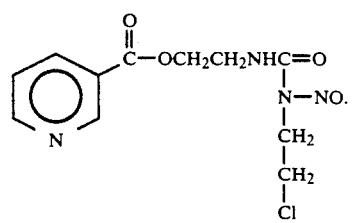

EXAMPLE 123

Preparation of
N-(2-Chloroethyl)-N'-[2-(1-methyl-3-pyridiniumcarbonyloxy)ethyl]-N-nitrosourea iodide A solution of the product of Example 122 (1.5 g, 5 mmol) in 40 mL of tetrahydrofuran was treated with excess methyl iodide. The mixture was stirred at 50° C. for 4 hours. The finely crystalline, yellow solid thus obtained (1.8 g, 82%) melted at 120°–121° C. and had the structure

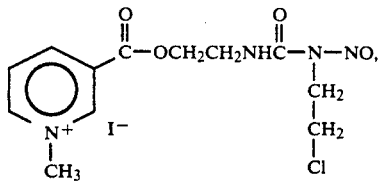

as confirmed by elemental analysis.

EXAMPLE 124

Preparation of
N-(2-Chloroethyl)-N'-[2-(1,4-dihydro-1-methyl-3-pyridinecarbonyloxy)ethyl]-N-nitrosourea A solution of the quaternary nitrosourea prepared in Example 123 (0.48 g, 1.1 mmol) and 1-benzyl-1,2-dihydroisonicotinamide (0.23 g, 1 mmol) in 25 mL of anhydrous methanol was stirred at 0° C. for 4 hours under nitrogen. The solid which separated was filtered and washed with methanol and ether. The solid was identified as 1-benzyl-4-carbamoylpyridinium iodide by NMR. The filtrate was evaporated in vacuo at about 30° C. and the residue was suspended in methylene chloride. The solid that separated was filtered and washed with methylene chloride. The filtrate was evaporated in vacuo and the residue was dissolved in chloroform.

Flash chromatography on a short column of neutral alumina, using chloroform as eluent, gave a chloroform solution which was evaporated in vacuo to afford 0.2 g (63%) of a gummy residue, identified by NMR as the desired product of the formula

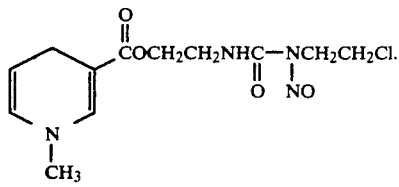

An alcoholic solution of silver nitrate was readily reduced by the compound thus obtained.

EXAMPLE 125

Preparation of N-(2-Fluoroethyl)-N'-[2-(3-pyridinecarbonyloxy)ethyl]-N-nitrosourea A solution of 2-aminoethyl nicotinate dihydrochloride (1.5 g, 6.3 mmol) and 2,4,5-trichlorophenyl-N-(2-fluoroethyl)-N-nitrosocarbamate (2.18 g, 6.9 mmol) in 50 mL of pyridine was stirred under nitrogen at room temperature for 24 hours. The reaction was monitored by thin layer chromatography (silica, 1:1 chloroform/ethyl acetate, $R_f$ 0.25). The solvent was removed in vacuo and the residue was chromatographed on a silica gel column by eluting, first with benzene to remove unreacted nitrosocarbamate and trichlorophenol, and then with chloroform to elute the desired product. The compound (1.56 g, 87.4%) melted at 75°-77° C. and was characterized by the structural formula:

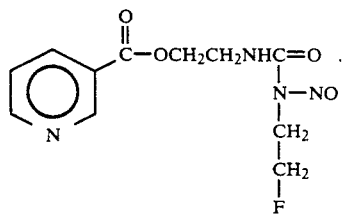

EXAMPLE 126

Preparation of N-(2-Fluoroethyl)-N'-[2-(1-methyl-3-pyridiniumcarbonyloxy)ethyl]-N-nitrosourea iodide A solution of the product of Example 125 (1.56 g, 5.4 mmol) in 40 mL of tetrahydrofuran was treated with excess methyl iodide. The mixture was stirred at 50° C. for 4 hours. The finely crystalline, yellow solid thus obtained (2.20 g, 94.1%) melted at 123°-125° C. and had the structural formula

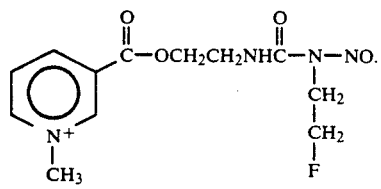

EXAMPLE 127

Preparation of N-(2-Fluoroethyl)-N'-[2-(1,4-dihydro-1-methyl-3-pyridinecarbonyloxy)ethyl]-N-nitrosourea A solution of the quaternary nitrosourea prepared in Example 126 (0.426 g, 1 mmol) and 1-benzyl-1,2-dihydroisonicotinamide (0.21 g, 1 mmol) in 25 mL of anhydrous methanol was stirred at 0° C. for 4 hours under nitrogen. The solvent was evaporated in vacuo at about 30° C. and the residue was suspended in chloroform, filtered and flash chromatographed on a short column of neutral alumina. The title compound was obtained in 55% yield after elution with chloroform and was assigned the structure

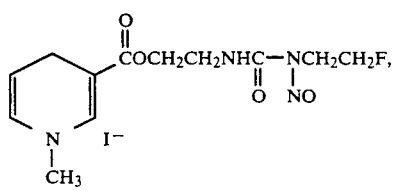

consistent with UV analysis.

EXAMPLE 128

Preparation of Chloromethyl nicotinate

To a suspension of nicotinic acid (1.23 g, 0.01 mol) in a mixture of 10 mL of water and 20 mL of tetrahydrofuran were added tetrabutylammonium hydrogensulfate (0.34 g, 1 mmol) and sodium bicarbonate (3.19 g, 0.038 mol), with vigorous stirring. Chloromethyl chlorosulfate (1.81 g, 0.011 mol) in 5 mL of tetrahydrofuran was added dropwise, keeping the temperature below 30° C. The reaction mixture was stirred for 1 hour, then the layers were separated and the organic layer was dried by azeotroping with 1:1 acetonitrile/benzene. The residue was passed through a column of neutral alumina, eluting with chloroform. The chloroform layer was evaporated to give 1.28 g (74.8%) of an oily residue, which was confirmed by NMR analysis to have the structural formula:

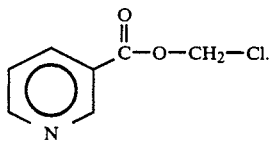

EXAMPLE 129

Preparation of 1-(Pyridine-3-carbonyloxymethyl)-5-fluorouracil

5-FU (1.31 g, 0.01 mol) was dissolved in 5 mL of dimethylacetamide and treated with triethylamine (2.78 mL, 0.02 mol). Chloromethyl nicotinate (2.95 g, 0.012 mol) in 5 mL of dimethylacetamide was added in one portion, and the mixture was stirred for 24 hours, filtered, washed with ethyl acetate and evaporated. The residue was chromatographed on a column of silica gel, using as eluent first benzene, then 3:1 benzene/chloroform, then 1:1 benzene/chloroform, then 3:1 chloroform/benzene, then chloroform and finally 99:1 chloroform/methanol. Unreacted nicotinate was eluted initially, followed by the 1,3-bis-isomer and finally the 1-isomer. The 1-isomer (1.3 g, 50%) melted at 190°–192° C. and had the formula

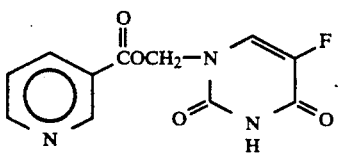

as confirmed by NMR analysis.

EXAMPLE 130

Preparation of 1,3-Bis(pyridine-3-carbonyloxymethyl)-5-fluorouracil

5-FU (1.31 g, 0.01 mol) was dissolved in 5 mL of dimethylacetamide and treated with triethylamine (5.6 mL, 0.04 mol). Chloromethyl nicotinate (6.8 g, 0.04 mol) in 15 mL of dimethylacetamide was added in one portion, then the mixture was stirred for 48 hours and filtered, and the filter cake was washed with ethyl acetate. The filtrate was evaporated in vacuo and the residue was diluted with 100 mL of water and extracted with chloroform. The organic layer was evaporated and the residue was dried by azeotroping with 1:1 acetonitrile/benzene. The residue was chromatographed on a column of neutral alumina, eluting successively with benzene, 1:1 benzene/chloroform, and 50:50:1 benzene/chloroform/methanol, to give 3.2 g (80%) of the bis-isomer of the formula

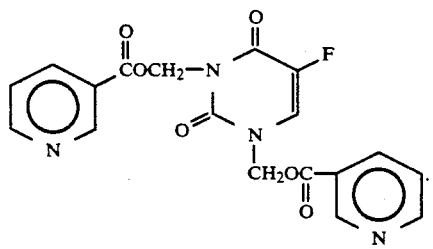

as confirmed by NMR analysis.

EXAMPLE 131

Preparation of 3-(Pyridine-3-carbonyloxymethyl)-5-fluorouracil

The 1,3-bis-isomer prepared in Example 130 was dissolved in 10 mL of methanol and mixed with 20 mL of potassium carbonate:sodium bicarbonate buffer (0.1M), pH 10.00. The mixture was stirred at room temperature for 2 hours, by which time thin layer chromatography indicated that the bis-isomer had disappeared completely. The mixture was evaporated and the residue was chromatographed on a column of alumina, eluting successively with chloroform, 99:1 chloroform/methanol and 96:4 chloroform/methanol. The fractions were collected and those containing the 3-isomer were pooled and evaporated to give the compound of the formula

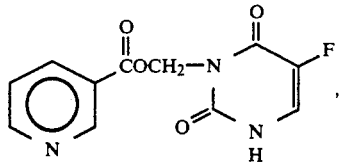

as a solid (0.2 g, 30%) melting at 179°–180° C. The identity of the product was confirmed by NMR analysis.

EXAMPLE 132

Preparation of 1-(1-Methyl-3-pyridiniumcarbonyloxymethyl)-5-fluorouracil iodide

The 1-isomer prepared in Example 129 (1.93 g) was combined with sufficient quantities of methyl iodide and acetonitrile, and the mixture was refluxed for 4 hours, then cooled and filtered to give 2.5 g of a light yellow, fluffy solid. The filtrate was evaporated, triturated with acetonitrile and filtered to give an additional 0.23 g; total yield 2.73 g (92.25%). UV and NMR analyses confirmed that the product had the structural formula:

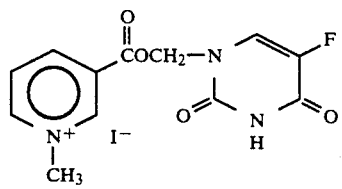

EXAMPLE 133

Preparation of 1-(1,4-Dihydro-1-methyl-3-pyridinylcarbonyloxymethyl)-5-fluorouracil The product of Example 132 (1 g) was dissolved in 20 mL of deionized water (degassed with argon) and cooled in an ice-bath, then 20 mL of ethyl acetate were added. To the stirred solution, 1.24 g of sodium bicarbonate were added, followed after about one minute with 1.75 g of sodium dithionite. The reaction was allowed to proceed under argon and was monitored by UV. After approximately 75 minutes, ethanol was added and the solid was filtered, washed with water and methylene chloride and dried under argon to give 400 mg of the title compound. UV and NMR analyses confirmed that the product had the structural formula:

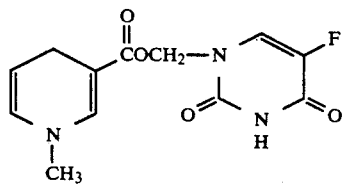

The aqueous layer was repeatedly extracted with chloroform and combined with the ethyl acetate layer used in the reaction. The solid obtained after removal of the organic solvent was suspended in acetonitrile and filtered to give an additional 250 mg of product melting at 173°–174° C.

EXAMPLE 134

Preparation of 3-(1-Methyl-3-pyridiniumcarbonyloxymethyl)-5-fluorouracil iodide The 3-isomer prepared in Example 131 can be subjected to the general procedure of Example 132 to afford the corresponding quaternary salt of the formula:

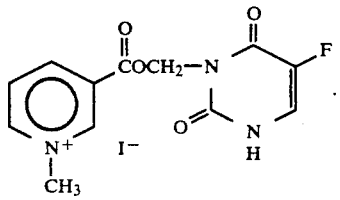

EXAMPLE 135

Preparation of 3-(1,4-Dihydro-1-methyl-3-pyridinylcarbonyloxymethyl)-5-fluorouracil The product of Example 134 can be subjected to the general procedure of Example 133 to afford the corresponding dihydropyridine of the formula:

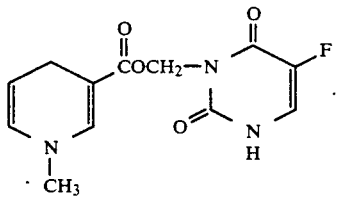

The parenteral formulations employed in the method of the present invention can be used to treat a variety of conditions, depending upon the pharmacological nature of the drug selected for administration. In the case of the redox carrier-drugs, the pharmacological nature of the parent drug itself from which the carrier drug is derived will be determinative. Thus, with respect to the carrier-drugs, in one preferred embodiment, the redox system is derived from dopamine or L-DOPA or a protected counterpart thereof, and the redox derivative/cyclodextrin parenteral formulation is thus designed to elicit a sustained and brain-specific dopaminergic (e.g. anti-Parkinsonism or antihyperprolactinemia) response in the animal to which the formulation is administered. In analogous fashion, the redox derivative/cyclodextrin parenteral formulation derived from any other centrally acting drug as defined herein is designed to elicit the kind of pharmacological response which would be obtained by delivery of the drug itself to the brain, i.e. when the centrally acting parent drug is an antitumor/anticancer agent, the instant formulation is employed to elicit an antitumor/anticancer response; when the parent drug is a sympathetic stimulant, the instant formulation is used to elicit a sympathetic stimulant or amphetamine-like response; when the parent drug is an anticonvulsant compound, the instant formulation is used to elicit an anticonvulsant response; when the parent drug is a tranquilizer, the instant formulation is used to elicit a tranquilizing response; when the parent drug is an antidepressant, the instant formulation is used to elicit an antidepressant response; and so forth.

The parenteral formulations used in the method of the present invention contain a pharmacologically effective amount of at least one selected lipophilic and/or water-labile drug in an aqueous solution containing from about 20% to about 50% cyclodextrin selected from the group consisting of hydroxypropyl, hydroxyethyl, glucosyl, maltosyl and maltotriosyl derivatives of $\beta$- and $\gamma$-cyclodextrin, preferably of hydroxypropyl-$\beta$-cyclodextrin. These formulations are sterile and pyrogen-free, and are prepared in accord with accepted pharmaceutical procedures, for example as described in *Remington's Pharmaceutical Sciences*, seventeenth edition, ed. Alfonso R. Gennaro, Mack Publishing Company, Easton, Pa. (1985), pp. 1518–1552. The aqueous sterile injection solutions may further contain anti-oxidants, buffers, bacteriostats, isotonicity adjusters and like additions acceptable for parenteral formulations. Various unit dose and multidose containers, e.g. sealed ampules and vials, may be used, as is well-known in the art. The essential ingredients of the sterile parenteral formulation, i.e. the drug(s), water and selected cyclodextrin, may be presented in a variety of ways, just so long as the solution ultimately administered to the patient contains the appropriate amounts of the essential ingredients. Thus, for example, the drug/cyclodextrin/water formulation may be presented in a unit dose or multidose container, ready for injection. As another example, a concentrated solution of drug/cyclodextrin/water may be presented in a separate container from a diluting liquid (water or cyclodextrin/water) designed so that the contents can be combined to give a formulation containing appropriate amounts for injection. As another alternative, the drug or a drug/cyclodextrin combination may be provided in a freeze-dried condition in one container, while a separate container contains diluting liquid (water or cyclodextrin/water, depending on the amount of cyclodextrin in the other container), again designed so that the contents can be combined to give a formulation containing the appropriate amounts of the essential ingredients. In any event, the contents of each container will be sterile.

Generally speaking, the therapeutic dosage ranges for administration of drugs in the parenteral formulations described herein will be the same as or less than (in some instances, substantially less than) those characteristically used for administration of the drug per se (or, in the case of the carrier-drugs, of the parent drug species per se). Naturally, such therapeutic dosage ranges will vary with the size and species of the patient, the condition for which the formulation is administered, the type of parenteral administration employed and the like. The quantity of given dosage form needed to deliver the desired dose of active ingredients will of course depend upon the concentration of the drug in the parenteral formulation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for decreasing the incidence of precipitation of a lipophilic and/or water-labile drug occurring at or near the injection site and/or in the lungs or other organs following parenteral administration, said method comprising parenterally administering said drug in an aqueous solution containing from about 20% to about 50% cyclodextrin selected from the group consisting of hydroxyethyl, glucosyl, maltosyl and maltotriosyl derivatives of β-cyclodextrin and hydroxypropyl, hydroxyethyl, glucosyl, maltosyl and maltotriosyl derivatives of γ-cyclodextrin.

2. A method according to claim 1, wherein the aqueous solution is approximately isotonic.

3. A method according to claim 1, wherein said drug is an antineoplastic.

4. A method according to claim 1, wherein said drug is a sedative, tranquilizer, anticonvulsant, antidepressant, hypnotic, muscle relaxant or antispasmodic.

5. A method according to claim 1, wherein said drug is an androgen, estrogen, progestin or anti-inflammatory steroid.

6. A method according to claim 1, wherein said drug is a steroidal hypnotic or anesthetic.

7. A method according to claim 1, wherein said drug is an anticoagulant, cardiotonic, vasodilator, vasoconstrictor, platelet inhibitor or anti-arrhythmic.

8. A method according to claim 1, wherein said drug is an antifungal, antiprotozoal, antibacterial, antibiotic or antiviral.

9. A method according to claim 1, wherein said drug is a vitamin/nutritional factor, emetic, antiemetic, diuretic, non-steroidal anti-inflammatory agent, anesthetic, hypoglycemic, radiodiagnostic, carbonic anhydrase inhibitor, narcotic antagonist, narcotic agonist, mixed narcotic agonist-antagonist, pharmacologically active protein, dopaminergic/anti-Parkinsonism agent or agent for treating Alzheimer's disease.

10. A method according to claim 3, wherein said drug is chlorambucil, lomustine, melphalan, methotrexate, hexamethylmelamine, teniposide, etoposide, semustine, fazarabine, mercaptopurine, tubulazole, carmofur, carmustine, amsacrine, bruceantin, diaziquone, didemnin B, echinomycin or PCNU.

11. A method according to claim 4, wherein said drug is a barbiturate or a benzodiazepine.

12. A method according to claim 11, wherein said drug is pentobarbital, phenobarbital, secobarbital, chlordiazepoxide, diazepam, medazepam, oxazepam or lorazepam.

13. A method according to claim 4, wherein said drug is phenytoin, sulpiride or etomidate.

14. A method according to claim 5, wherein said drug is dexamethasone, hydrocortisone, prednisolone, 17β-estradiol, 17α-ethynylestradiol, ethynylestradiol 3-methyl ether, estriol, norethindrone, norethindrone acetate, norgestrel, ethisterone, medroxyprogesterone acetate, progesterone, 17-methyltestosterone or testosterone.

15. A method according to claim 6, wherein said drug is alfaxalone.

16. A method according to claim 7, wherein said drug is dicumarol, digoxin, digitoxin, nitroglycerin, flunarizine, alprostadil or prostacyclin.

17. A method according to claim 8, wherein said drug is ampicillin, penicillin G, ketoconazole, itraconazole, metronidazole benzoate, miconazole, flubendazole or co-trimoxazole.

18. A method according to claim 9, wherein said drug is retinol, vitamin A-acetate, cholecalciferol, retinal, an E, D or K vitamin, apomorphine, chlorthalidone, furosemide, spironolactone, indomethacin, piroxicam, flurbiprofen, acetazolamide, lidocaine, acetohexamide, dimenhydrinate, L-DOPA or THA.

19. A method according to claim 1, wherein said drug is the reduced, biooxidizable, blood-brain barrier penetrating, lipoidal dihydropyridine form of a dihydropyridine⇌pyridinium salt redox system for brain-targeted drug delivery.

20. A method according to claim 19, wherein the aqueous solution is approximately isotonic.

21. A method according to claim 19, wherein said dihydropyridine form is a compound of the formula

[D-DHC]

wherein [D] is a centrally acting drug species and [DHC] is the reduced, biooxidizable, blood-brain barrier penetrating, lipoidal form of a dihydropyridine⇌pyridinium salt redox carrier.

22. A method according to claim 21, wherein the centrally acting drug species is a dopaminergic agent, an androgenic agent, an anticonvulsant, an anxiolytic agent, a neurotransmitter, an antibiotic or antibacterial agent, an antidepressant, an antiviral agent, an anticancer or antitumor agent, an antiinflammatory agent, an estrogen or a progestin.

23. A method according to claim 22, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

24. A method according to claim 23, wherein the compound of the formula [D-DHC] is 1-methyl-3-{{N-{β-[3,4-bis(pivalyloxy)phenyl]ethyl}carbamoyl}}-1,4-dihydropyridine, 1-methyl-3-{N-[[β-[3,4-bis(isobutyryloxy)phenyl]ethyl]]}carbamoyl-1,4-dihydropyridine or N-{β-[3,4-bis(pivalyloxy)phenyl]ethyl}aminocarbonyloxymethyl 1,4-dihydro-1-methyl-3-pyridinecarboxylate.

25. A method according to claim 23, wherein the compound of the formula [D-DHC] is 17β-[(1,4-dihydro-1-methyl-3-pyridinylcarbonyl)oxy]androst-4-en-3-one or 17β-{[(3''-carbamoyl-1',4'-dihydropyridinyl)acetyl]oxy}androst-4-en-3-one.

26. A method according to claim 23, wherein the compound of the formula [D-DHC] is 5,5-diphenyl-3-[(1'-methyl-1',4'-dihydropyridin-3'-yl)carbonyloxymethyl]-2,4-imidazolidinedione, 3-[(3'-carbamoyl-1',4'-dihydropyridin-1'-yl)acetyloxymethyl]-5,5-diphenyl-2,4-imidazolidinedione or 3-[3'-(3''-carbamoyl-1'',4''-dihydropyridin-1''-yl)propionyloxymethyl]-5,5-diphenyl-2,4-imidazolidinedione.

27. A method according to claim 23, wherein the compound of the formula [D-DHC] is 1-methyl-3-N-[3-(benzyloxycarbonyl)propyl]carbamoyl-1,4-dihydropyridine or 1-methyl-3-{N-[(3'-cyclohexylcarbonyl)propyl]}-carbamoyl-1,4-dihydropyridine.

28. A method according to claim 23, wherein the compound of the formula [D-DHC] is 1-methyl-3-[2'-(2''-propyl)pentanoyloxy]ethylcarbamoyl-1,4-dihydropyridine, 1-methyl-3-[2'-(2''-propyl)pentanoyloxy]ethoxycarbonyl-1,4-dihydropyridine or 1-[2'-(2''-propyl)pentanoyloxy]ethyl-3-carboxamide-1,4-dihydropyridine.

29. A method according to claim 23, wherein the compound of the formula [D-DHC] is 1-methyl-3-{N-[(1'-ethoxycarbonyl)-2'-(4''-pivaloyloxyphenyl)ethyl]}- carbamoyl-1,4-dihydropyridine or 1-methyl-3-{N-[(1'-ethoxycarbonyl)-2'-(4"-isobutyryloxyphenyl)ethyl]}carbamoyl-1,4-dihydropyridine.

30. A method according to claim 23, wherein the compound of the formula [D-DHC] is [[(1,4-dihydro-1-methyl-3-pyridinyl)carbonyl]oxy]methyl [2S-(2α,5α,6β)]-3,3-dimethyl-7-oxo-6-[(2,6-dimethoxy)benzamido]-4-thia-1-azabicyclo[3.2.0]heptane-2-carboxylate, [[(1,4-dihydro-1-methyl-3-pyridinyl)carbonyl]oxy]methyl [2S-(2α,5α,6β)-3,3-dimethyl-6-(5-methyl-3-phenyl-4-isoxazolecarboxamido)-7-oxo-4-thia-1-azabicyclo[3.2.0]heptane-2-carboxylate, [[(1,4-dihydro-1-methyl-3-pyridinyl)carbonyl]oxy]methyl [2S-(2α,5α,6β)]-3,3-dimethyl-7-oxo-6-[(phenylacetyl)amino]-4-thia-1-azabicyclo[3.2.0]heptane-2-carboxylate, [[(1,4-dihydro-1-methyl-3-pyridinyl)carbonyl]oxy]methyl [2S-(2α,5α,6β)]-6-[3-(2-chlorophenyl)-5-methyl-4-isoxazolecarboxamido]-3,3-dimethyl-7-oxo-4-thia-1-azabicyclo[3.2.0]heptane-2-carboxylate or [[(1,4-dihydro-1-methyl-3-pyridinyl)carbonyl]oxy]methyl [2S-(2α,5α,6β)]-6-[3-(2,6-dichlorophenyl)-5-methyl-4-isoxazolecarboxamido]-3,3-dimethyl-7-oxo-4-thia-1-azabicyclo[3.2.0]heptane-2-carboxylate.

31. A method according to claim 23, wherein the compound of the formula [D-DHC] is [{N-[3-(10,11-dihydro-5H-dibenz(b,f]azepin-5-yl)]propyl-N-methylamino}carbonyloxy]methyl 1,4-dihydro-1-methyl-3-pyridinecarboxylate or [1-{N-[3-(10,11-dihydro-5H-dibenz[b,f]azepin-5-yl)]propyl-N-methylamino}carbonyloxy]ethyl 1,4-dihydro-1-methyl-3-pyridinecarboxylate.

32. A method according to claim 23, wherein the compound of the formula [D-DHC] is 1-methyl-3-{[2-(9-guanylmethoxy)ethoxy]carbonyl}-1,4-dihydropyridine.

33. A method according to claim 23, wherein the compound of the formula [D-DHC] is 3'-(1,4-dihydro-1-methyl-3-pyridinylcarbonyl)-5'-pivaloyltrifluorothymidine.

34. A method according to claim 23, wherein the compound of the formula [D-DHC] is 3'-azido-3'-deoxy-5'-(1-methyl-1,4-dihydro-3-pyridinyl)carbonyl]-thymidine.

35. A method according to claim 23, wherein the compound of the formula [D-DHC] is N-(2-chloroethyl)-N'-[4-(1,4-dihydro-1-methyl-3-pyridinecarbonyloxy)cyclohexyl]-N-nitrosourea, N-(2-fluoroethyl)-N'-[2-(1,4-dihydro-1-methyl-3-pyridinecarbonyloxy)ethyl]-N-nitrosourea or N-(2-chloroethyl)-N'-[2-(1,4-dihydro-1-methyl-3-pyridinecarbonyloxy)ethyl]-N-nitrosourea.

36. A method according to claim 23, wherein the compound of the formula [D-DHC] is 1-methyl-3-[(N-{2-[4-({4-[bis(2-chloroethyl)]amino}phenyl)-butanoyloxy]ethyl})carbamoyl]-1,4-dihydropyridine, 1-methyl-3-(N-{4-[4-(4-{[bis(2-chloroethyl)]amino}phenyl)butanoyloxy]cyclohexyl}carbamoyl)-1,4-dihydropyridine, 1-methyl-3-[(N-{2-[4-({4-bis(2-chloroethyl)]amino}phenyl)butanoyloxy]propyl})carbamoyl]-1,4-dihydropyridine, 1-methyl-3-[(N-{2-phenyl-2-({4-[bis(2-chloroethyl)]amino}phenyl)butanoyloxy]}ethyl)-carbamoyl]-1,4-dihydropyridine or 1-methyl-3-[N-({1-[4-(4-{[bis(2-chloroethyl)]amino}phenyl)butanoyloxy]-cyclohexyl}methyl)carbamoyl]-1,4-dihydropyridine.

37. A method according to claim 23, wherein the compound of the formula [D-DHC] is 1-methyl-3-N-[2-(3-indolyl)ethyl]carbamoyl-1,4-dihydropyridine.

38. A method according to claim 23, wherein the compound of the formula [D-DHC] is 9-fluoro-11β,17-dihydroxy-16α-methyl-21-{[(1-methyl-1,4-dihydropyridin-3-yl)carbonyl]oxy}pregna-1,4-diene-3,20-dione or 11β,17-dihydroxy-21-{[(1-methyl-1,4-dihydropyridin-3-yl)carbonyl]oxy}pregn-4-ene-3,20-dione.

39. A method according to claim 23, wherein the compound of the formula [D-DHC] is 3-hydroxy-17β-[(1-methyl-1,4-dihydropyridin-3-yl)carbonyl]oxyestra-1,3,5(10)-triene.

40. A method according to claim 23, wherein the compound of the formula [D-DHC] is 3-hydroxy-17β-{[1-methyl-1,4-dihydropyridin-3-yl)carbonyl]oxy}-19-nor-17α-pregna-1,3,5(10)-trien-20-yne, 3-[(1-methyl-1,4-dihydro-3-pyridinyl)carbonyloxy]estra-1,3,5(10)-trien-17-one, 17β-[(1-methyl-1,4-dihydro-3-pyridinyl)carbonyloxy]estra-1,3,5(10)-trien-3-ol 3-methyl ether, 3,17β-bis-{[(1-methyl-1,4-dihydropyridin-3-yl)carbonyl]oxy}estra-1,3,5(10)-triene, 3-(phenylcarbonyloxy)-17β-{[(1-methyl-1,4-dihydropyridin-3-yl)carbonyl]oxy}estra-1,3,5(10-triene or 3-methoxy-17β-{[1-methyl-1,4-dihydropyridin-3-yl)carbonyl]oxy}-19-nor-17α-pregna-1,3,5(10)-trien-20-yne.

41. A method according to claim 23, wherein the compound of the formula [D-DHC] is 17β-{[(1-methyl-1,4-dihydropyridin-3-yl)carbonyl]oxy}-19-norpregn-4-en-20-yn-3-one, 17β-{[(1-methyl-1,4-dihydropyridin-3-yl)carbonyl]oxy}pregn-4-en-20-yn-3-one, 13-ethyl-17β-{[(1-methyl-1,4-dihydropyridin-3-yl)carbonyl]oxy}-18,19-dinorpregn-4-en-20-yn-3-one or 17β-{[(1-methyl-1,4-dihydropyridin-3-yl)carbonyl]oxy}-19-norpregn-5(10)-en-20-yn-3-one.

42. A method according to claim 23, wherein the compound of the formula [D-DHC] is 1-methyl-3-[N-(2-{1-(p-chlorobenzoyl)-5-methoxy-2-methyl-3-indolyl]acetoxy}ethyl)carbamoyl]-1,4-dihydropyridine or 1-methyl-3-{N-[2-(6-methoxy-α-methyl-2-naphthalenylacetoxy)ethyl]carbamoyl-1,4-dihydropyridine.

43. A method according to claim 23, wherein the compound of the formula [D-DHC] is 3-(1,4-dihydro-1-methyl-3-pyridinylcarbonyloxymethyl)-5-fluorouracil or 1-(1,4-dihydro-1-methyl-3-pyridinecarbonyloxymethyl-5-fluorouracil.

44. A method for decreasing the tendency of a lipophilic and/or water-labile drug to collect in the lungs or other organs due to precipitation at or near the injection site and/or in the lungs or other organs themselves following parenteral administration, said method comprising formulating said drug in an aqueous solution adapted for parenteral administration containing from about 20% to about 50% cyclodextrin selected from the group consisting of hydroxyethyl, glucosyl, maltosyl and maltotriosyl derivatives of β-cyclodextrin and hydroxypropyl, hydroxyethyl, glucosyl, maltosyl and maltotriosyl derivatives of γ-cyclodextrin.

45. A method according to claim 44, wherein the aqueous solution is approximately isotonic.

46. A method according to claim 44, wherein said drug is an antineoplastic.

47. A method according to claim 44, wherein said drug is a sedative, tranquilizer, anticonvulsant, antidepressant, hypnotic, muscle relaxant or antispasmodic.

48. A method according to claim 44, wherein said drug is an androgen, estrogen, progestin or anti-inflammatory steroid.

49. A method according to claim 44, wherein said drug is a steroidal hypnotic or anesthetic.

50. A method according to claim 44, wherein said drug is an anticoagulant, cardiotonic, vasodilator, vasoconstrictor, platelet inhibitor or anti-arrhythmic.

51. A method according to claim 44, wherein said drug is an antifungal, antiprotozoal, antibacterial, antibiotic or antiviral.

52. A method according to claim 44, wherein said drug is a vitamin/nutritional factor, emetic, antiemetic, diuretic, non-steroidal anti-inflammatory agent, anesthetic, hypoglycemic, radiodiagnostic, carbonic anhydrase inhibitor, narcotic antagonist, narcotic agonist, mixed narcotic agonist-antagonist, pharmacologically active protein, dopaminergic/anti-Parkinsonism agent or agent for treating Alzheimer's disease.

53. A method according to claim 46, wherein said drug is chlorambucil, lomustine, melphalan, methotrexate, hexamethylmelamine, teniposide, etoposide, semustine, fazarabine, mercaptopurine, tubulazole, carmofur, carmustine, amsacrine, bruceantin, diaziquone, didemnin B, echinomycin or PCNU.

54. A method according to claim 47, wherein said drug is a barbiturate or a benzodiazepine.

55. A method according to claim 54, wherein said drug is pentobarbital, phenobarbital, secobarbital, chlordiazepoxide, diazepam, medazepam, oxazepam or lorazepam.

56. A method according to claim 47, wherein said drug is phenytoin, sulpiride or etomidate.

57. A method according to claim 48, wherein said drug is dexamethasone, hydrocortisone, prednisolone, 17β-estradiol, 17α-ethynylestradiol, ethynylestradiol 3-methyl ether, estriol, norethindrone, norethindrone acetate, norgestrel, ethisterone, medroxyprogesterone acetate, progesterone, 17-methyltestosterone or testosterone.

58. A method according to claim 49, wherein said drug is alfaxalone.

59. A method according to claim 50, wherein said drug is dicumarol, digoxin, digitoxin, nitroglycerin, flunarizine, alprostadil or prostacyclin.

60. A method according to claim 51, wherein said drug is ampicillin, penicillin G, ketoconazole, itraconazole, metroindazole benzoate, miconazole, flubendazole or co-trimoxazole.

61. A method according to claim 52, wherein said drug is retinol, vitamin A-acetate, cholecalciferol, retinal, an E, D or K vitamin, apomorphine, chlorthalidone, furosemide, spironolactone, indomethacin, piroxicam, flurbiprofen, acetazolamide, lidocaine, acetohexamide, dimenhydrinate, L-DOPA or THA.

62. A method according to claim 44, wherein said drug is the reduced, biooxidizable, blood-brain barrier penetrating, lipoidal dihydropyridine form of a dihydropyridine⇌pyridinium salt redox system for brain-targeted drug delivery.

63. A method according to claim 62, wherein the aqueous solution is approximately isotonic.

64. A method according to claim 62, wherein said dihydropyridine form is a compound of the formula

[D-DHC]

wherein [D] is a centrally acting drug species and [DHC] is the reduced, biooxidizable, blood-brain barrier penetrating, lipoidal form of a dihydropyridine⇌pyridinium salt redox carrier.

65. A method according to claim 64, wherein the centrally acting drug species is a dopaminergic agent, an androgenic agent, an anticonvulsant, an anxiolytic agent, a neurotransmitter, an antibiotic or antibacterial agent, an antidepressant, an antiviral agent, an anticancer or antitumor agent, an antiinflammatory agent, an estrogen or a progestin.

66. A method according to claim 65, wherein the centrally acting drug species is dopamine, testosterone, phenytoin, GABA, valproic acid, tyrosine, methicillin, oxacillin, benzylpenicillin, cloxacillin, dicloxacillin, desipramine, acyclovir, trifluorothymidine, zidovudine, hydroxy-CCNU, chlorambucil, tryptamine, dexamethasone, hydrocortisone, ethinyl estradiol, norethindrone, estradiol, ethisterone, norgestrel, estrone, estradiol 3-methyl ether, estradiol benzoate, norethynodrel, mestranol, indomethacin, naproxen, FENU, HENU or 5-FU.

67. A method according to claim 66, wherein the compound of the formula [D-DHC] is 1-methyl-3-{{N-{β-[3,4-bis(pivalyloxy)phenyl]ethyl}carbamoyl}}-1,4-dihydropyridine, 1-methyl-3-{N-[[β-[3,4-bis(isobutyryloxy)phenyl]ethyl]]}carbamoyl-1,4-dihydropyridine or N-{β-[3,4-bis(pivalyloxy)phenyl]ethyl}aminocarbonyloxymethyl 1,4-dihydro-1-methyl-3-pyridinecarboxylate.

68. A method according to claim 66, wherein the compound of the formula [D-DHC] is 17β-[(1,4-dihydro-1-methyl-3-pyridinylcarbonyl)oxy]androst-4-en-3-one or 17β-{[(3''-carbamoyl-1',4'-dihydropyridinyl)acetyl]oxy}androst-4-en-3-one.

69. A method according to claim 66, wherein the compound of the formula [D-DHC] is 5,5-diphenyl-3-[(1'-methyl-1',4'-dihydropyridin-3'-yl)carbonyloxymethyl]-2,4-imidazolidinedione, 3-[(3'-carbamoyl-1',4'-dihydropyridin-1'-yl)acetyloxymethyl]-5,5-diphenyl-2,4-imidazolidinedione or 3-[3'-(3''-carbamoyl-1'',4''-dihydropyridin-1''-yl)propionyloxymethyl]-5,5-diphenyl-2,4-imidazolidinedione.

70. A method according to claim 66, wherein the compound of the formula [D-DHC] is 1-methyl-3-N-[3-(benzyloxycarbonyl)propyl]carbamoyl-1,4-dihydropyridine or 1-methyl-3-{N-[(3'-cyclohexylcarbonyl)propyl]}carbamoyl-1,4-dihydropyridine.

71. A method according to claim 66, wherein the compound of the formula [D-DHC] is 1-methyl-3-[2'-(2''-propyl)pentanoyloxy]ethylcarbamoyl-1,4-dihydropyridine, 1-methyl-3-[2'-(2''-propyl)pentanoyloxy]ethoxycarbonyl-1,4-dihydropyridine or 1-[2'-(2''-propyl)pentanoyloxy]ethyl-3-carboxamide-1,4-dihydropyridine.

72. A method according to claim 66, wherein the compound of the formula [D-DHC] is 1-methyl-3-{N-[(1'-ethoxycarbonyl)-2'-(4''-pivaloyloxyphenyl)ethyl]}carbamoyl-1,4-dihydropyridine or 1-methyl-3-{N-[(1'-ethoxycarbonyl)-2'-(4''-isobutyryloxyphenyl)ethyl]}carbamoyl-1,4-dihydropyridine.

73. A method according to claim 66, wherein the compound of the formula [D-DHC] is [[(1,4-dihydro-1-methyl-3-pyridinyl)carbonyl]oxy]methyl [2S-(2α,5α,6β)]-3,3-dimethyl-7-oxo-6-[(2,6-dimethoxy)benzamido]-4-thia-1-azabicyclo[3.2.0]heptane-2-carboxylate, [[(1,4-dihydro-1-methyl-3-pyridinyl)carbonyl]oxy]methyl [2S-(2α,5α,6β)-3,3-dimethyl-6-(5-methyl-3-phenyl-4-isoxazolecarboxamido)-7-oxo-4-thia-1-azabicyclo[3.2.0]heptane-2-carboxylate, [[(1,4-dihydro-1-methyl-3-pyridinyl)carbonyl]oxy]methyl [2S-(2α,5α,6β)]-3,3-dimethyl-7-oxo-6-[(phenylacetyl)amino]-4-thia-1-azabicyclo[3.2.0]heptane-2-carboxylate, [[(1,4-dihydro-1-methyl-3-pyridinyl)carbonyl]oxy]methyl

[2S-(2α,5α,6β)]-6-[3-(2-chlorophenyl)-5-methyl-4-isoxazolecarboxamido]-3,3-dimethyl-7-oxo-4-thia-1-azabicyclo[3.2.0]heptane-2-carboxylate or [[(1,4-dihydro-1-methyl-3-pyridinyl)carbonyl]oxy]methyl [2S-(2α,5α,6β)]-6-[3-(2,6-dichlorophenyl)-5-methyl-4-isoxazolecarboxamido]-3,3-dimethyl-7-oxo-4-thia-1-azabicyclo[3.2.0]heptane-2-carboxylate.

74. A method according to claim 66, wherein the compound of the formula [D-DHC] is [{N-[3-(10,11-dihydro-5H-dibenz(b,f]azepin-5-yl)]propyl-N-methylamino}carbonyloxy]methyl 1,4-dihydro-1-methyl-3-pyridinecarboxylate or [1-{N-[3-(10,11-dihydro-5H-dibenz[b,f]azepin-5-yl)]propyl-N-methylamino}carbonyloxy]ethyl 1,4-dihydro-1-methyl-3-pyridinecarboxylate.

75. A method according to claim 66, wherein the compound of the formula [D-DHC] is 1-methyl-3-{[2-(9-guanylmethoxy)ethoxy]carbonyl}-1,4-dihydropyridine.

76. A method according to claim 66, wherein the compound of the formula [D-DHC] is 3'-(1,4-dihydro-1-methyl-3-pyridinylcarbonyl)-5'-pivaloyltrifluorothymidine.

77. A method according to claim 66, wherein the compound of the formula [D-DHC] is 3'-azido-3'-deoxy-5'-(1-methyl-1,4-dihydro-3-pyridinyl)carbonyl]-thymidine.

78. A method according to claim 66, wherein the compound of the formula [D-DHC] is N-(2-chloroethyl)-N'-[4-(1,4-dihydro-1-methyl-3-pyridinecarbonyloxy)cyclohexyl]-N-nitrosourea, N-(2-fluoroethyl)-N'-[2-(1,4-dihydro-1-methyl-3-pyridinecarbonyloxy)ethyl]-N-nitrosourea or N-(2-chloroethyl)-N'-[2-(1,4-dihydro-1-methyl-3-pyridinecarbonyloxy)ethyl]-N-nitrosourea.

79. A method according to claim 66, wherein the compound of the formula [D-DHC] is 1-methyl-3-[(N-{2-[4-({4-[bis(2-chloroethyl)]amino}phenyl)-butanoyloxy]ethyl})carbamoyl]-1,4-dihydropyridine, 1-methyl-3-(N-{4-[4-(4-{[bis(2-chloroethyl)]amino}phenyl)butanoyloxy]cyclohexyl}carbamoyl)-1,4-dihydropyridine, 1-methyl-3-[(N-{2-[4-({4-bis(2-chloroethyl)]amino}phenyl)butanoyloxy]propyl})carbamoyl]-1,4-dihydropyridine, 1-methyl-3-[(N-{2-phenyl-2-({4-[bis(2-chloroethyl)]amino}phenyl)butanoyloxy]}ethyl)-carbamoyl]-1,4-dihydropyridine or 1-methyl-3-[N-({1-[4-(4-{[bis(2-chloroethyl)]amino}phenyl)butanoyloxy]-cyclohexyl}methyl)carbamoyl]-1,4-dihydropyridine.

80. A method according to claim 66, wherein the compound of the formula [D-DHC] is 1-methyl-3-N-[2-(3-indolyl)ethyl]carbamoyl-1,4-dihydropyridine.

81. A method according to claim 66, wherein the compound of the formula [D-DHC] is 9-fluoro-11β,17-dihydroxy-16α-methyl-21-{[(1-methyl-1,4-dihydropyridin-3-yl)carbonyl]oxy}pregna-1,4-diene-3,20-dione or 11β,17-dihydroxy-21-{[(1-methyl-1,4-dihydropyridin-3-yl)carbonyl]oxy}pregn-4-ene-3,20-dione.

82. A method according to claim 66, wherein the compound of the formula [D-DHC] is 3-hydroxy-17β-[(1-methyl-1,4-dihydropyridin-3-yl)carbonyl]oxyestra-1,3,5(10)-triene.

83. A method according to claim 66, wherein the compound of the formula [D-DHC] is 3-hydroxy-17β-{[1-methyl-1,4-dihydropyridin-3-yl)carbonyl]oxy}-19-nor-17α-pregna-1,3,5(10)-trien-20-yne, 3-[(1-methyl-1,4-dihydro-3-pyridinyl)carbonyloxy]estra-1,3,5(10)-trien-17-one, 17β-[(1-methyl-1,4-dihydro-3-pyridinyl)carbonyloxy]estra-1,3,5(10)-trien-3-ol 3-methyl ether, 3,17β-bis-{[(1-methyl-1,4-dihydropyridin-3-yl)carbonyl]oxy}estra-1,3,5(10)-triene, 3-(phenylcarbonyloxy)-17β-{[(1-methyl-1,4-dihydropyridin-3-yl)carbonyl]oxy}estra-1,3,5(10-triene or 3-methoxy-17β-{[1-methyl-1,4-dihydropyridin-3-yl)carbonyl]oxy}-19-nor-17α-pregna-1,3,5(10)-trien-20-yne.

84. A method according to claim 66, wherein the compound of the formula [D-DHC] is 17β-{[(1-methyl-1,4-dihydropyridin-3-yl)carbonyl]oxy}-19-norpregn-4-en-20-yn-3-one, 17β-{[(1-methyl-1,4-dihydropyridin-3-yl)carbonyl]oxy}pregn-4-en-20-yn-3-one, 13-ethyl-17β-{[(1-methyl-1,4-dihydropyridin-3-yl)carbonyl]oxy}-18,19-dinorpregn-4-en-20-yn-3-one or 17β-{[(1-methyl-1,4-dihydropyridin-3-yl)carbonyl]oxy}-19-norpregn-5(10)-en-20-yn-3-one.

85. A method according to claim 66, wherein the compound of the formula [D-DHC] is 1-methyl-3-[N-(2-{1-(p-chlorobenzoyl)-5-methoxy-2-methyl-3-indolyl]acetoxy}ethyl)carbamoyl]-1,4-dihydropyridine or 1-methyl-3-{N-[2-(6-methoxy-α-methyl-2-naphthalenylacetoxy)ethyl]carbamoyl-1,4-dihydropyridine.

86. A method according to claim 66, wherein the compound of the formula [D-DHC] is 3-(1,4-dihydro-1-methyl-3-pyridinylcarbonyloxymethyl)-5-fluorouracil or 1-(1,4-dihydro-1-methyl-3-pyridinecarbonyloxymethyl-5-fluorouracil.

* * * * *